US009775933B2

(12) United States Patent
Knisley et al.

(10) Patent No.: US 9,775,933 B2
(45) Date of Patent: Oct. 3, 2017

(54) BIOCOMPATIBLE SURFACES AND DEVICES INCORPORATING SUCH SURFACES

(71) Applicant: W. L. Gore & Associates, Inc., Newark, DE (US)

(72) Inventors: Keith A. Knisley, Flagstaff, AZ (US); Vishnu T. Marla, Newark, DE (US); Rachel Radspinner, Flagstaff, AZ (US); Paul A. Silvagni, Flagstaff, AZ (US); Jason J. Strid, Elkton, MD (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 501 days.

(21) Appl. No.: 13/773,937

(22) Filed: Feb. 22, 2013

(65) Prior Publication Data

US 2013/0231733 A1    Sep. 5, 2013

Related U.S. Application Data

(60) Provisional application No. 61/606,020, filed on Mar. 2, 2012.

(51) Int. Cl.
*A61F 2/82* (2013.01)
*A61L 31/06* (2006.01)
(Continued)

(52) U.S. Cl.
CPC ............ *A61L 31/06* (2013.01); *A61F 2/0077* (2013.01); *A61F 2/82* (2013.01); *A61L 31/048* (2013.01);
(Continued)

(58) Field of Classification Search
CPC ......................................................... A61F 2/82
(Continued)

(56) References Cited

U.S. PATENT DOCUMENTS 4,208,745 A    6/1980 Okita
4,323,525 A    4/1982 Bornat
(Continued)

FOREIGN PATENT DOCUMENTS

JP    H09-501583    2/1997
JP    2002-201779   1/2002
(Continued)

OTHER PUBLICATIONS

Bunce La, Sporn LA, Francis CW. Endothelial Cell Spreading on Fibrin Requires Fibrinopeptide B Cleavage and Amino Acid Residues 15-42 of the β Chain. J. Clin. Invest. vol. 89, Mar. 1992, 842-850.
(Continued)

*Primary Examiner* — Matthew Schall
(74) *Attorney, Agent, or Firm* — David J. Johns

(57) ABSTRACT

The invention is an improved biocompatible surface for a variety of medical purposes. The biocompatible surface employs a unique tight microstructure that demonstrates enhanced cellular response in the body, particularly when placed in contact with blood. As a blood contact surface, the present invention can be beneficially employed in a wide variety of implantable devices and in many other devices and equipment that come in contact with blood.

16 Claims, 47 Drawing Sheets

(51) Int. Cl.
*A61L 31/04* (2006.01)
*A61L 31/10* (2006.01)
*A61L 31/14* (2006.01)
*A61L 31/16* (2006.01)
*A61L 33/00* (2006.01)
*A61L 33/06* (2006.01)
*A61F 2/00* (2006.01)

(52) U.S. Cl.
CPC ............ *A61L 31/10* (2013.01); *A61L 31/146* (2013.01); *A61L 31/16* (2013.01); *A61L 33/007* (2013.01); *A61L 33/064* (2013.01); *A61F 2002/009* (2013.01); *A61L 2300/416* (2013.01); *A61L 2300/42* (2013.01); *A61L 2400/12* (2013.01); *A61L 2400/18* (2013.01)

(58) Field of Classification Search
USPC ....................................................... 623/1.39
See application file for complete search history.

(56) References Cited

U.S. PATENT DOCUMENTS

| | | | |
|---|---|---|---|
| 4,576,869 | A | 3/1986 | Malhotra |
| 5,814,405 | A | 9/1998 | Branca et al. |
| 5,879,366 | A | 3/1999 | Shaw et al. |
| 5,948,018 | A | 9/1999 | Dereume et al. |
| 5,993,489 | A | 11/1999 | Lewis et al. |
| 6,015,431 | A | 1/2000 | Thornton et al. |
| 6,019,788 | A | 2/2000 | Butters et al. |
| 6,042,605 | A | 3/2000 | Martin et al. |
| 6,120,477 | A | 9/2000 | Campbell et al. |
| 6,193,684 | B1 | 2/2001 | Burbank et al. |
| 6,287,337 | B1* | 9/2001 | Martakos et al. ............ 623/1.39 |
| 6,436,135 | B1 | 8/2002 | Goldfarb |
| 6,461,665 | B1 | 10/2002 | Scholander |
| 6,517,571 | B1 | 2/2003 | Brauker et al. |
| 6,541,589 | B1 | 4/2003 | Baillie |
| 6,559,132 | B1 | 5/2003 | Holmer |
| 7,049,380 | B1 | 5/2006 | Chang et al. |
| 7,306,729 | B2 | 12/2007 | Bacino et al. |
| 7,641,958 | B2 | 1/2010 | Berman et al. |
| 7,691,109 | B2 | 4/2010 | Armstrong et al. |
| 7,892,201 | B1 | 2/2011 | Laguna et al. |
| 2006/0233991 | A1 | 10/2006 | Humphrey et al. |
| 2009/0112309 | A1 | 4/2009 | Jaramillo et al. |
| 2010/0286716 | A1 | 11/2010 | Ford et al. |
| 2011/0039960 | A1 | 2/2011 | Xu et al. |
| 2013/0184808 | A1 | 7/2013 | Hall et al. |

FOREIGN PATENT DOCUMENTS

| | | |
|---|---|---|
| JP | 2007-514497 | 6/2007 |
| JP | 2008-536558 | 9/2008 |
| JP | 2009-538193 | 11/2009 |
| JP | 2010-517625 | 5/2010 |
| JP | 2011-516208 | 5/2011 |
| WO | 2011/019401 | 2/2011 |

OTHER PUBLICATIONS

International Search Report for PCT/US2013/027566 dated Jun. 27, 2013, corresponding to U.S. Appl. No. 13/773,937.
Scholander E, Begovac P, Improved Clinical Blood Compatibility with Carmeda® Bioactive Surface Endpoint Heparin Immobilization. Jun. 2010. pp. 1-49.
Schakenraad JM, Lam KH. *The Influence of Porosity and Surface Roughness on Biocompatibility*. In: Tissue Engineering of Vascular Prosthetic Grafts. Ed. Peter Zilla, Oct. 1999.
Pretouris, et al. Comparative Scanning Electron Microscopy of Platelets and Fibrin Networks of Human and Different Animals., Int. J. Morphol (online), 2009, vol. 27, No. 1, pp. 69-76.
Jin, G, et al., Surface modifying of microporous PTFE capillary for bilirubin removing from human plasma and its blood compatibility, Materials Science and Engineering, C28 (2008), 1480-1488.
Tanigaki, et al. Structure control and function of PTFE membranes by stretching method, Membrane, 26 (3), (2001), pp. 141-147. (machine translation).

* cited by examiner

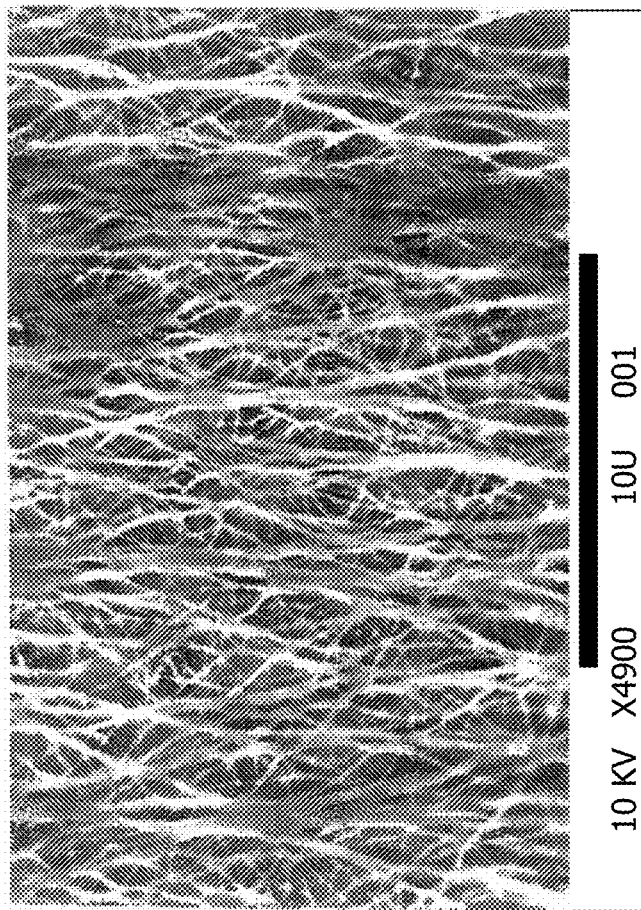
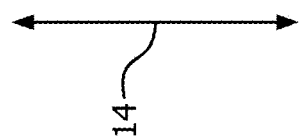
FIG. 3

| 8mm wrapped film tube construct | 4 layers of 1st embodiment of inventive film, cross-plied | 60 layers of 2nd embodiment of inventive film, circumferential wrap |
|---|---|---|
| Wall thickness | 0.069 mm | 0.029 mm |
| Axial break load | 8.6 kg | 5.3 kg |
| Burst strength | 717 kPa | 1386 kPa |
| ID inter nodal distance | 2.5 μm | 1.2 μm |
| ID fibril width | 0.21 μm | 0.14 μm |
| ID fibril orientation | 55° | 57° |
| ID nodal width | 1.0 μm | 0.41 μm |
| SEM axial axis | ⟶ | ⟶ |
| Low magnification SEM of ID 200 μm | 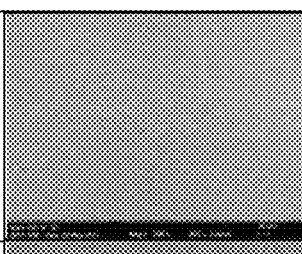 | 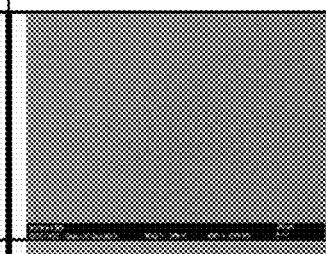 |
| Low magnification SEM of OD 200 μm | 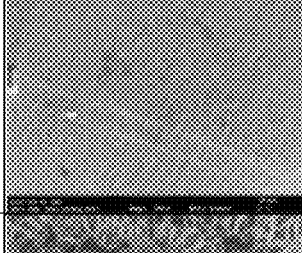 | 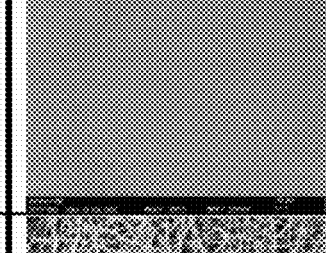 |
| High magnification SEM of ID 5 μm | 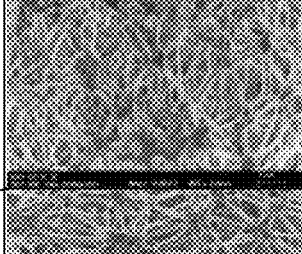 | 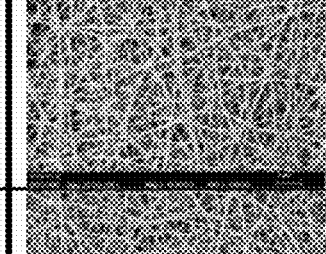 |
| High magnification SEM of OD 5 μm |  |  |

FIG. 12

Originals at 200x

Originals at 10,000x

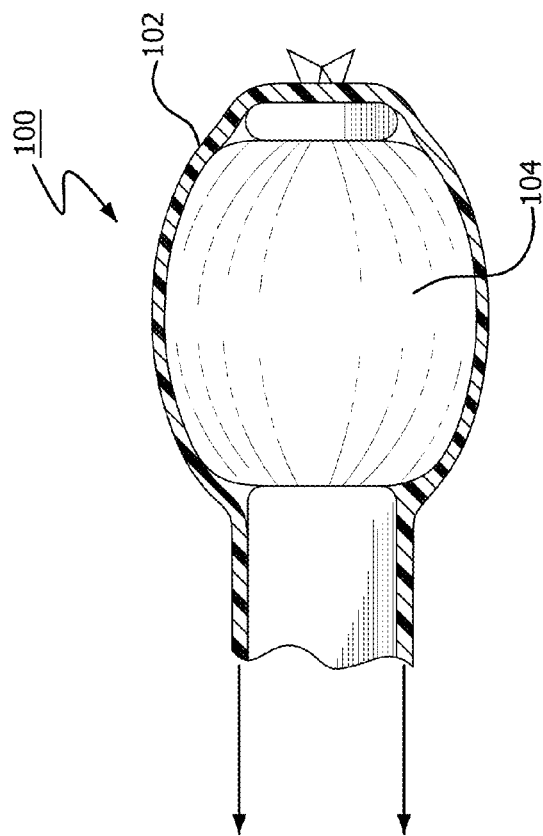
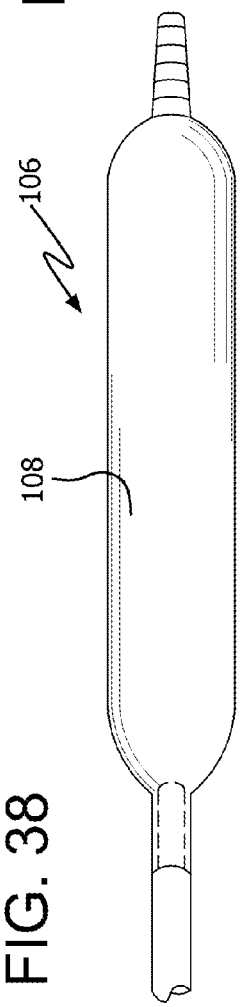
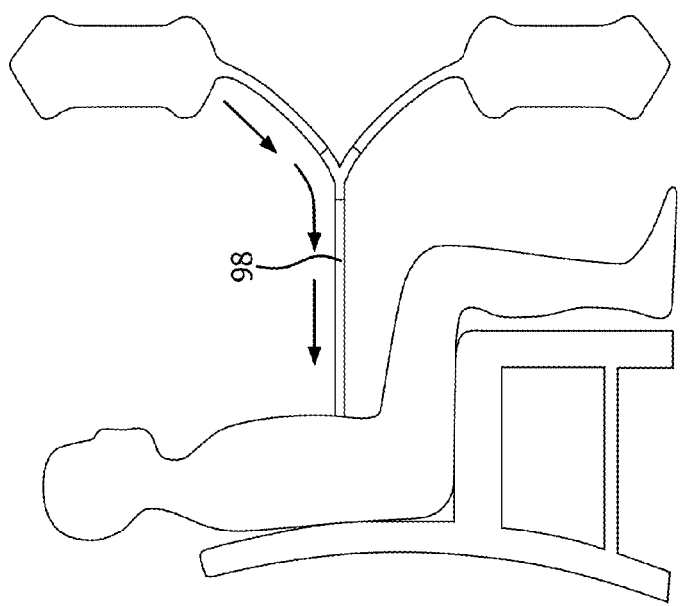
FIG. 39
FIG. 40
FIG. 38

BIOCOMPATIBLE SURFACES AND DEVICES INCORPORATING SUCH SURFACES

CROSS REFERENCE TO RELATED APPLICATIONS

This application claims priority to U.S. Provisional Patent Application Ser. No. 61/606,020 filed Mar. 2, 2012, which is incorporated herein by reference in its entirety.

BACKGROUND OF THE INVENTION

Field of the Invention

The invention relates to materials suitable for use in a variety of medical devices, particularly in medical devices adapted to carry or contact blood, including devices implanted or temporally used in the body and devices that carry or contact blood extracorporeally.

Discussion of the Related Art

A variety of devices are used to convey blood or otherwise make contact with blood in both mammalian bodies and extracorporeally. Such devices include vascular grafts, stents and stent-grafts and other endoluminal devices, catheters, vascular patches, defect closure devices, blood tubing, etc. Generally, all of these devices must perform their designated functions without engendering unwanted blood clot formation, accumulation of occlusive materials, or other adverse reaction from the blood vessel or various blood components.

Some researchers believed it desirable for certain implantable medical devices, such as vascular grafts, to be both porous enough to allow certain blood components to attach to and grow into the devices but not so porous that blood and/or serum will leak through the device. For example, U.S. Pat. No. 6,436,135 to Goldfarb describes an expanded polytetrafluoroethylene (ePTFE) graft with a microstructure of nodes and fibrils and specific wall thicknesses where " . . . the average internodular distance [of a vascular graft], as measured along the axis of expansion 12, must fall within a relatively narrow range of values, viz., between approximately 6 and 80 microns." Col. 5, lines 31-34. The patent states that: "Where the average internodular distance is less than the major dimension of a typical red cell, or approximately 6 microns, inadequate cellular ingrowth has been observed. In such cases, the node/fibril superstructure is so tightly packed as to preclude either the establishment or continued nutrition of a viable neointima." Col. 5, lines 48-53.

The Goldfarb patent characterizes particular parameters required to provide a suitable surgically implanted vascular graft as follows: " . . . a prosthetic vascular device formed from a small bore tube of polytetrafluoroethylene which has been heated, expanded and sintered so as to have a microscopic superstructure of uniformly distributed nodes interconnected by fibrils and characterized by: (a) an average internodular distance which is (i) large enough to allow transmural migration of typical red cells and fibroblast [sic], and (ii) small enough to inhibit both transmural blood flow at normal pressures and excessive tissue ingrowth; and (b) an average wall thickness which is (i) small enough to provide proper mechanical conformity to adjacent cardiovascular structures, and (ii) large enough, when taken in conjunction with the associated internodular distance, to prevent leakage and excess tissue ingrowth, to allow free and uniform transmilral [sic] nutrient flow, and to assure mechanical strength and ease of implantation." Col. 3, lines 40-55.

Other researchers suggest that these theories of blood behavior described in the Goldfarb patent, particularly as applied to humans, may be incorrect. For example, U.S. Pat. No. 6,517,571 to Brauker et al., taught that the performance of a vascular graft or stent-graft could be improved by providing an extremely smooth blood contact surface. Brauker et al. recommend employing a base graft with an internodal distance between 5 to 90 micron, but then applying to that base tube a very smooth film to provide a luminal surface that resists or prevents adhesion of occlusive blood components. See, e.g., Col. 4, lines 18-24; col. 6, lines 1-5. Brauker et al. assert: "The surface smoothness is believed to avoid or reduce adherence of occlusive blood components including blood platelets which are typically of about 2-4 micron diameter. The small pore size (generally characterized as the mean fibril length of the ePTFE microstructure) is preferably less than about 5 microns and more preferably less than about 3 microns. It is believed that the fibril length or pore size may be reduced until the smooth surface is non-porous, substantially non-porous or even entirely non-porous." Col. 4, lines 47-55.

Brauker et al. define "smoothness" as follows: "The parameter of concern for smoothness of the luminal surface (surface values) of the present invention is Rq, which is the Root-Mean-Square roughness, defined as the geometric average of the roughness profile from the mean line measured in the sampling length, expressed in units of microns RMS. The luminal surface (i.e., the blood contacting surface) of the vascular graft of the present invention has a surface at least as smooth as about 1.80 microns RMS . . . " Col. 4, lines 25-33.

By providing this exceptionally smooth blood contact (luminal) surface, Brauker et al. seek to avoid accumulation of occlusive elements while still maintaining vascular graft function. The patent states: "This luminal surface lining is intended to provide a smooth surface to the vascular graft which is believed to be substantially non-adherent to occlusive blood components such as platelets, fibrin and thrombin, and impermeable to cells from the blood, thereby avoiding the formation of an occlusive coating which might ultimately increase in thickness over time and eventually result in graft occlusion. These increasingly thick coatings are known to be particularly problematic at the distal anastomoses of vascular grafts wherein it has been frequently documented that intimal hyperplasia occurring at that location will lead to occlusion and loss of graft patency. While these occlusive blood components are substantially prevented from sticking to the surface of the inventive graft, it is believed that various other blood components such as, for example, various proteins and/or endothelial cells, may still adhere to the surface without leading to a coating of the occlusive blood components responsible for a thickening neointima over time." Col. 4, line 64, to col. 5, line 15.

While the Brauker et al. patent provides significant improvements in implantable blood contact device performance, we have found that much better blood-vessel-device interaction can be achieved by significantly modifying the microstructure of the blood contact surface.

SUMMARY OF THE INVENTION

The present invention provides a novel biomaterial that is preferably utilized as an improved blood contact surface characterized by a unique node and fibril microstructure and blood contacting devices incorporating such surfaces. The biocompatible surface of the present invention comprises a combination of several characteristics, including a microstructure with a mean internodal distance ("IND") of about 5 micron or less with relatively small nodes (sometimes referred to as a "tight structure"), and relative balance in the IND distribution in both the x and y directions. Optionally, the surface of the present invention may include bioactive coatings for further enhancement of blood contract surface performance. A particular advantage of devices incorporating such inventive surfaces is that they can be made extremely thin, often less than 100 micron. This allows for creation of smaller or lower profile devices that can be implanted or used with less trauma to the patient and better conformability to the host's anatomy.

As the term "biocompatible surface" is used herein, it is intended to encompass one or more exposed surfaces of a synthetic material that is configured and employed to interact with a host's biology. To the extent that the biomaterials of the present invention interact with a host's bloodstream, the biocompatible surface of the present invention may be more specifically referred to as a "blood contact surface."

The biocompatible surface of the present invention may be incorporated into a wide variety of medical devices, including permanently implanted devices such as vascular grafts, stent-grafts, valves, patches, and the like; devices that are temporarily introduced into the body such as catheters, balloons, blood filters, and the like; and extracorporeal devices such as blood tubing used in dialysis, heart-lung machines, and similar applications. One skilled in the art will also recognize that the materials of the present invention may also be adapted for use in a variety of non-blood contact medical applications, including implantable devices used to repair various body injuries and defects, and implantable or extracorporeal devices that contact and/or transfer non-blood fluids.

BRIEF DESCRIPTION OF THE DRAWINGS

The accompanying drawings provide a further understanding of the invention and illustrate embodiments of the invention:

FIG. 3 is an SEM micrograph, taken at 4,900×, of a longitudinal cross section of a prior art smooth luminal surface ePTFE vascular graft. This is FIG. 4C in U.S. Pat. No. 6,517,571 to Brauker et al.;

FIG. 12 is a comparison chart summarizing average characterization of the biocompatible surfaces of a tubular embodiment of the present invention;

FIG. 38 is a schematic representation of extracorporeal blood tubing that incorporates an embodiment of the present invention as the flow surface of the tubing;

FIG. 39 is a cross-section view of an endoluminal balloon that incorporates an embodiment of the present invention as a balloon cover;

FIG. 40 is a top plan view of an endoluminal balloon that incorporates an embodiment of the present invention as an outer surface of the balloon;

DETAILED DESCRIPTION OF EMBODIMENTS OF THE INVENTION

The present invention is directed to a unique biomaterial that may be most preferably utilized as innovative blood contact surfaces in a variety of medical devices. The biomaterial includes microstructures that provide better interaction between a patient's blood and body resulting in improved patient outcomes.

Figure 2:
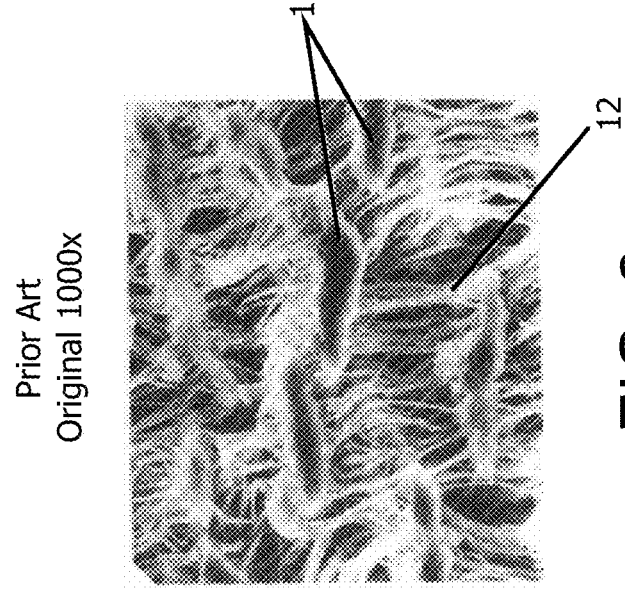
FIG. 2 is a micrograph, taken via a scanning electron microscope (SEM) at 1,000×, showing a node and fibril superstructure characterizing a prior art expanded polytetrafluoroethylene (ePTFE) vessel prosthesis luminal surface. This is FIG. 2 in U.S. Pat. No. 6,436,135 to Goldfarb.
Figure 1:
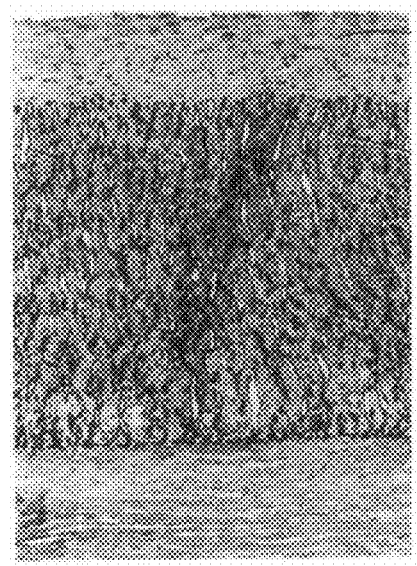
FIG. 1 is a photomicrograph, taken at 250×, of a section of a wall of a prior art vascular graft having been implanted as a femoral artery segment in a canine for a period of eight months. This is FIG. 1 in U.S. Pat. No. 6,436,135 to Goldfarb.

As noted in the Background of the Invention, previous attempts to provide an implantable artificial blood conduit were premised upon a number of theories. FIGS. 1 and 2 are photomicrographs, taken respectively at 250× and 1,000×, of a section of a wall of prior art vascular grafts as illustrated in U.S. Pat. No. 6,436,135 to Goldfarb. The Goldfarb patent describes an expanded polytetrafluoroethylene (ePTFE) vessel prosthesis that employs a microstructure of nodes 10 and fibrils 12. The Goldfarb patent teaches that the average "internodal distance" of the microstructure "must fall within a relatively narrow range of values, viz between approximately 6 and 80 microns." Col. 5, lines 31-34. When the internodal distance is less than 6 micron, Goldfarb teaches that "the node/fibril superstructure is so tightly packed as to preclude either the establishment or continued nutrition of a viable neointima." Col. 5, lines 51-53.

U.S. Pat. No. 6,517,571 to Brauker et al. teaches using a much more tightly packed blood contact structure of 5 micron or less that presents an exceptionally smooth blood interface. FIG. 3 is an SEM photomicrograph, taken at 4,900×, illustrated as FIG. 4C in the Brauker et al. patent. In this SEM Brauker et al. illustrates a microstructure that is highly oriented in one direction, the primary direction of orientation being indicated by arrow 14.

Thus the Goldfarb patent directs one skilled in the art to seek out a microporous structure having an internodal distance of 6 to 80 micron so as to allow cellular ingrowth. Taking a different approach, the Brauker et al. patent teaches using materials with an internodal distance of less than 5 micron, but one that is highly oriented in one direction. As is explained below, the present invention employs a microstructure of less than 5 micron internodal distance that is also balanced in its microstructure. This provides a material that has a large number of pores of very small pore size and which can be both very thin and very strong, making it particularly suitable for use in low profile devices.

DEFINITIONS

The following definitions are used throughout this application:

"Cellular ingrowth," as used herein, defines a condition whereby cells, including but not limited to red blood cells, macrophases, fibroblasts, endothelial cells, etc., infiltrate into the microstructure of a biomaterial such that substantially the entire cell body, including the cellular nucleus, resides within the biomaterial and below its surface.

"Node," as used herein, defines a microscopic mass of polymer material, which may comprise any mass of material from a relatively large conglomeration of polymer to small contacts of material existing at the intersection or termination of two or more fibrils.

"Fibril," as used herein, defines microscopic fibers of polymer material that connect between two or more polymer nodes.

"Balanced" or "biaxially distributed" as used herein, defines a polymer microstructure morphology whereby the internodal distance ("IND") in a first x direction is approximately the same as the IND in a perpendicular y direction, with a preferred ratio of IND in the x and y directions of about 4:1 to 1:1. This is in contrast to the microstructure of the prior art devices shown in FIGS. 1 through 3 whereby the nodes and fibrils exhibit a distinct bias along either the x or y axis of the micrograph. For certain polymer materials, such as expanded fluoropolymers (e.g., ePTFE), balanced microstructure may also reflect approximately equal matrix tensile strengths (MTS) in the x and y directions. When employing a ratio of MTS in the x and y directions to determine a balanced microstructure, again it is preferred that the ratio be about 4:1 to 1:1.

Figure 4:
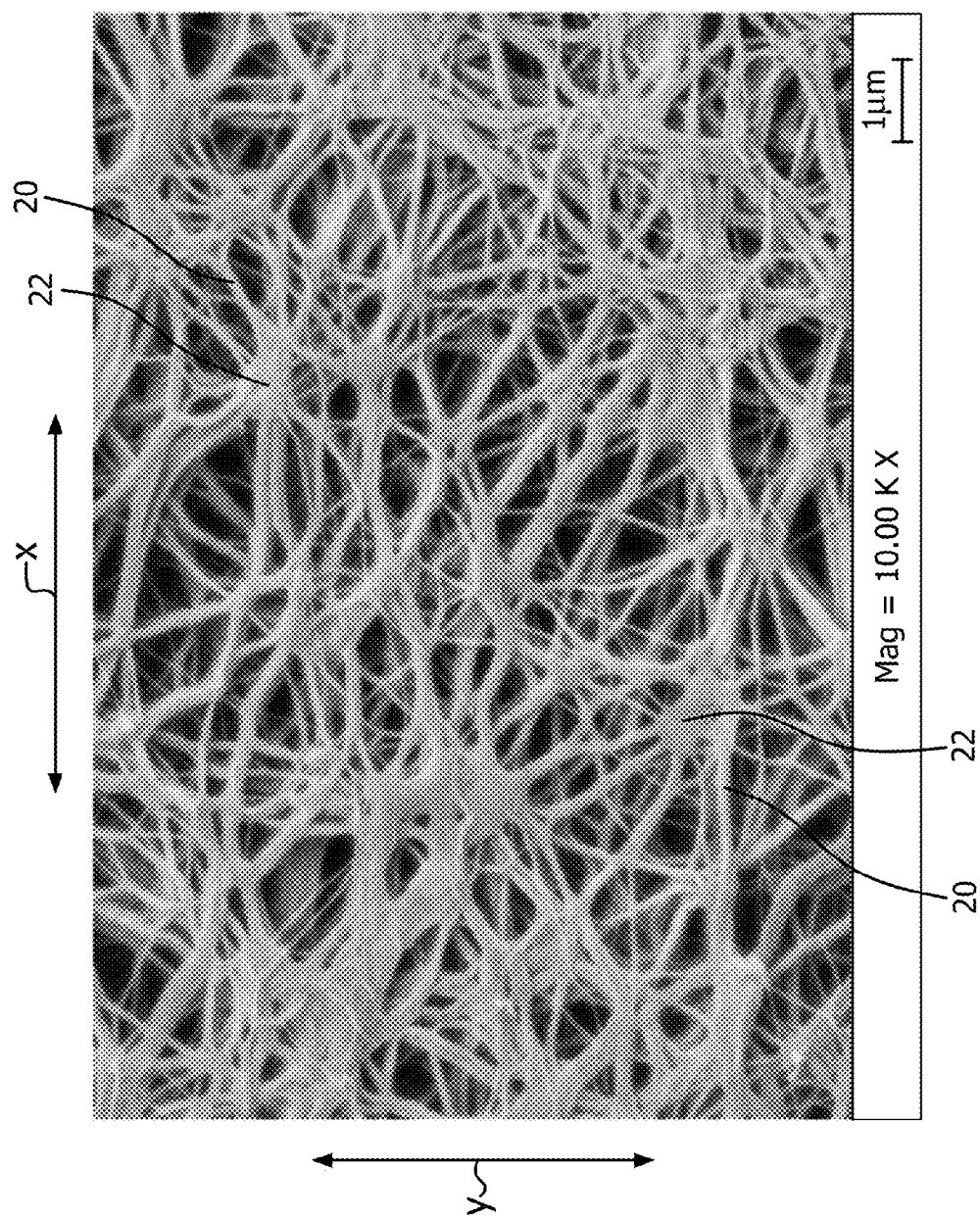
FIG. 4 is an SEM micrograph, taken at 10,000× and including a 1 micron scale bar, showing the microstructure of a biocompatible surface of an embodiment of the present invention.
Figure 5:
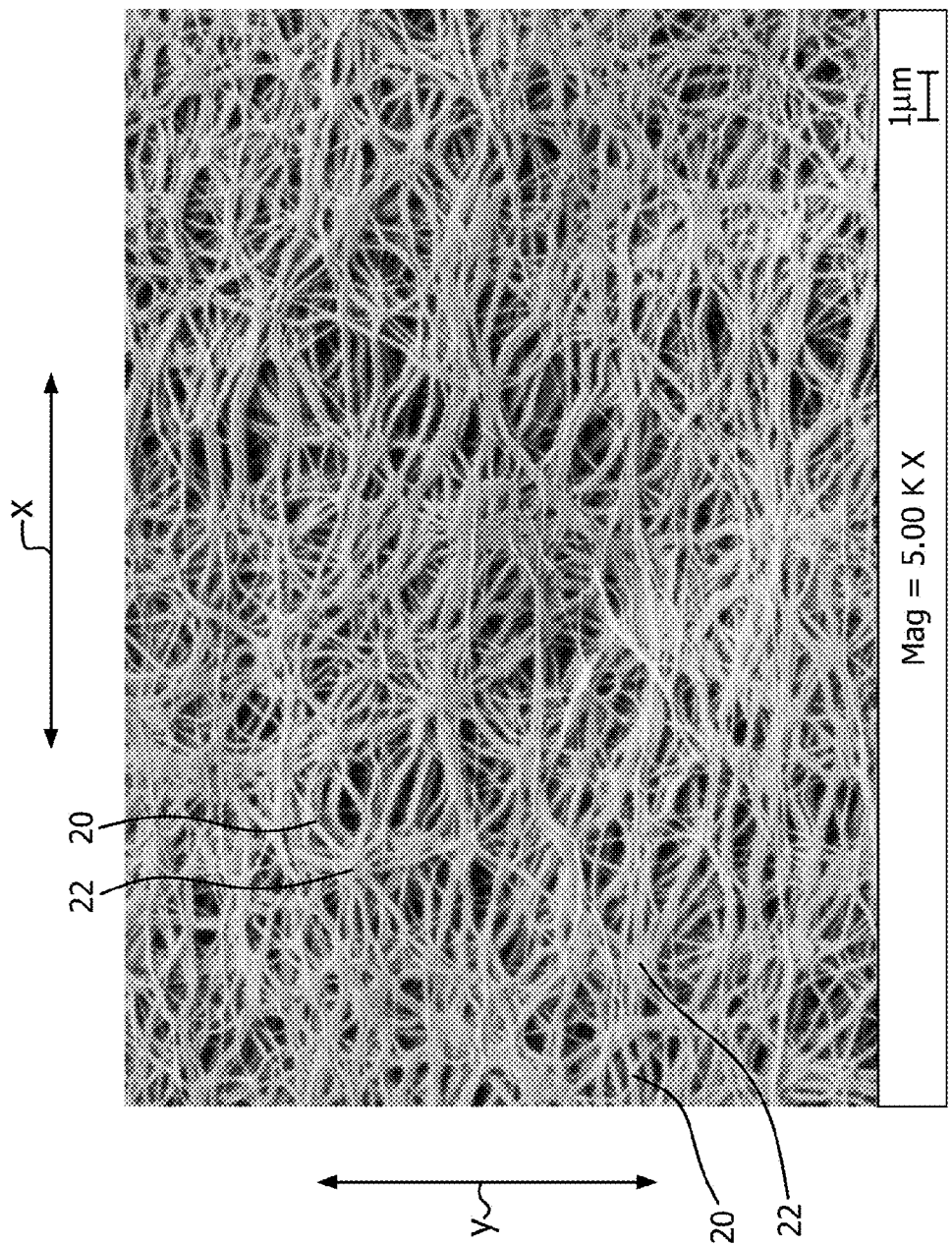
FIG. 5 is an SEM micrograph showing the microstructure of the biocompatible surface of FIG. 4, at a magnification of 5,000× and including a 1 micron scale bar.

The microstructure of a biocompatible surface of an embodiment of the present invention is shown in the SEM micrographs of FIGS. 4 and 5. These micrographs, taken at 10,000× and 5,000×, respectively, and each showing 1 micron scale bars, illustrate a microstructure of short fibrils 20, on the order of 5 micron or less, and relatively small, interconnecting nodes 22.

As can be seen by comparing FIGS. 4 and 5 with the prior art shown in FIGS. 1 through 3, the nodes and fibrils in the inventive materials of FIGS. 4 and 5 have a more balanced orientation in perpendicular directions than the highly asymmetric or aligned node-fibril orientation in the prior art shown in FIGS. 1 through 3.

Figure 6:
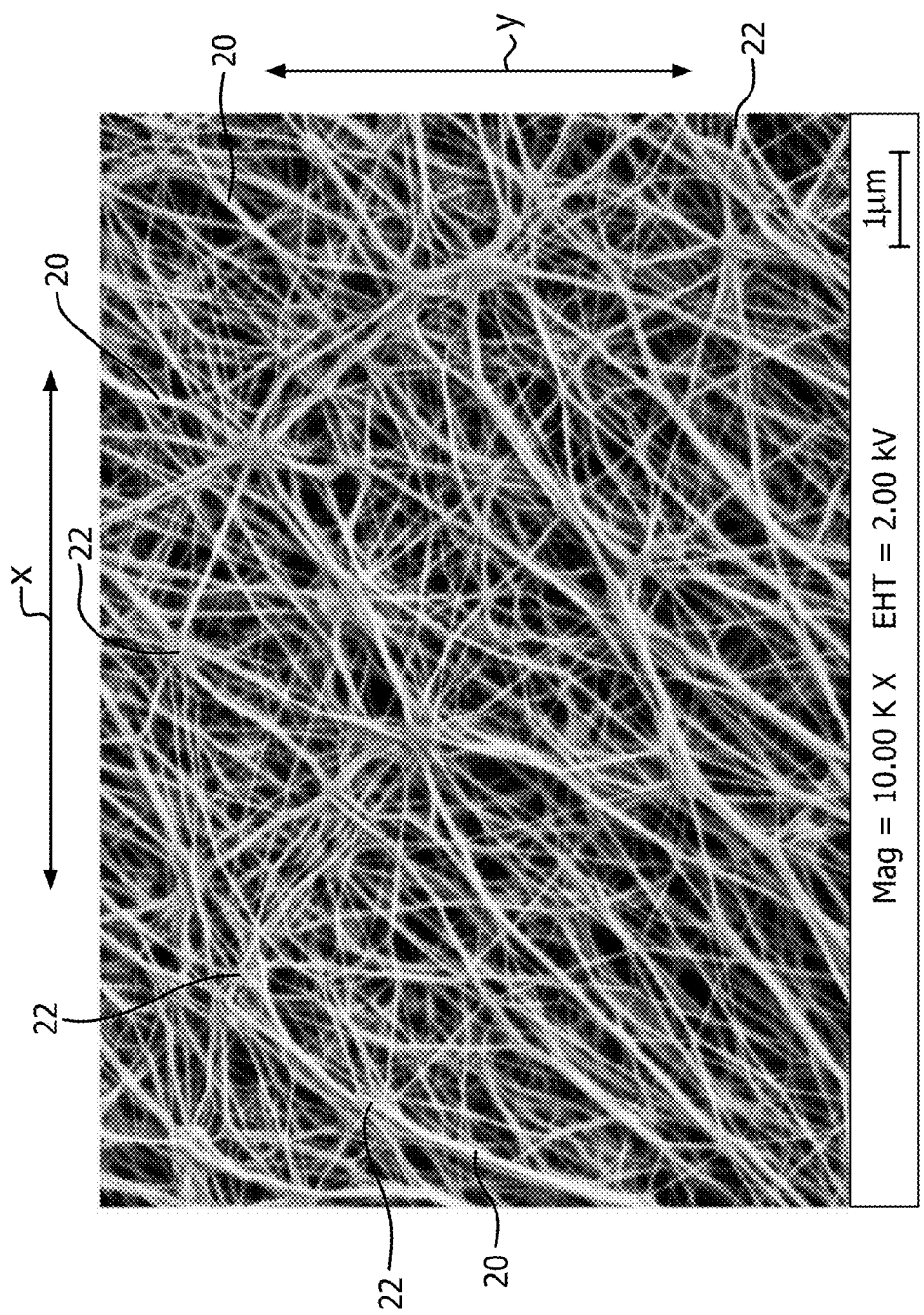
FIG. 6 is an SEM micrograph, taken at 10,000×, showing the microstructure of a biocompatible surface of an embodiment of the present invention.

A further embodiment of the present invention is shown in the SEM micrograph of FIG. 6. This micrograph, also taken at 10,000×, illustrates short fibrils 20 (5 micron or less) with even smaller nodes 22. Again, the microstructure is relatively balanced in perpendicular directions.

As is explained in greater detail below, the present invention employs a synthetic material that presents a suitable microstructure such as that illustrated in FIGS. 5 and 6 and in the other illustrations in the present application. The preferred microstructure is a biocompatible material that does not elicit an excessive adverse foreign body response. Particularly suitable materials include fluoropolymers (such as polytetrafluoroethylene (PTFE), expanded PTFE, fluorinated ethylene propylene (FEP), TFE copolymers, fluoroelastomers (such as TFE/PAVE copolymers, including TFE/PMVE copolymers), etc.), polyethylene (such as ultra-high molecular weight polyethylene (UHMW PE), or polyethylene terephthalate (PET)), etc.), bioabsorbable polymers (such as polylactic acid polymers (PLA), polyglycolic acid polymers (PGA), PGA/trimethylenecarbonate copolymers (PGA/TMC), poly-L-lactides (PLLA), etc.), etc.

It has been demonstrated that an expanded PTFE (ePTFE) microstructure as illustrated in FIGS. 4, 5, and 6 and as described herein provides exceptional blood contact performance. Without intending to limit the present invention to any particular physical characterization of such microstructure, this microstructure may be quantified in a variety of ways, such as by mean internodal distances ("IND"), average fibril thicknesses, average nodal dimensions, relative fibril and nodal dimensions, general orientation of the microstructure, etc. The definitions and details of such characterization methods are described in greater detail below and in the examples included herein.

Figure 7:
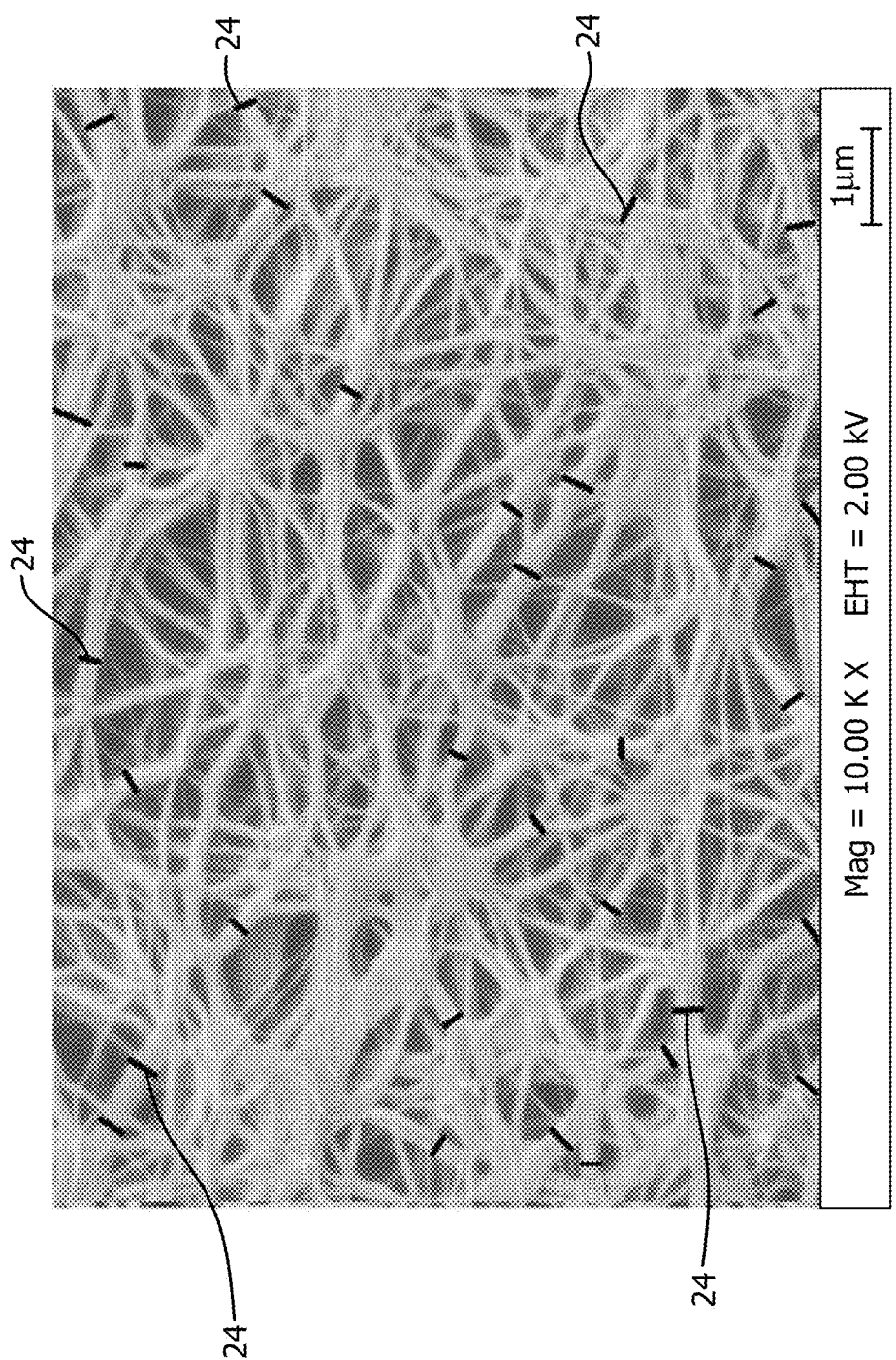
FIG. 7 is the SEM micrograph of FIG. 4 illustrating the identification of 32 thickest fibrils.

As a starting point for characterization of a material used in the present invention, we employed a representative 10,000× enlarged SEM micrograph of biomaterial with approximately a 2000V EHT. From this micrograph, a representative sampling of at least the 30 thickest fibrils is selected. For example, FIG. 7 is the SEM micrograph of FIG. 4 that shows the identification of 32 thickest fibrils (indicated by bars 24) used to characterize the microstructure.

Figure 8A:
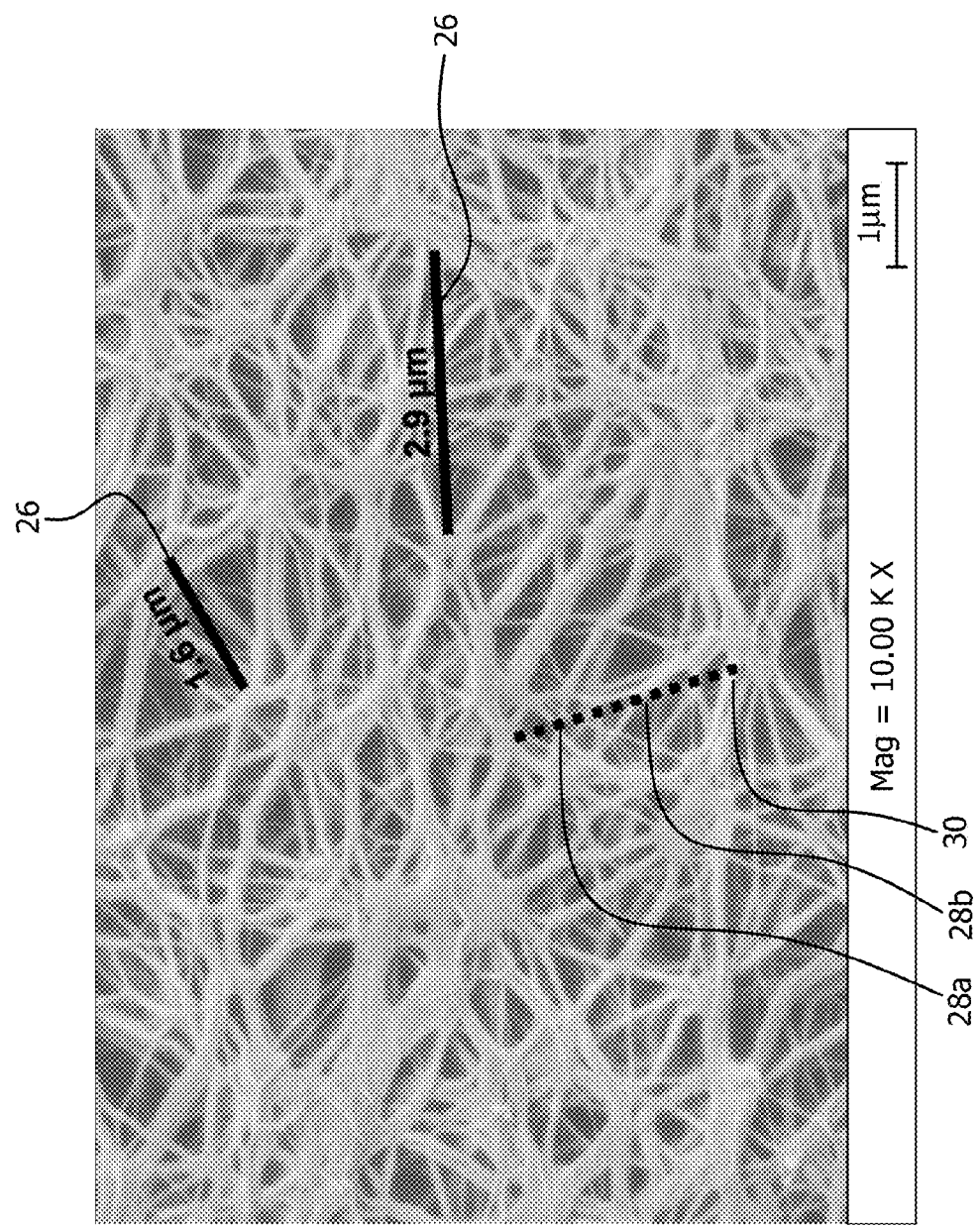
FIG. 8A is the SEM micrograph of FIG. 4 illustrating representative internodal distance measurements between pairs of adjacent nodes.

FIG. 8A shows how to measure IND. First, measurements are taken of the longest distances between 30 or more adjacent nodes in the micrograph, as is shown by representative IND lines 26. The length of the IND is measured from node to node. Thus where a fibril intersects another fibril (creating a nodal point), such as indicated by arrows 28a, 28b along dotted line 30, an IND measurement is not appropriate beyond the point of intersection. For example, in FIG. 8A, measuring the 32 longest INDs, it was determined that the INDs range from 0.94 to 3.80 micron, with a mean IND of about 1.7 micron+/−0.6 micron. Applying similar methodology to the SEM micrograph of FIG. 6, its 32 longest INDs range from 1.39 to 6.41 micron, with a mean IND of about 2.95 micron+/−1.22 micron.

Figure 8B:
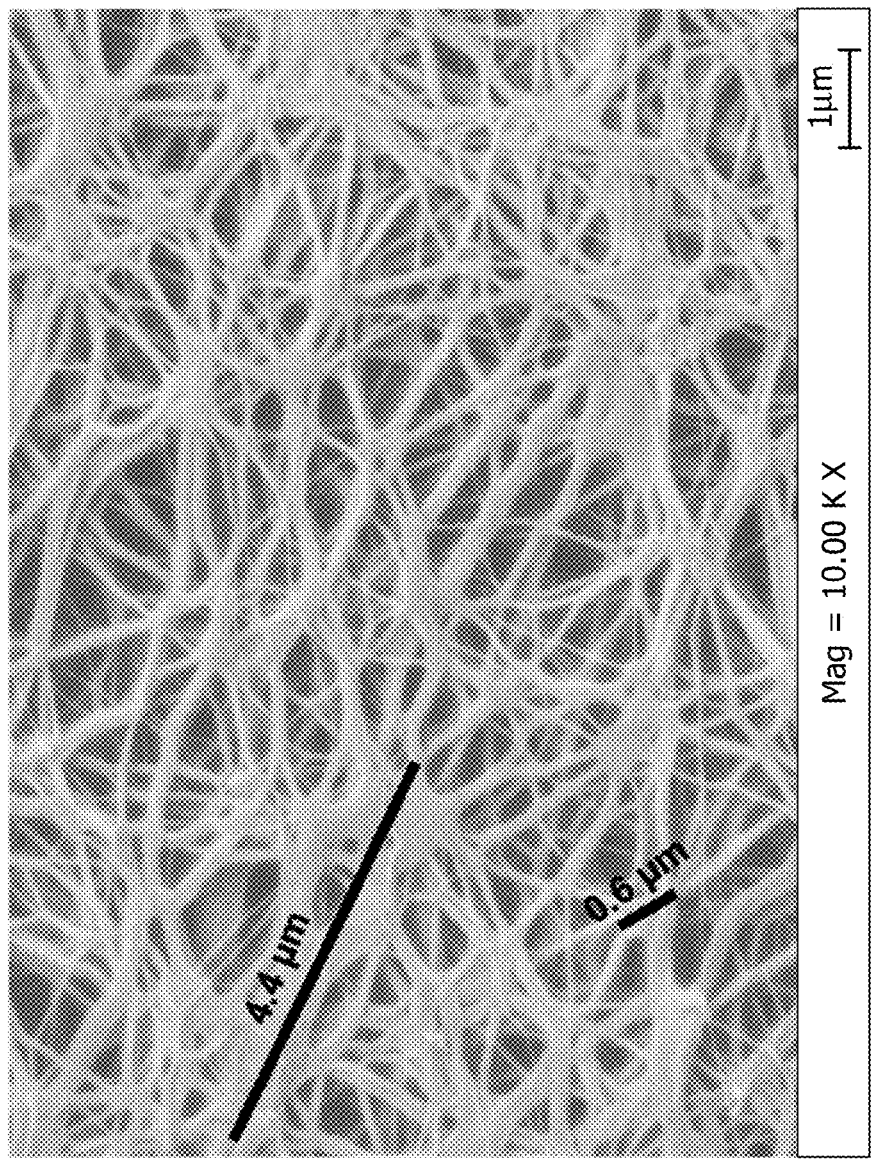
FIG. 8B is the SEM micrograph of FIG. 4 illustrating the measurement of representative nodal widths.
Figure 8C:
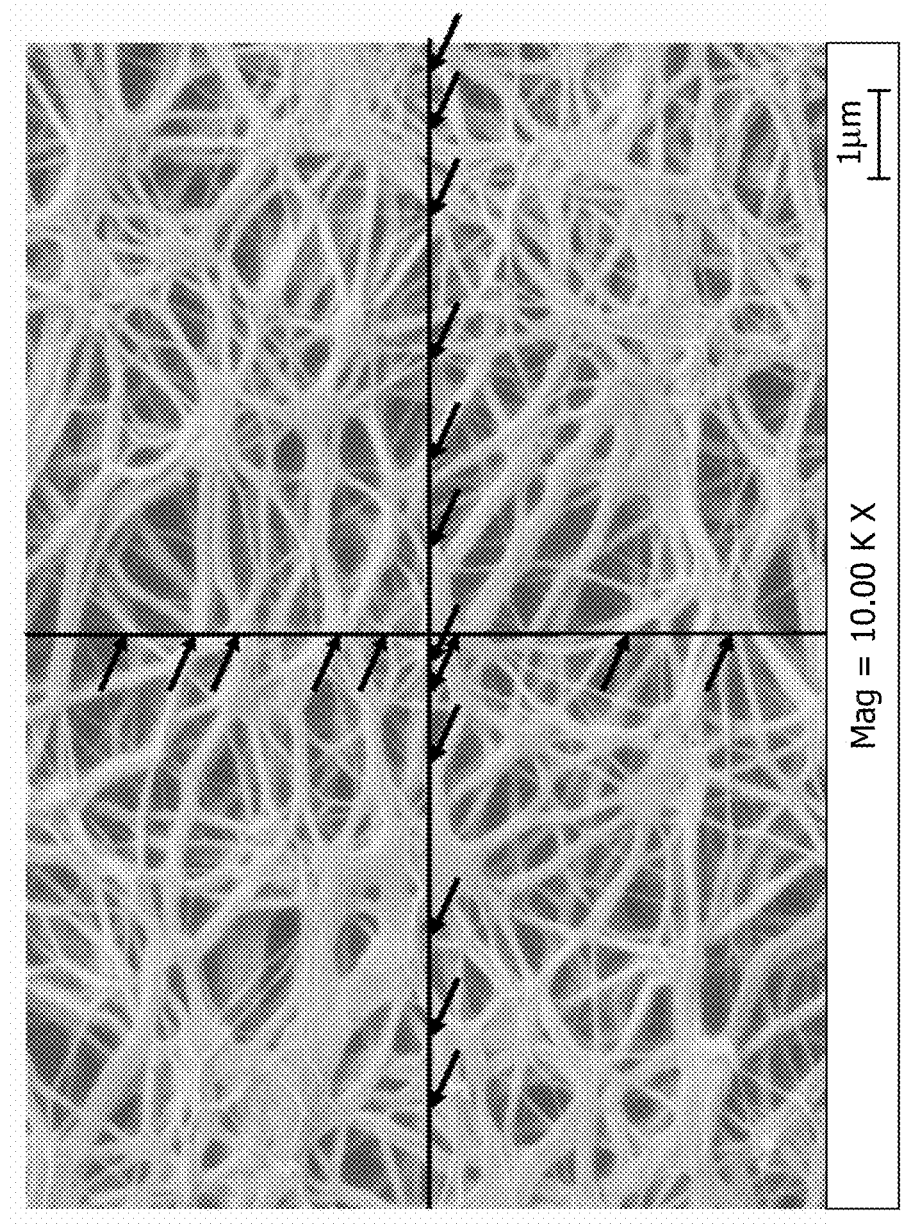
FIGS. 8C and 8D are the SEM micrographs of FIG. 4 illustrating the random selection of nodes for the measurement of internodal distances.
Figure 8D:
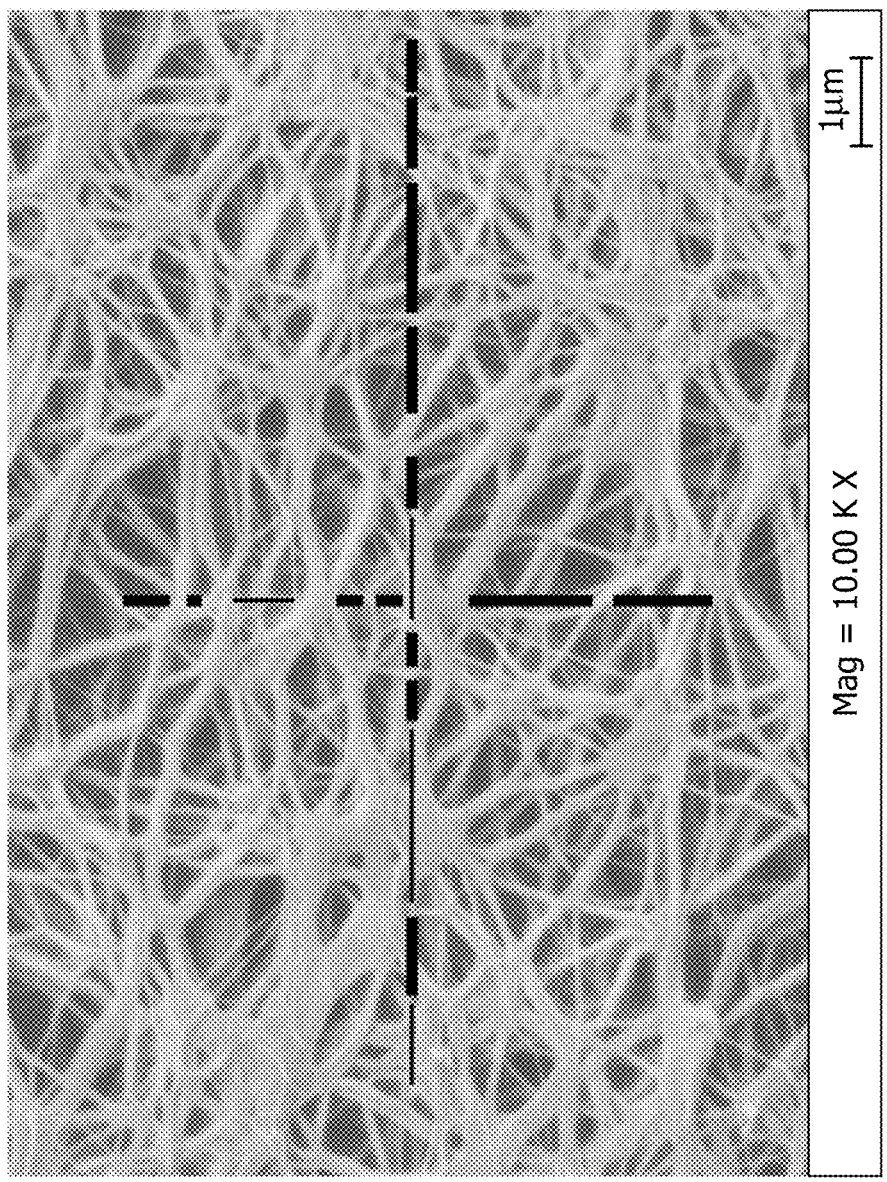

FIGS. 8C and 8D show how to randomly select a set of nodes to determine mean internodal distances in a sample. In this method, as is shown in FIG. 8C, first horizontal and vertical crosshair lines are drawn across the 10,000×SEM micrograph, such as FIG. 4, each at 50% of the image dimensions and extending across the height and width of the image. Each point is marked where a crosshair line crosses a node, as illustrated with arrows in FIG. 8C. As is shown in FIG. 8D, the distances between each such identified node can then be measured by defining the distance from one nodal boundary to the next, as is illustrated in the dark lines of FIG. 8D. Distances along the crosshair lines that are not between two nodes are ignored, as is illustrated by the thin lines in FIG. 8D. Once at least 30 measurements are made in this manner, all internodal distances can then be measured and mean distances determined.

If at least 30 measurements are not collected along the two crosshair lines, then another set of crosshair lines at 10% of the image's width and height are drawn and a second set of internodal distance measurements can be collected. This process can continue, drawing crosshair lines at 10% intervals across the image, until at least 30 measurements are collected.

Using the sampling methods described above with respect to FIGS. 7, 8A, 8C, and 8D, the relative properties of the various inventive biocompatible surfaces described in this application can be defined. These are summarized in the following table:

FIG. 8B illustrates representative measurements of nodal widths whereby the longest dimension of each node in a 10,000×SEM micrograph, such as the micrograph of FIG. 4, is taken. As can be seen, the majority of the nodes in the structure have small nodal widths of well less than 1 micron. However, as shown, occasionally a series of small nodes can coalesce into a structure with significantly larger nodal width of 4 micron or more. Mean nodal widths are determined through the selection of the 32 thickest nodes, as described above with respect to FIG. 7, and measuring the largest dimension of each, or through the crosshair sampling method described above with respect to FIG. 8C.

Figure 9:
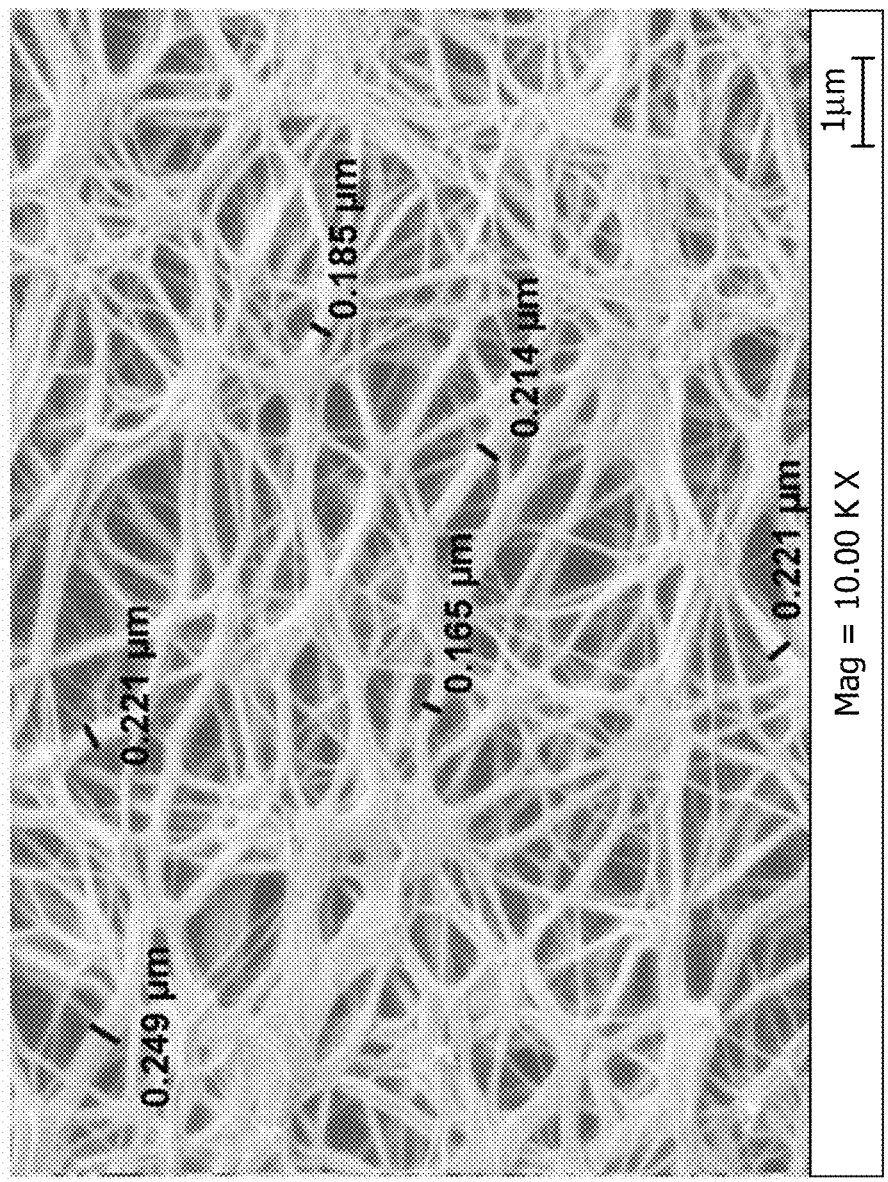
FIG. 9 is the SEM micrograph of FIG. 4 illustrating representative fibril width measurements on six of the fibrils identified in FIG. 7.

From the sampling methods described above in representative micrographs, a number of additional measurements can be performed. In FIG. 9, six representative fibril thickness measurements are shown from the 32 thickest fibrils identified in FIG. 7. Measuring the approximately thickest portions of each of the 32 thickest fibrils, it can be determined that the thickest fibrils range from 0.17 to 0.40 micron in thickness, with an average thickness of about 0.24 micron+/−0.05 micron. Applying similar methodology to the SEM micrograph of FIG. 6, its thickest fibrils range from 0.09 to 0.17 micron in thickness, with an average thickness of about 0.12 micron+/−0.02 micron.

Figure 10:
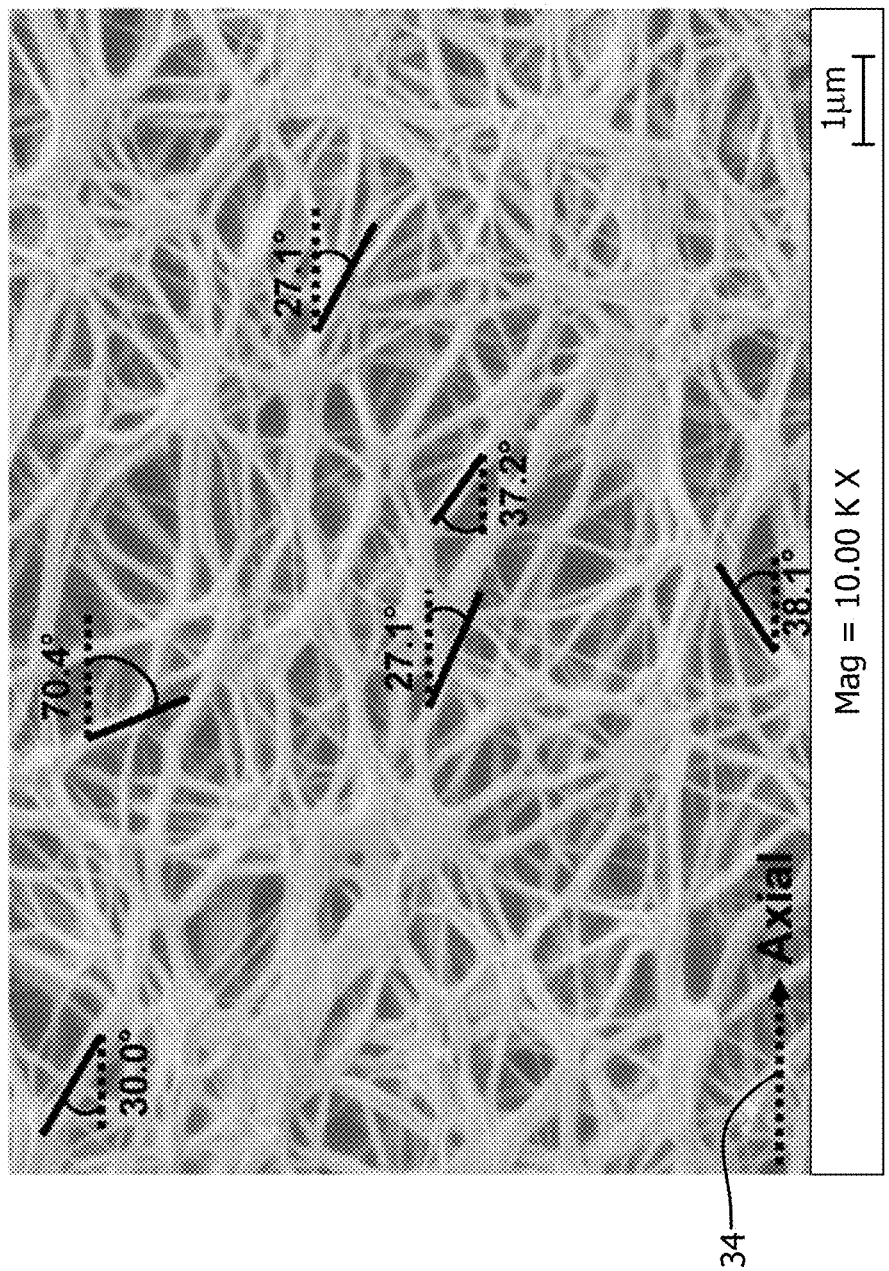
FIG. 10 is the SEM micrograph of FIG. 4 illustrating representative fibril orientation measurements on six of the fibrils identified in FIG. 7.

Again employing the 32 thickest identified fibrils from FIG. 7, in FIG. 10 representative fibril orientations can be determined. In this instance, the degree of variation of each of the 32 fibrils from axial orientation of the device (as described in the example section below and as indicated by horizontal line 34) is determined. Six such measurements are shown in FIG. 10. Measuring each of the 32 thickest fibrils, it can be determined that the degree of orientation from the axial direction ranges from about 4 to 90 degrees, with an average orientation of about 37 degrees+/−20 degrees. Applying similar methodology to the SEM micrograph of FIG. 6, its degree of orientation from axial direction ranges from about 7 to 87 degrees, with an average orientation of about 47 degrees+/−19 degrees. In devices without a clear axial orientation of the device, such as a sheet or patch device, an arbitrary axial direction can be chosen in order to determine fibril orientations in accordance with the present invention.

These and other characterizations of the biomaterials employed in the present invention are described in greater detail below.

FIGS. 13A, 13B, 13C, and 13D are SEM micrographs, each taken at 200×, of four expanded PTFE films used to create biocompatible surfaces of the present invention. At

| Sample | Figure | IND of Largest 32 | | | IND of Random 32 | | | X:Y IND * | Fibril Orientation |
|---|---|---|---|---|---|---|---|---|---|
| | | Mean (μm) | Std Dev (μm) | Range (μm) | Mean (μm) | Std Dev (μm) | Range (μm) | | |
| Prior Art | 11 (2nd column) | 46.7 | 8.6 | 34.2-65.9 | 15.7 | 10.9 | 4.5-44.5 | 0.6 (1.7) | 15.0 |
| Prior Art | 3 | 3.0 | 0.9 | 1.8-5.2 | 0,.8 | 0.7 | 0.2-3.1 | 1.2 | 8.0 |
| Inventive Surface | 6 | 2.6 | 0.7 | 1.4-3.9 | 0.5 | 0.4 | 0.1-1.7 | 1.1 | 47.0 |
| Inventive Surface | 12 (2nd column) | 2.5 | 0.9 | 1.4-5.3 | 0.6 | 0.4 | 0.1-1.9 | 1.0 | 55.0 |
| Inventive Surface | 5 | 1.7 | 0.6 | 0.9-3.8 | 0.9 | 0.9 | 0.1-3.8 | 0.93 (1.1) | 37.0 |
| Inventive Surface | 11 (5th column) | 1.2 | 0.3 | 0.7-1.8 | 0.4 | 0.3 | 0.04-1.1 | 0.6 (1.7) | 58.0 |
| Inventive Surface | 12 (3rd column) | 1.2 | 0.3 | 1.6-1.9 | 0.3 | 0.3 | 0.05-1.2 | 0.9 (1.1) | 57.0 |

* If <1, inverse (i.e., Y:X) indicated in parentheses.

this magnification level, one cannot discern the microstructures of these materials. By contrast, the microstructure of ePTFE materials used in prior art devices, such as the vascular graft shown in FIG. 1, can be discerned at this magnification level. This further illustrates the unique microstructure of the present invention.

Figure 14A:
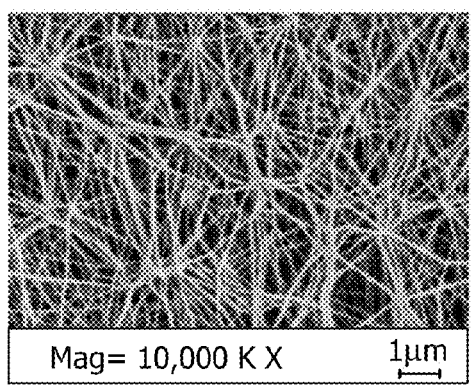
FIGS. 14A, 14B, 14C, and 14D are SEM micrographs, each taken at 10,000×, of the four films in FIGS. 13A, 13B, 13C, and 13D, respectively.
Figure 14B:
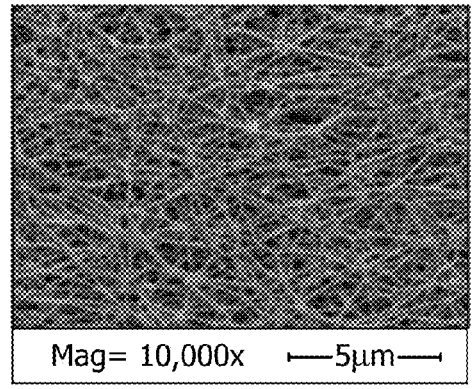
Figure 14C:
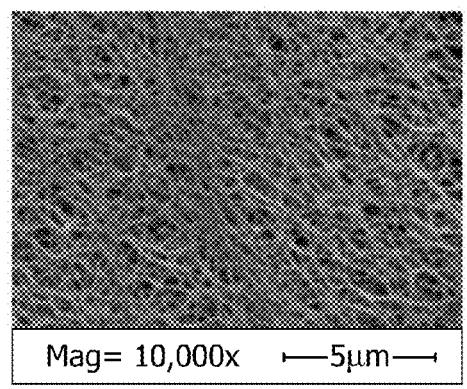
Figure 14D:
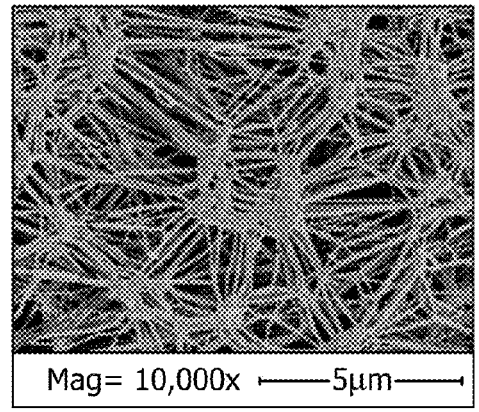

At 10,000×, as shown in FIGS. 14A, 14B, 14C, and 14D, the microstructures of each of these four biocompatible surfaces of the present invention can be clearly seen and distinguished. While each of these microstructures is distinguished by its own specific form, they all share a number of characteristics, including having very short INDs, being relatively similar in internodal distances in x and y directions (that is, being morphologically "balanced"), and having relatively small nodes relative to fibril length. In fact, the microstructures of FIGS. 14A, 14B, and 14C present extremely small nodes, whereby the nodes are essentially nodal points at the intersection of fibrils.

The creation and testing of these variations of the present invention are explained in the Examples set forth below.

Expanded PTFE materials used in the present invention have general and preferred ranges of properties that are summarized in the tables below:

|  | General Range | Preferred Range |
|---|---|---|
| ePTFE tube or film for use in creating inventive biocompatible surface |  |  |
| Thickness | 0.0001 to 0.1 mm | 0.001 to 0.05 mm |
| Mass Per Area | 0.1 to 40 g/m2 | 0.3 to 20 g/m2 |
| Surface Area/Mass | 10 to 50 m2/g (>10, m2/g) | 15 to 35 m2/g (>15 m2/g) |
| Bubble point | 200 to 1500 kPa | 350 to 700 kPa |
| Air Flow | 0.01 to 30 Frazier | 0.1 to 10 Frazier |
| Matrix Tensile Strength (MTS) in at Least One Direction | 150 to 700 MPa | 350 to 600 MPa |
| MTS Balance Ratio | 4:1 to 1:1 | 1.5:1 to 1:1 |
| Mean Internodal Distance | 0.001 to 5 μm | 1 to 5 μm, and more preferably 1 to 3 μm |
| Fibril Width | 0.02 to 0.3 μm | 0.05 to 0.2 μm |
| Nodal Width | 0.1 to 1.5 μm | 0.2 to 1.0 μm |
| Fibril Orientation | 20 to 70° | 30 to 60° |
| Film tube providing a biocompatible surface of the present invention |  |  |
| Wall thickness | 0.001 to 5 mm | 0.02-1.3 mm |
| Inner Diameter (ID) Internodal distance | 0.001 to 5 μm | 1 to 5 μm, and more preferably 1 to 3 μm |
| ID Fibril width | 0.02 to 0.3 μm | 0.05 to 0.2 μm |
| Strength Balance Ratio | 4:1 to 1:1 | 1.5:1 to 1:1 |
| Nodal width | 0.1 to 1.5 μm | 0.2 to 1.0 μm |
| ID Fibril Orientation | 20 to 70° | 30 to 60° |

Figure 11:
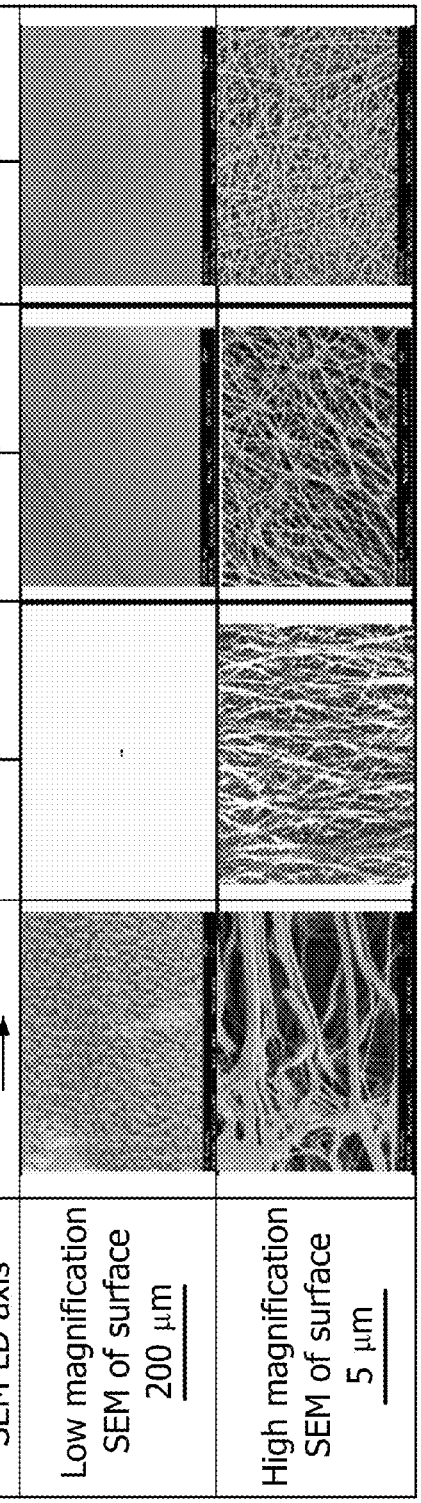
FIG. 11 is a comparison chart summarizing average characterization distinctions between polymer biomaterials used to create prior art biocompatible surfaces and films used in embodiments of the present invention.
Figure 13A:
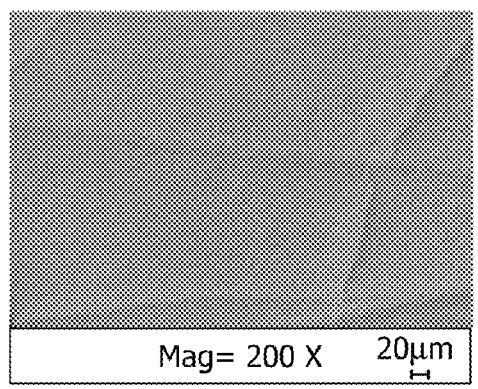
FIGS. 13A, 13B, 13C, and 13D are SEM micrographs, each taken at 200×, of four films having biocompatible surfaces of embodiments of the present invention.
Figure 13B:
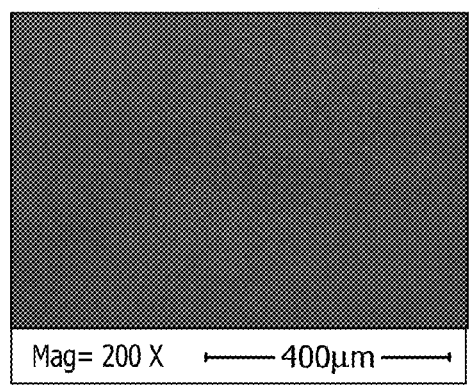
Figure 13C:
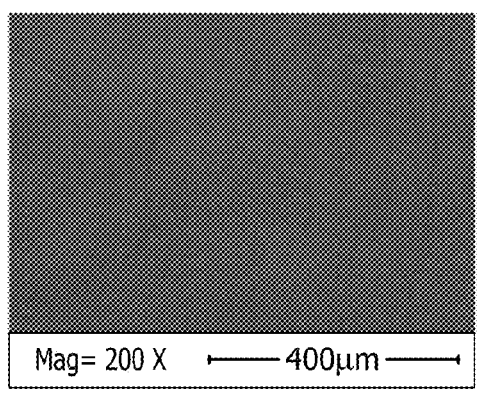
Figure 13D:
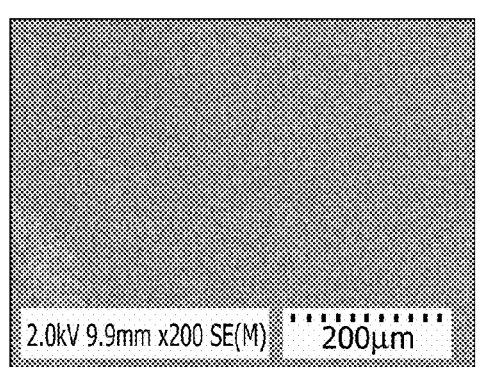

In order to demonstrate the functionality of the biocompatible surface of the present invention, a study was conducted whereby an endoluminal stent-graft control device (comprising a nitinol metal frame attached to an ePTFE graft) and employing a covalently bonded heparin coating, commercially available under the trademark GORE VIABAHN® from W.L. Gore & Associates, Inc., was implanted in the carotid artery of a canine for a period of 60 days. This commercial product is characterized by a microstructure with a mean IND of about 47 micron and a microstructure that is predominantly expanded in only one axis (asymmetrically orientated). In this respect, the inventive biocompatible surface of the device resembles the microstructure shown in column 2 (headed "Highly oriented, extruded expanded tube for ID") of FIG. 11 in the present application.

Similarly, a vascular stent-graft embodiment of the present invention made in accordance with Example 3 below, and also including a covalently bonded heparin coating, was implanted in a canine carotid artery under identical conditions and for the same duration. The microstructure of this device is characterized by a mean IND of about 1.7 micron, and a microstructure that is essentially balanced in its x and y directions. This biocompatible surface is similar to the microstructure shown in FIGS. 4 and 5 in the present application.

Figure 15:
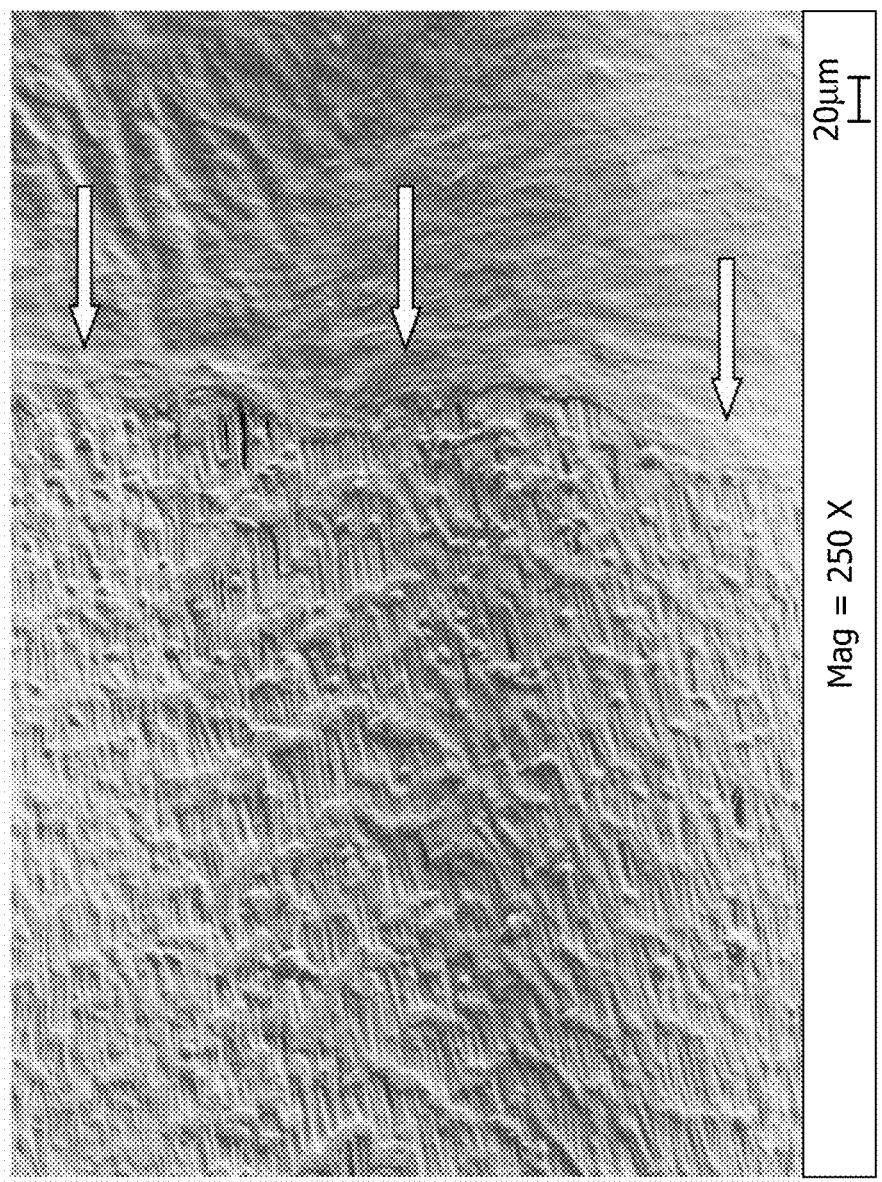
FIG. 15 is an SEM micrograph, taken at 250×, of a luminal surface of an expanded polytetrafluoroethylene (ePTFE) control device, showing ePTFE node and fibril structure on the left side of the micrograph overlaid with scattered cells and a thin film of protein which fills interfibril spaces. Block arrows identify confluent cellular tissue which overlies the surface at right.
Figure 16:
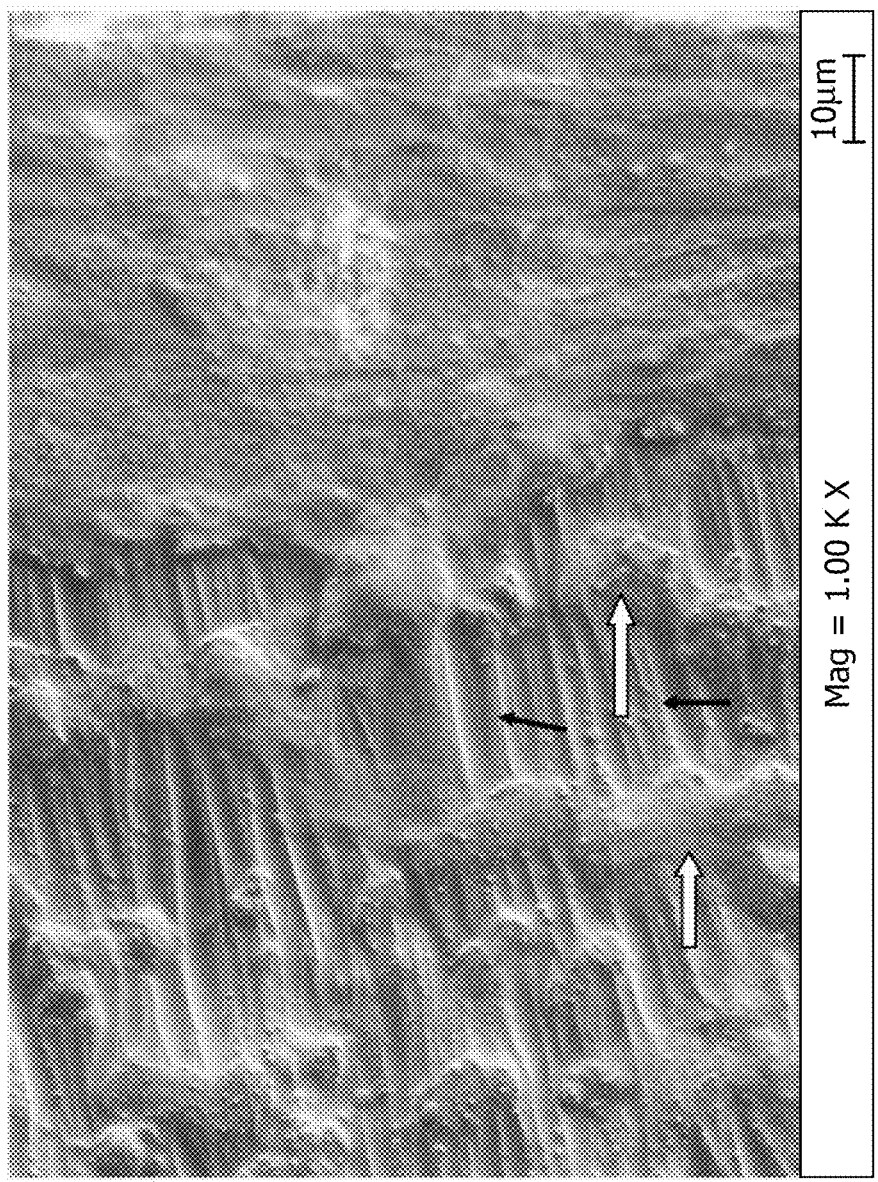
FIG. 16 is an SEM micrograph, taken at 1,000×, of a luminal surface of an ePTFE control device, showing ePTFE node and fibril structure, with the block arrows identifying representative ePTFE nodes and line arrows identifying representative fibrils interconnecting the nodes. Confluent cellular tissue overlies the surface at the right.
Figure 17:
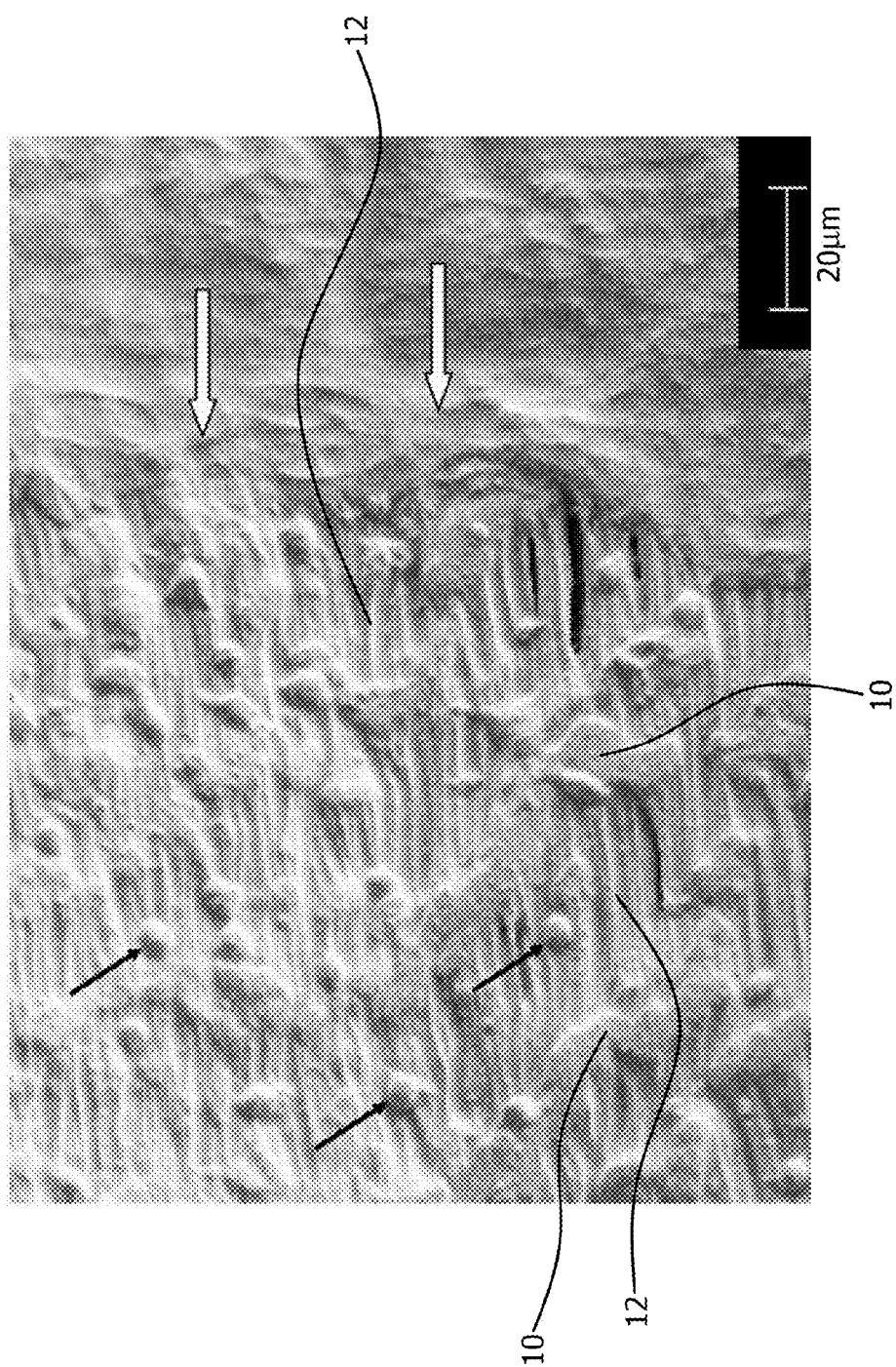
FIG. 17 is an SEM micrograph, taken at 667×, of the luminal surface of an ePTFE control device, showing ePTFE node and fibril structure. Block arrows on the right of the micrograph identify confluent cellular tissue overlying the ePTFE biomaterial surface. The morphology of the ePTFE biomaterial is shown on the left side largely filled with protein but with some visible empty interfibril spaces. Line arrows identify cells overlying the surface of the ePTFE.
Figure 18:
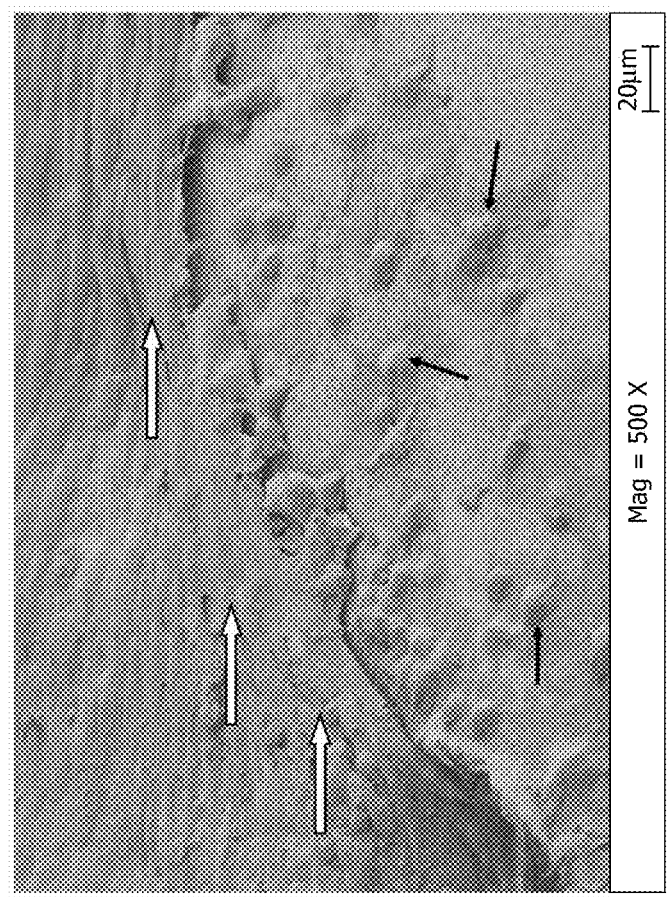
FIG. 18 is an SEM micrograph, taken at 500×, of a luminal surface of an embodiment of the present invention, with block arrows identifying representative confluent cellular tissue overlying the ePTFE biomaterial surface on the left, and with line arrows identifying representative individual cells of similar nuclear morphology overlying the biomaterial surface on the right.
Figure 19:
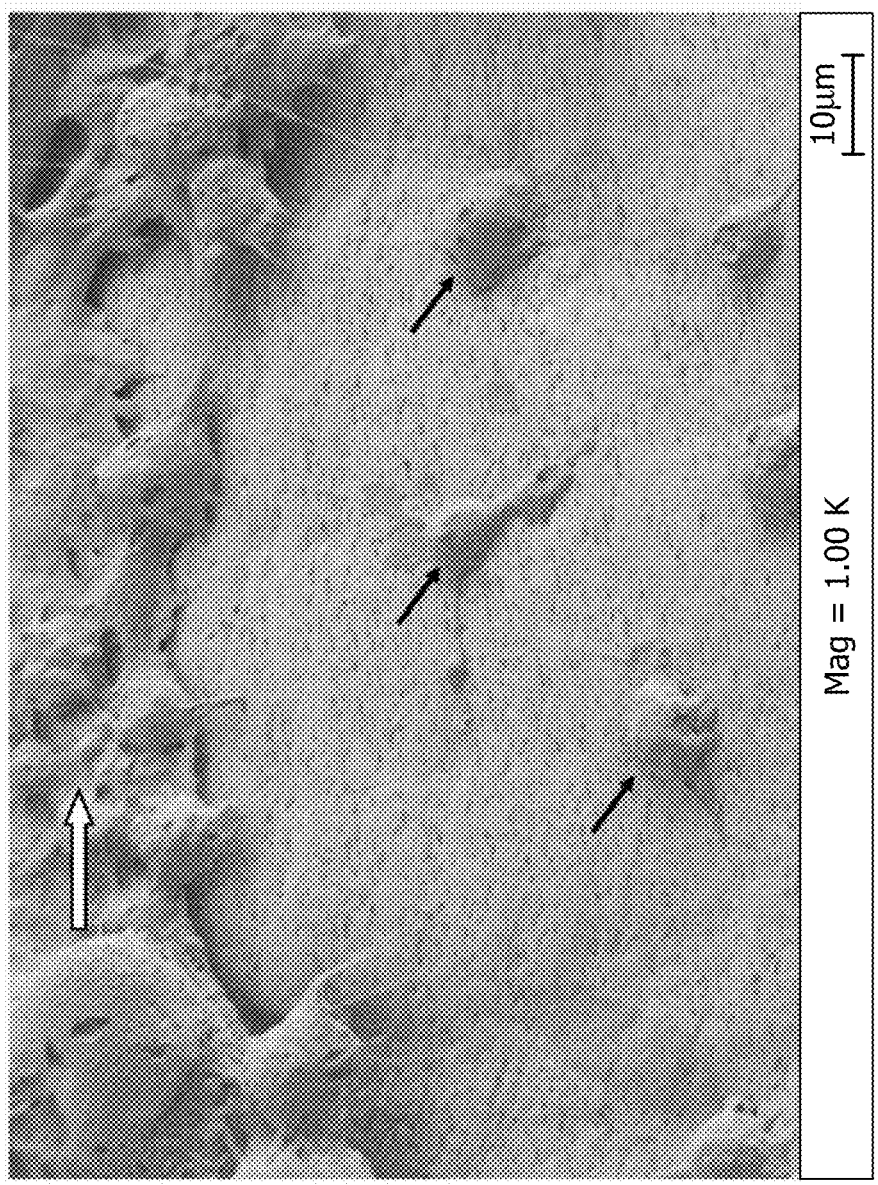
FIG. 19 is an SEM micrograph, taken at 1,000×, of a luminal surface of an inventive test device, with a block arrow identifying representative confluent cellular tissue overlying the biomaterial surface at the top of the image, and line arrows identifying representative individual cells of similar nuclear morphology overlying the surface at the bottom of the image. There are no interfibril spaces identified that would allow infiltration of cell nuclei.
Figure 20:
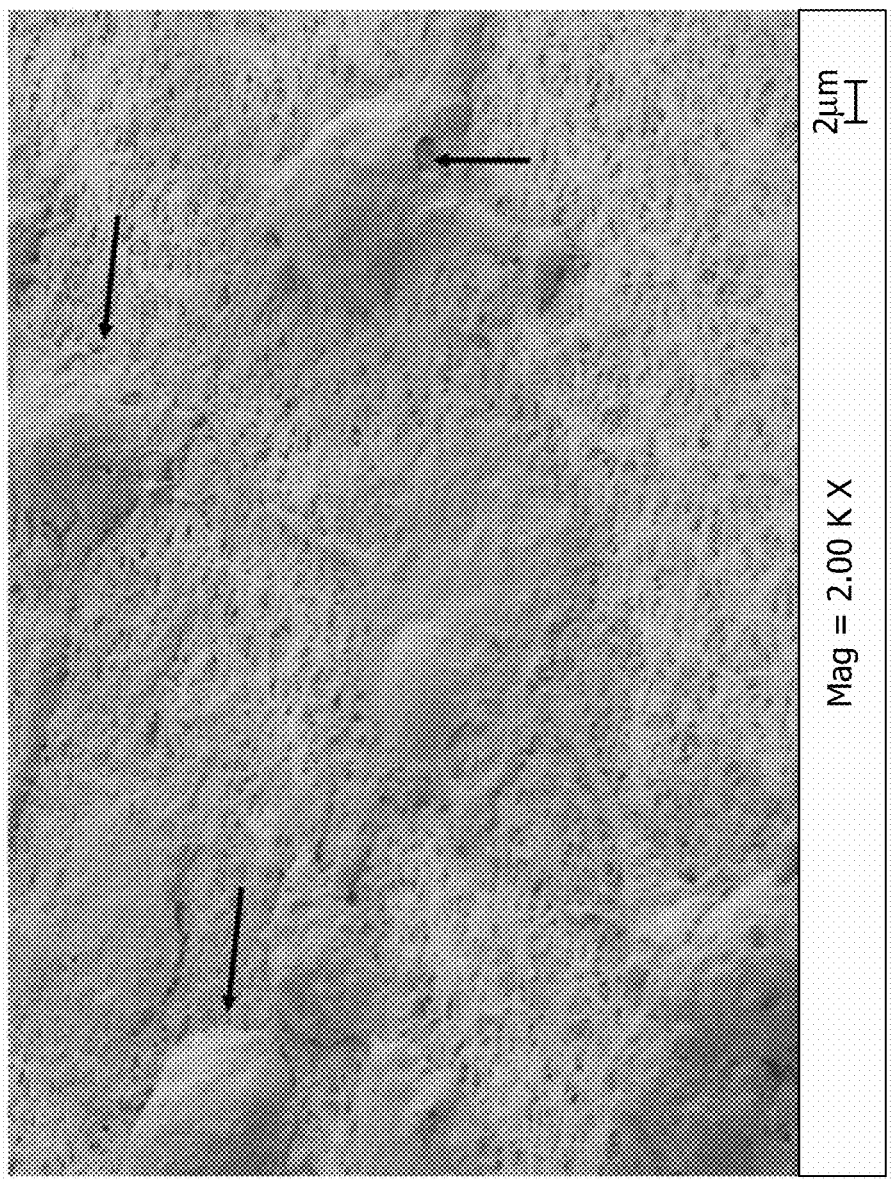
FIG. 20 is an SEM micrograph, taken at 2,000×, of a luminal surface of an embodiment of the present invention, with the line arrows identifying representative individual cells of similar morphology overlying the biomaterial surface. There are no interfibril spaces that would allow infiltration of cell nuclei.

After 60 days of implantation, each of these devices was harvested and examined under SEM. The commercial control device functioned consistent with historical performance, demonstrating no negative foreign body response and showing initial signs of typical endothelialization of the blood contact surface, as is shown in FIGS. 15, 16, and 17. Likewise, the inventive stent-graft demonstrated very similar foreign body and cellular response, as is shown in FIGS. 18, 19, and 20. This is remarkable since the microstructure of the inventive stent-graft comprises a much tighter microstructure than the one in the control device. Since these small pores prohibit ingrowth of the cell nuclei directly, the endothelial cells apparently responded to the inventive blood contact surface in a manner very similar to an endothelial cell response to a natural fibrin substrate.

FIG. 15 is an SEM micrograph, taken at 250×, of the luminal surface of the commercial control device implanted in a canine carotid artery for 60 days, showing ePTFE node and fibril structure on the left side of the micrograph overlaid with scattered cells and protein which fills interfibrillar spaces. Block arrows on the right of the micrograph identify confluent cellular tissue that overlies the surface.

FIG. 16 is an SEM micrograph, taken at 1,000×, of the luminal surface of the control device, showing ePTFE node and fibril structure, with the block arrows identifying representative ePTFE nodes. The line arrows identify representative fibrils interconnecting the nodes. Again, confluent cellular tissue overlies the surface at the right.

FIG. 17 is an SEM micrograph, taken at 667×, of the luminal surface of the control device, showing ePTFE node 10 and fibril 12 structure. Block arrows on the right of the micrograph identify confluent cellular tissue overlying the ePTFE biomaterial surface. The morphology of the ePTFE biomaterial is shown on the left side largely filled with protein but with some visible empty interfibrillar spaces. Line arrows identify cells overlying the surface of the ePTFE. Note the small size of the cells relative to the large distances between nodes in the microstructure of the control device luminal surface.

By contrast, FIG. 18 is an SEM micrograph, taken at 500×, of a luminal surface of an inventive test device implanted in a canine carotid artery for 60 days. The block arrows identify representative confluent cellular tissue overlying the biomaterial surface on the left of the image. On the lower right of the image, endothelial cells can be seen spread-out and attached to the tight microstructure of the inventive blood contact surface, consistent with a migratory phenotype. Line arrows identify representative individual cells of similar nuclear morphology overlying the base inventive biomaterial surface.

FIG. 19 is an SEM micrograph, taken at 1,000×, of a luminal surface of the inventive test device. Again, the block arrow identifies confluent cellular tissue overlying the polymer biomaterial surface at the top of the image, and line arrows identify representative individual cells of similar nuclear morphology overlying the surface at the bottom of the image. Due to the tight microstructure of the inventive biomaterial, there are no interfibrillar spaces identified that would allow infiltration of cell nuclei.

FIG. 20 is an SEM micrograph, taken at 2,000×, of a luminal surface of the inventive test device, with the line arrows identifying representative individual cells of similar morphology overlying the biomaterial surface. As can be seen, the cells appear to have readily attached directly to the underlying inventive biomaterial. Note again that the cells are spread-out with bi-directional orientation of the cells, and long filamentous projections attached to the prosthetic surface. This is consistent with a migratory phenotype. No evidence of rounded cells with non-polar orientation is seen. Further, there are no interfibrillar spaces that would allow infiltration of cell nuclei.

As the terms "intimate" or "intimately" are employed with regard to cell attachment to the biomaterial of the present invention, they are intended to convey that, under a micrograph of 2,000× or less, the cells appear to be attaching closely to the underlying biomaterial without the body first applying a visible intervening layer of other materials to the substrate biomaterial, such as other cells, fibrin, etc. It is suspected that the body may be applying other materials to the substrate biomaterial to facilitate cell attachment, such as various proteins and the like at a molecular level, but unlike larger intervening materials that are typically found on existing artificial blood contact surfaces prior to successful endothelialization, such as fibrin, these are not readily distinguishable under micrographs of this magnification (that is, 500 to 2000×). It should be noted that the role of a covalently bonded heparin component used in conjunction with the inventive microstructure in facilitating endothelial cell attachment and migration is not yet known.

Figure 21A:
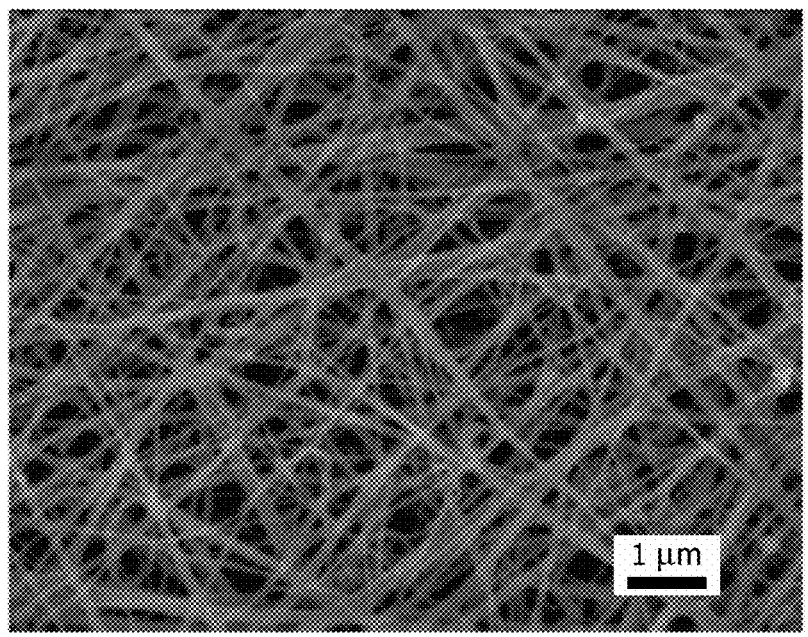
FIG. 21A is an SEM micrograph, shown with a scale bar of 1.0 micron, of a natural fibrin mat that may be found on the luminal (flow) surface of a human artery, as published in Pretorius, et al., "Comparative Scanning Electron Microscopy of Platelets and Fibrin Networks of Human and Different Animals," *Int. J. Morphol.* [online], 2009, Vol. 27, n.1, pp 69-76, ISSN 0717-9502.

It is interesting to note that there is some similarity in morphology between the inventive surface of the present invention and natural fibrin surfaces occurring in a mammalian body that may foster attachment of endothelial cells. FIG. 21A shows a natural fibrin mat that may be found on the luminal (flow) surface of a human artery, as published in Pretorius, et al., "Comparative Scanning Electron Microscopy of Platelets and Fibrin Networks of Human and Different Animals," *Int. J. Morphol. [online]*, 2009, vol. 27, n.1, pp. 69-76, ISSN 0717-9502. This fibrin presents a morphology of essentially short fibrils, with an internodal distance on the order of less than 5 micron, intersecting at what is essentially small nodal points. Moreover, the microstructure is essentially balanced in the x and y directions. The width of the fibrin fibrils is reported to be in the range of 23 to 441 nm.

Figure 21B:
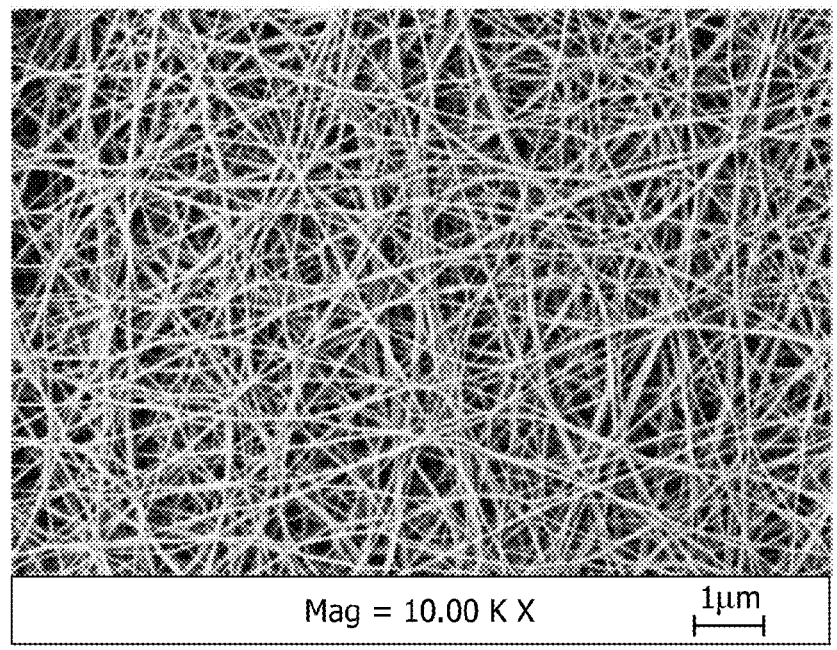
FIG. 21B is an SEM micrograph, taken at 10,000× and including a 1.0 micron scale bar, showing the microstructure of a biocompatible surface of the present invention produced in accordance with Example 2 of the present application.

The biocompatible surface of the present invention is shown under similar magnification in the micrograph of FIG. 21B. As can be seen, the artificial microstructure of the present invention presents a morphology remarkably similar to that of natural fibrin, including having short fibrils (with a less than 5 micron internodal distance), fibrils intersecting at small nodal points, and the microstructure being approximately balanced in the x and y directions. These fibrils have a width in the range of 90 to 320 nm.

Figure 22:
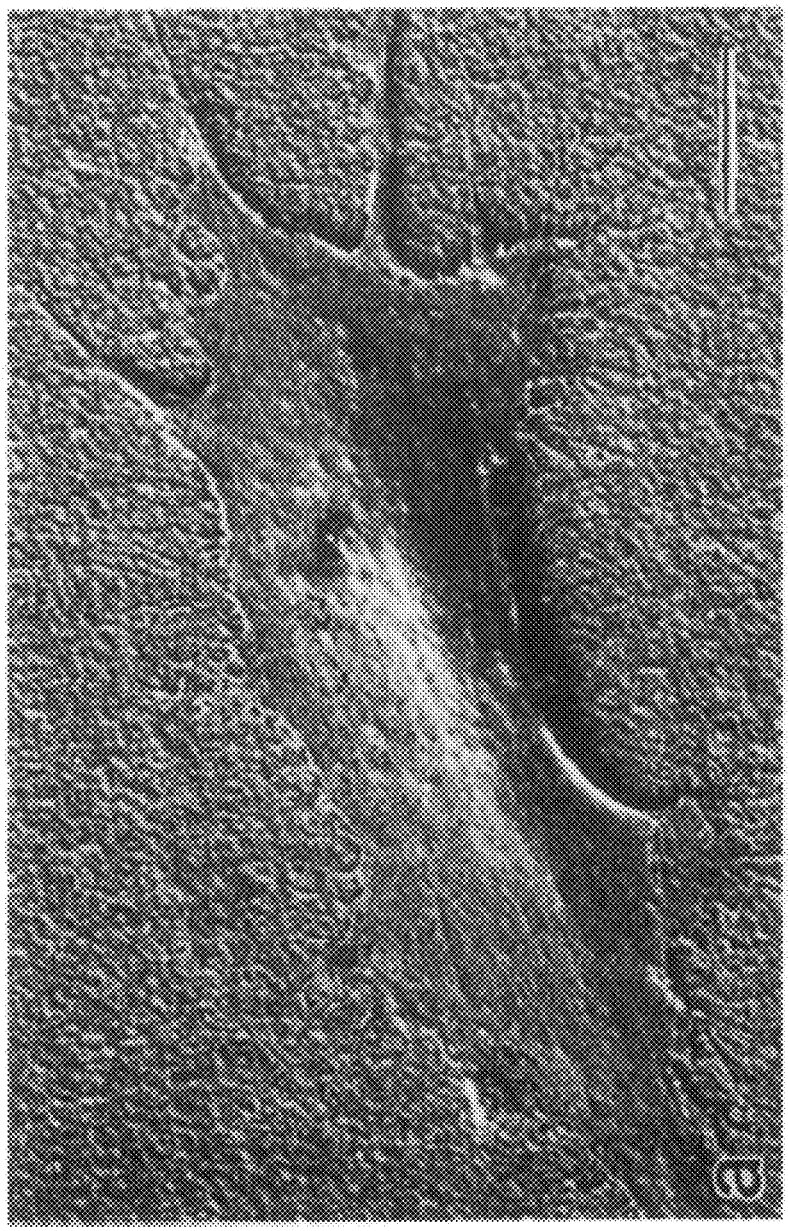
FIG. 22 is an SEM micrograph, taken at 2,000× and displaying a 10 micron scale bar, showing an endothelial cell attached to a natural thrombin-made fibrin mat, and further showing bidirectional orientation of the cell with long filamentous projections and fibrillar background, as reported in Brunce, et al., "Endothelial Cell Spreading on Fibrin Requires Fibrinopeptide B Cleavage and Amno Acid Residues 15-42 of the β Chain," *J. Clin. Invest.*, March 1992, Vol. 89, pp 842-850.

It is further of interest that the relative cellular responses achieved with the present invention also reflect desirable endothelial cell responses reported in the literature. FIG. 22 is an SEM micrograph, taken at 2,000×, showing an endothelial cell attached to a natural thrombin-made fibrin mat as reported in Brunce, et al., "Endothelial Cell Spreading on Fibrin Requires Fibrinopeptide B Cleavage and Amno Acid Residues 15-42 of the β Chain," March 1992, vol. 89, *J. Clin. Invest., pp.* 842-850. This micrograph is identified by the authors as representing a desirable endothelial cell attachment, with the cell showing bidirectional orientation and long filamentous projections attaching to a fibrillar background. As can be seen, this cell's morphology is similar to the cellular attachment to the inventive material shown in FIGS. 18 through 20.

Figure 23:
FIG. 23 is a cross section view of a light microscope histology image, displaying a 50 micron bar and stained with hematoxylin and eosin (H&E), of a control ePTFE vascular graft device wall, showing a flow lumen at the top of the image. Block arrows indicate representative cellular fibromuscular neointima overlying and infiltrating luminal graft biomaterial. Line arrows indicate cell nuclei, erythrocytes and protein within interstices of the ePTFE biomaterial.

FIG. 23 shows the cross-section of a wall from a conventional expanded polytetrafluorethylene (ePTFE) vascular stent-graft with covalently bonded heparin as commercially available under the trademark GORE VIABAHN® from W.L. Gore & Associates, Inc., that was implanted in the carotid artery of a canine for a period of 60 days. This commercial product is characterized by a microstructure with an average fibril length of about 47 micron, and a microstructure that is predominantly expanded in only one axis. In this respect, the blood contact surface of the device resembles the microstructure shown in column 2 (headed "Highly Oriented, Extruded Tube for ID") of FIG. 11 in the present application.

FIG. 23 shows tissue contacting the flow lumen oriented at the top of the figure. Block arrows indicate representative cellular fibromuscular neointima overlying and infiltrating luminal graft biomaterial. Line arrows indicate cell nuclei, erythrocytes and protein within the interstices of the ePTFE material.

Figure 24:
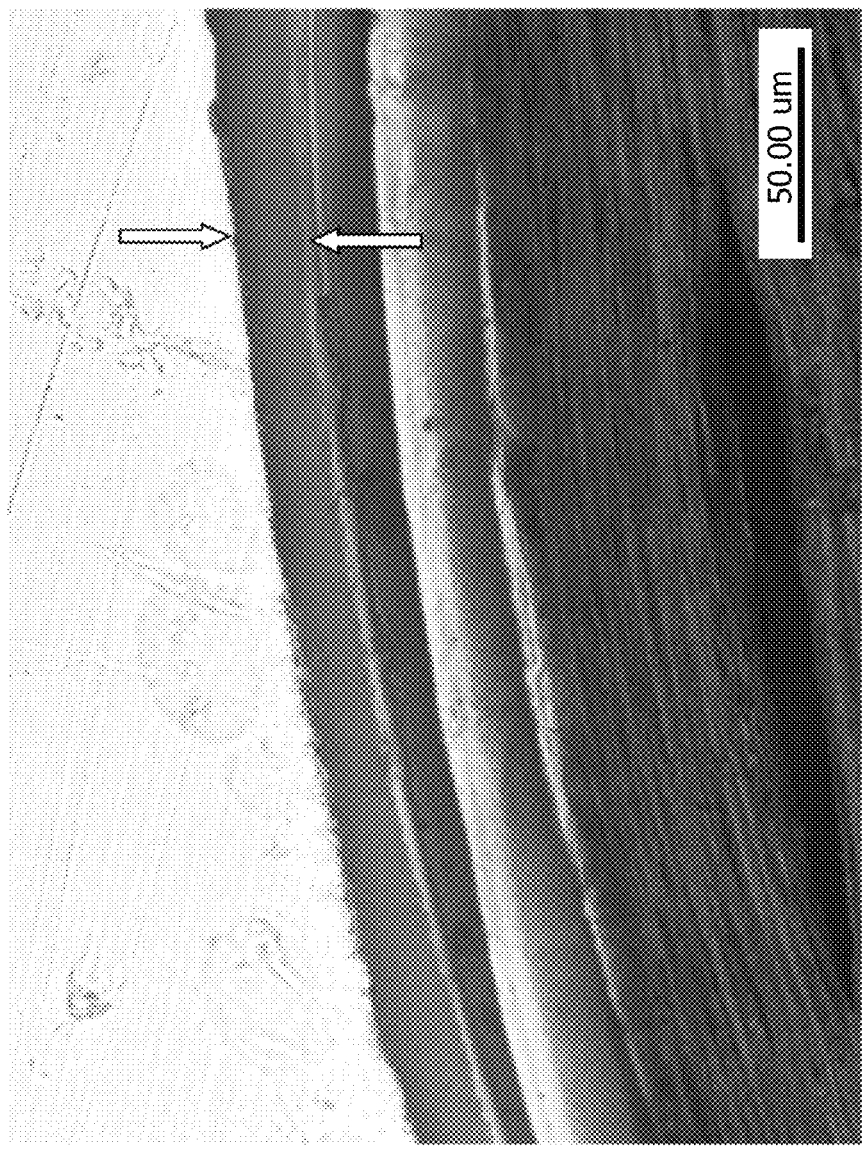
FIG. 24 is a cross section view of a light microscope histology image, displaying a 50 micron bar and stained with H&E, of a vascular graft device wall having an embodiment of the inventive biocompatible material, showing a luminal surface at the top of the image. Block arrows indicate representative cellular fibromuscular neointima that overlies but does not infiltrate the luminal graft biomaterial. The biomaterial is devoid of cell nuclei.

FIG. 24 shows the cross-section of a wall from a vascular stent-graft incorporating a blood contact surface of the present invention made in accordance with Example 3 below, which is implanted in a canine carotid artery under identical conditions and for the same duration as the device of FIG. 23. The microstructure of this inventive device is characterized by a mean IND of about 1.7 micron, and a microstructure that is essentially balanced in its x and y directions. This blood contact surface resembles FIG. 5 in the present application.

FIG. 24 shows a cellular matrix contacting the flow lumen at the top of the image. Block arrows indicate representative cellular fibromuscular neointima that overlies but does not infiltrate the luminal graft biomaterial. The biomaterial is devoid of cell nuclei. The cellular response shown in FIG. 24 demonstrates that cells are not penetrating the microstructure of the inventive material. However, it appears that cells are successfully attaching to the surface of the artificial substrate and a healthy endothelial cell layer is being established on the flow surface of the device.

Figure 25:
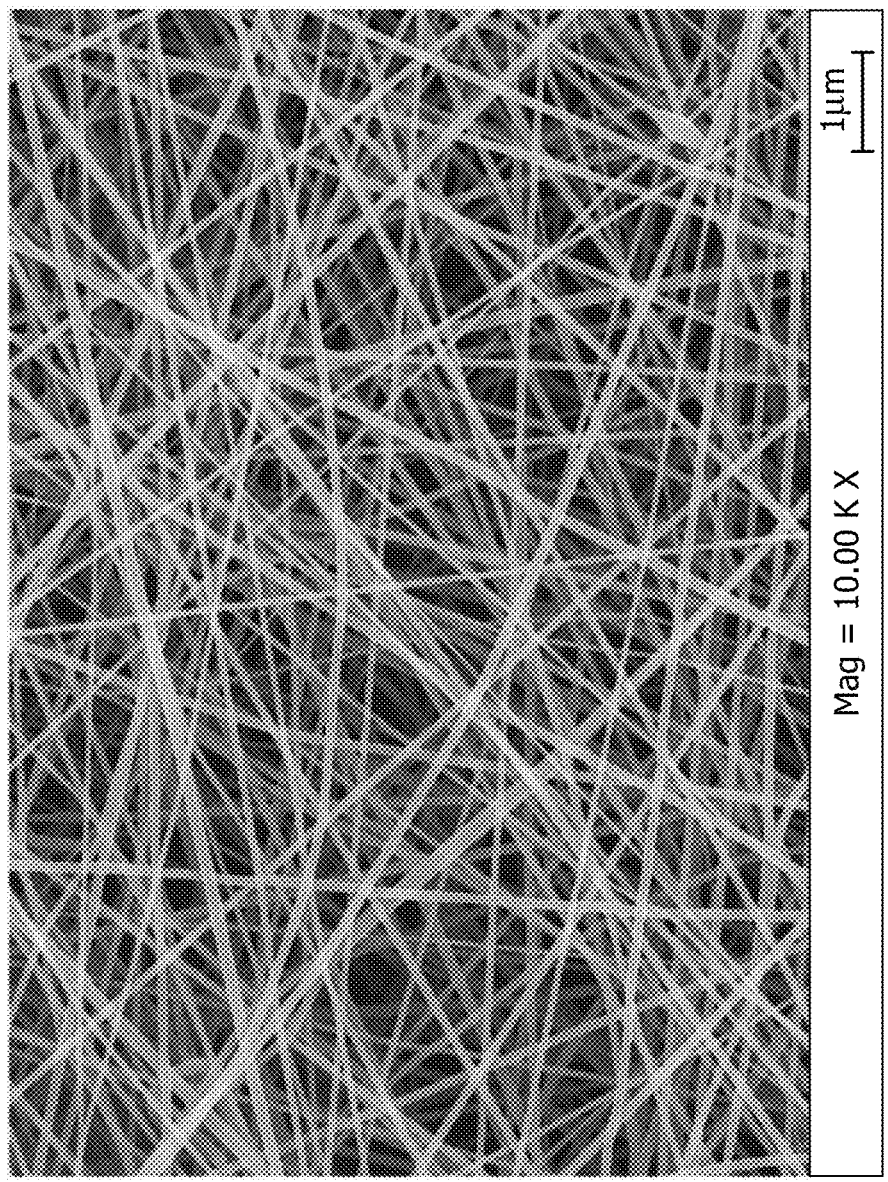
FIG. 25 is an SEM micrograph, taken at 10,000× and including a 1 micron scale bar, of electrospun fibers of polycaprolactam polymer ("nylon 6") comprising another embodiment of a biocompatible surface of the present invention.

As has been noted, it is believed that a variety of materials can be employed to achieve the benefits of the present invention. Certainly fluoropolymer materials such as PTFE and FEP are desirable for their proven bio-compatibility, but other materials made in accordance with the teachings of the present invention may provide comparable performance. By way of example, FIG. 25 is an SEM micrograph, taken at 10,000×, of electrospun fibers of polycaprolactam polymer ("nylon 6") comprising a biocompatible surface of the present invention. These fibers as shown comprise strands of material that intersect at nodal points. Each segment between nodal points comprises a length of less than about 5 micron in length. Again, this microstructure is relatively balanced in the x and y directions.

Figure 26:
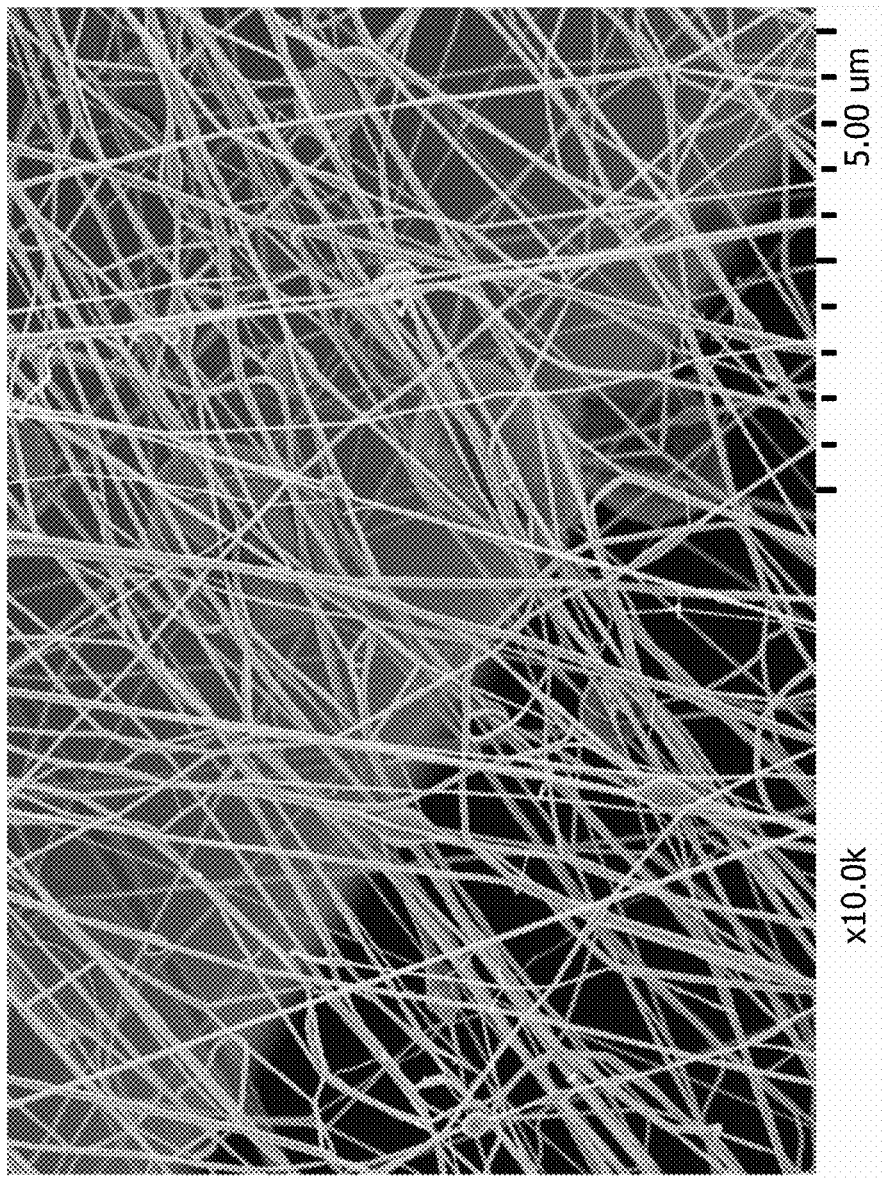
FIG. 26 is an SEM micrograph, taken at 10,000× and including a 5 micron scale bar, of electrospun fibers of a thermoplastic polymer of polyvinylidene fluoride (PVDF) comprising another embodiment of a biocompatible surface of the present invention.

Thermoplastic fluoropolymers may also be formed into a biocompatible surface of the present invention. As is shown in FIG. 26, electrospun fibers of polyvinylidene fluoride (PVDF) may be manufactured comprising short strand segments of less than 5 micron in length between intersecting small nodal points. The microstructure is relatively balanced in the x and y directions. In this instance, a cohesive mat of electrospun PVDF fibers was made using a NanoSpider NS Lab 500 unit (Elmarco, Inc., Morrisville, N.C.). The PVDF material was formed by spinning a 14% solution of KYNAR 710 PVDF (Arkema Inc., King of Prussia, Pa.) in a 4:1 dimethylformamide (DMF):Acetone mixture. Also in the solution was 90 ppm tetraethylammonium bromide to enhance solution conductivity. Spinning conditions were 47.5 kV, with a 135 mm electrode separation distance, and 35% humidity at 23° C. A variety of other materials may also be electrospun in a similar manner, such as polyester, elastomers, fluoro-elastomers, hydrogels, fibroin, etc.

Figure 27:
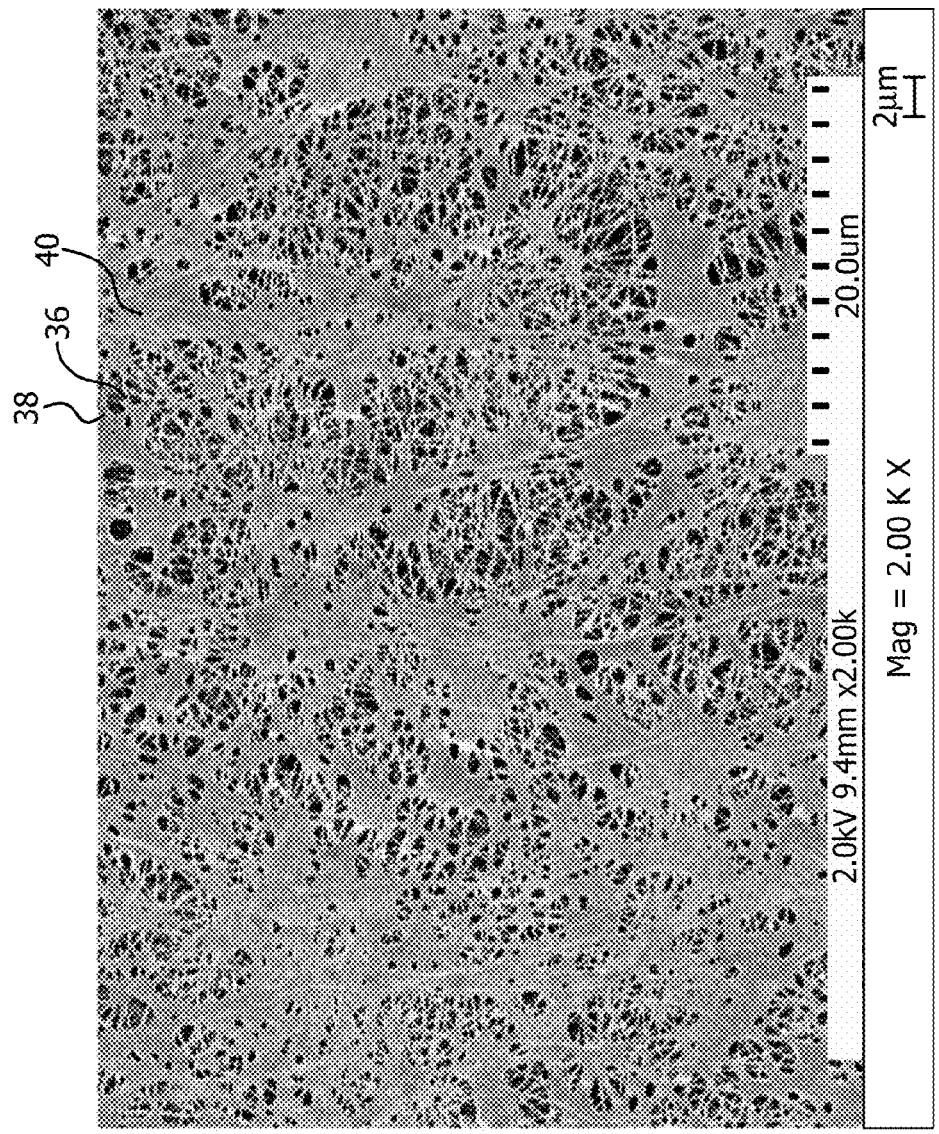
FIG. 27 is an SEM micrograph, taken at 2000×, of another embodiment of a biocompatible surface of the present invention comprising ePTFE and a discontinuous coating of fluorinated ethylene propylene (FEP)

Another example of a biocompatible surface of the present invention is illustrated in the SEM micrograph of FIG. 27. In this example, the inventive surface comprises a combination of ePTFE with a tight microstructure of nodes 36 and fibrils 38, as described herein, and a discontinuous coating 40 of fluorinated ethylene propylene (FEP).

The biocompatible surface of the present invention can be incorporated into a wide variety of products, including devices that are temporarily introduced in a body, devices that are implanted in a body, and devices that contact blood extracorporeally. Without intending to limit the present invention to any particular form of device, examples of each of these uses are set forth in FIGS. 28 through 51 below.

Figure 28A:
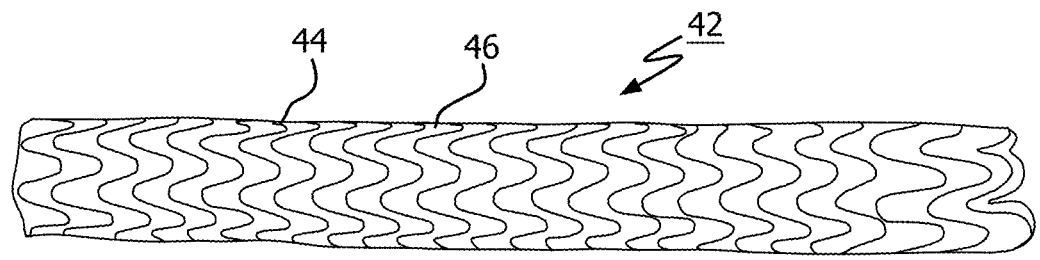
FIG. 28A is a top plan view of a stent-graft device incorporating an embodiment of the present invention.

FIG. 28A shows a stent-graft device 42 comprising at least one stent element 44 and graft element 46 that incorporates a biocompatible surface of the present invention. In this form, the stent-graft 42 is designed for insertion in a peripheral blood vessel, such as in arteries of the legs or arms, to treat occlusive or aneurismal conditions in the blood vessel. The inventive biocompatible surface may be provided on the inside, outside or on both sides of the stent element 44 in this kind of device.

The surface of the present invention can comprise exceptionally strong materials that can be configured into very thin blood contact devices constructed from very few layers of material, up to relatively thick devices constructed from many layers of inventive material and/or from combinations of the polymers of the present invention with other materials. As such, devices made with the inventive material may comprise thicknesses ranging from well less than 0.1 micron to 5 mm or more in thickness, including surfaces comprising <0.1 mm, <0.05 mm, <0.01 mm, <0.005 mm, etc., in thickness.

Figure 28B:
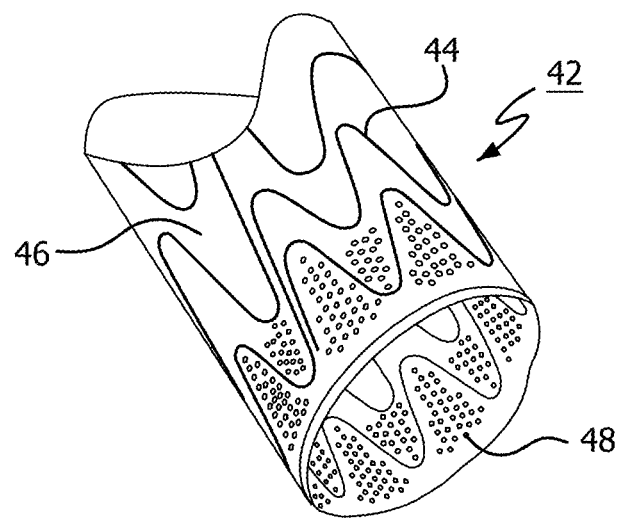
FIG. 28B is an enlarged perspective view of one end of the stent-graft device shown in FIG. 31A, illustrating the addition of 100 micron diameter lased perforations on one of its ends.

FIG. 28B shows an enlarged view of one end of the stent-graft device 42 of FIG. 28A. This view shows the optional addition of a series of perforations 48 on one or both ends of the device, which penetrate into at least a portion of the inventive material and may extend entirely through the thickness thereof. As is explained further in the examples below, such perforations 48 are believed to assist in the attachment of cells to the device. Perforations 48 of this form can be made via a variety of methods, such as with needles or through use of lasers or heat applying apparatus. In the form shown, the perforations 48 are approximately 100 micron in diameter and are made using a laser.

Figure 29:
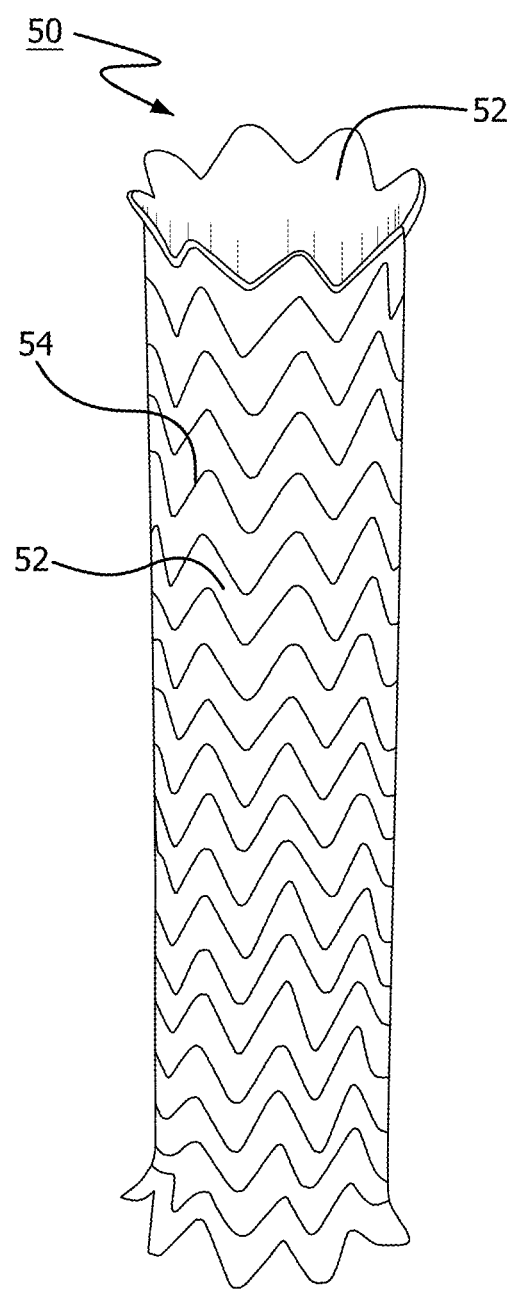
FIG. 29 is a side view of a stent-graft device incorporating an embodiment of the present invention. This device is configured for repair of a thoracic aortic aneurysm.

FIG. 29 shows a stent-graft device 50 incorporating a blood contact surface of the present invention configured for insertion in a large diameter vessel, such as for repair of the thoracic aorta. The device comprises a graft 52 that incorporates the inventive surface and one or more stent elements 54 designed to deliver and hold the graft element in contact with vessel walls.

Figure 30:
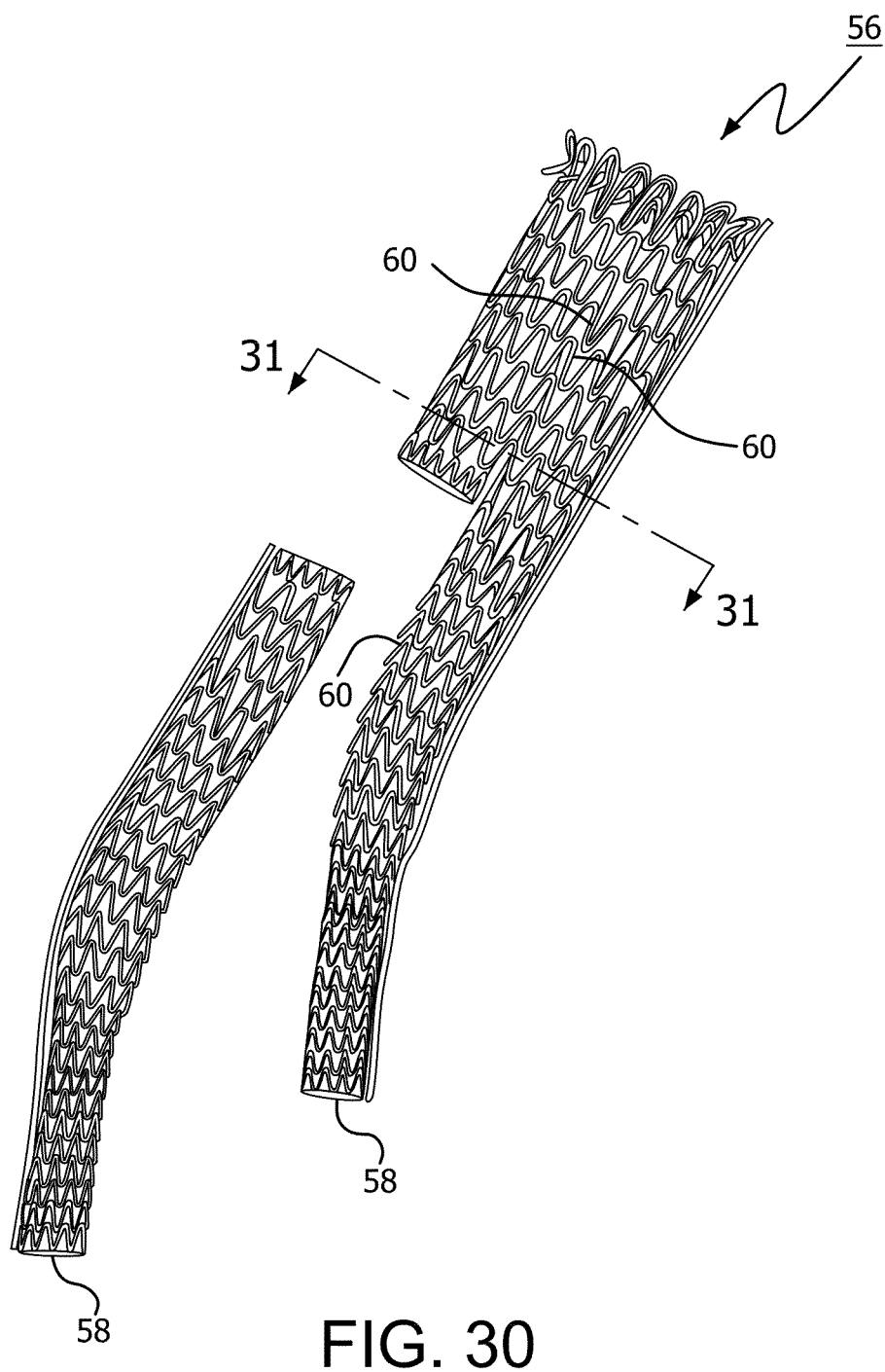
FIG. 30 is a side view of a stent-graft device incorporating an embodiment of the present invention. This device is configured for repair of an abdominal aortic aneurysm.
Figure 31:
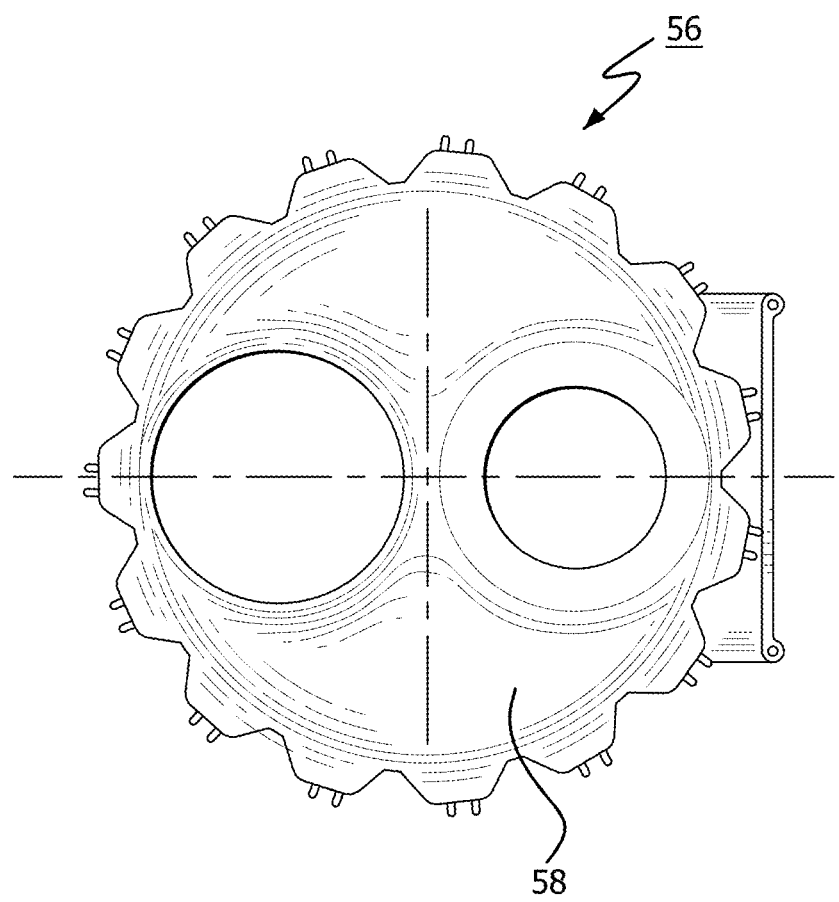
FIG. 31 is a cross-section of the device illustrated in FIG. 30 taken along line 31-31.
Figure 32:
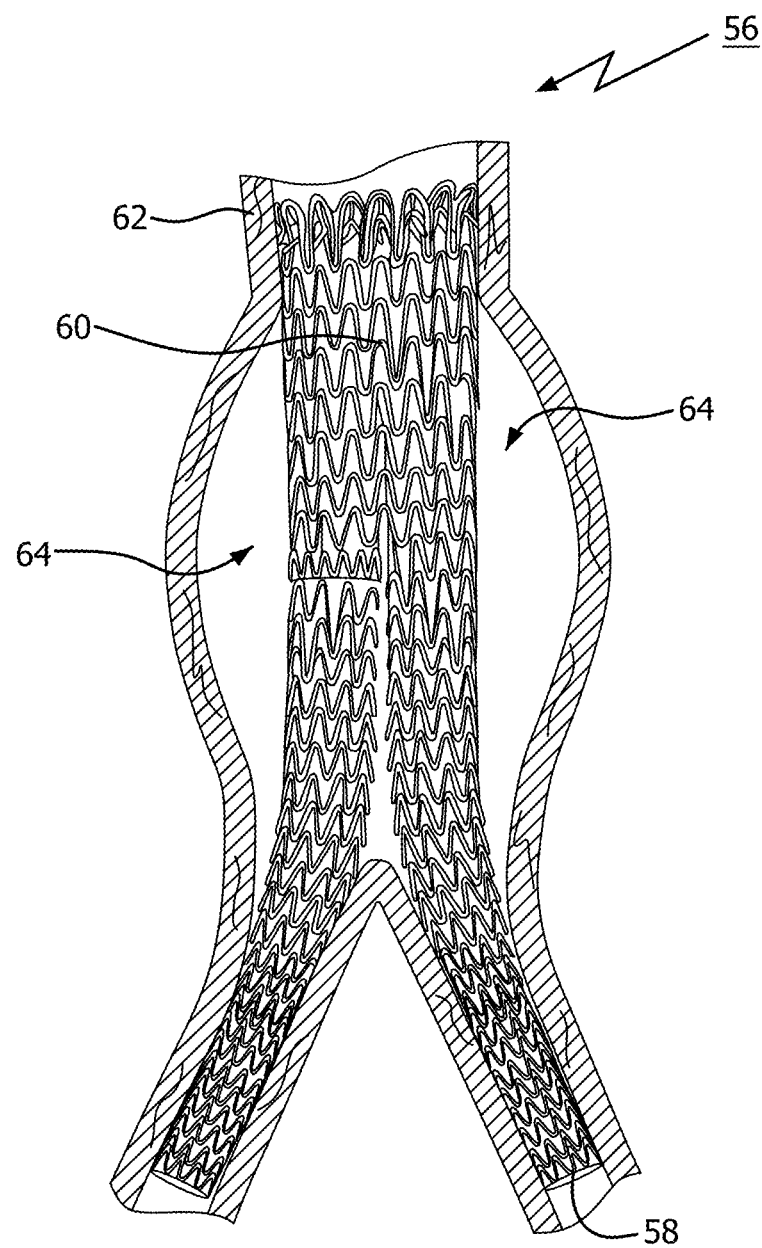
FIG. 32 is a front elevation view of the stent-graft of FIGS. 30 and 31 shown deployed in an abdominal aortic aneurysm.

FIGS. 30 through 32 show a stent-graft device 56 incorporating a blood contact surface of the present invention configured to repair a larger, bifurcated vessel, such as the abdominal aorta. This device is similar in design and construct to that described in U.S. Pat. No. 7,682,380 to Thornton, et al. The device comprises one or more graft elements 58 and one or more stent elements 60. FIG. 32 shows the device deployed in an abdominal aorta 62 to repair an aneurysm 64 therein. The inventive surface may be applied to the device in a manner similar to that described in the Thornton et al. patent, with or without the use of additional tube elements.

Figure 33:
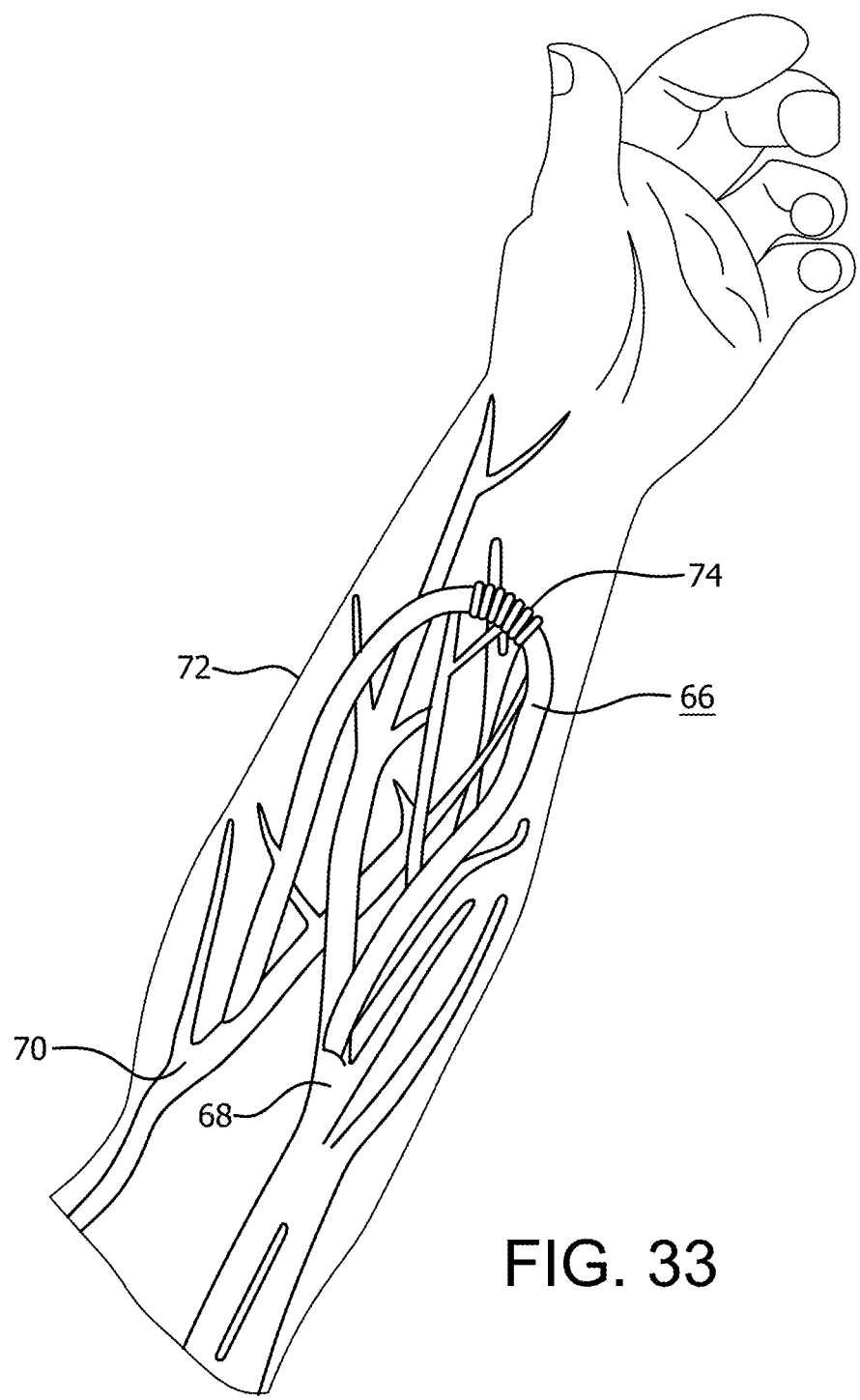
FIG. 33 is a top view of a vascular graft device incorporating an embodiment of the present invention, shown in cut-away, implanted as an arterial-venous (A-V) access graft in a patient's forearm.

FIG. 33 is a top view of a vascular graft device 66 incorporating a blood contact surface of the present invention. This device 66 is shown in cut-away implanted as a shunt between an artery 68 and a vein 70 in a patient's forearm 72 (commonly referred to as an A-V access graft). The vascular graft 66 may be provided with reinforcement 74, rings, strain relief, elastomeric components, external and/or internal stents, etc., as are commonly provided on various vascular graft devices. Again, the inventive surface may be used in conjunction with one or more other materials or the vascular graft may be constructed entirely from the blood contact surface material. Similar vascular graft constructions can be used for a wide variety of other purposes including, without limitation, bypass procedures, repairs of vascular aneurysms, repairs of vascular occlusions, etc.

Figure 35:
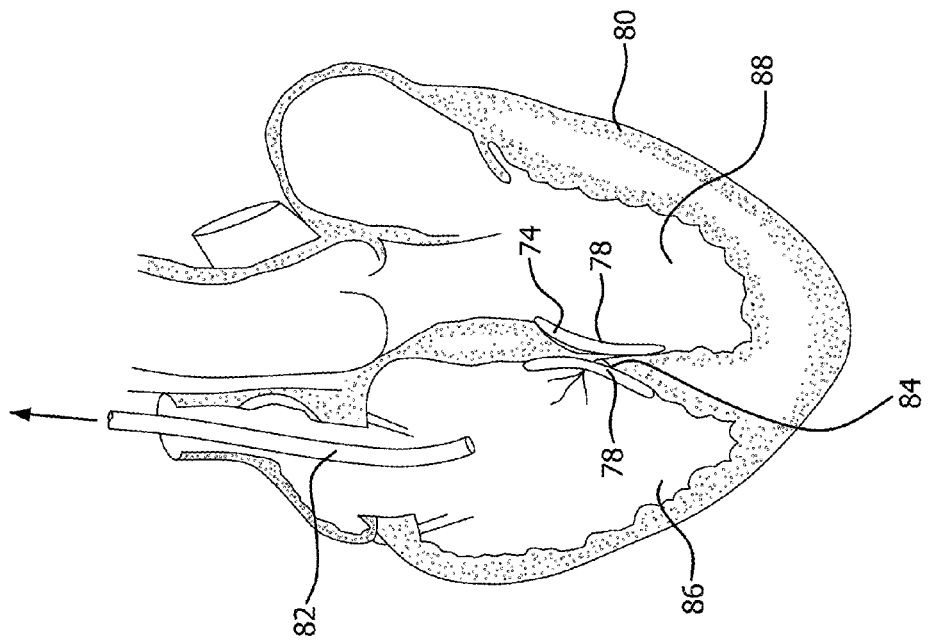
FIG. 35 is a cross-section view of a heart showing the septal defect repair device of FIG. 34 implanted to repair an opening in the septum of the heart.
Figure 34:
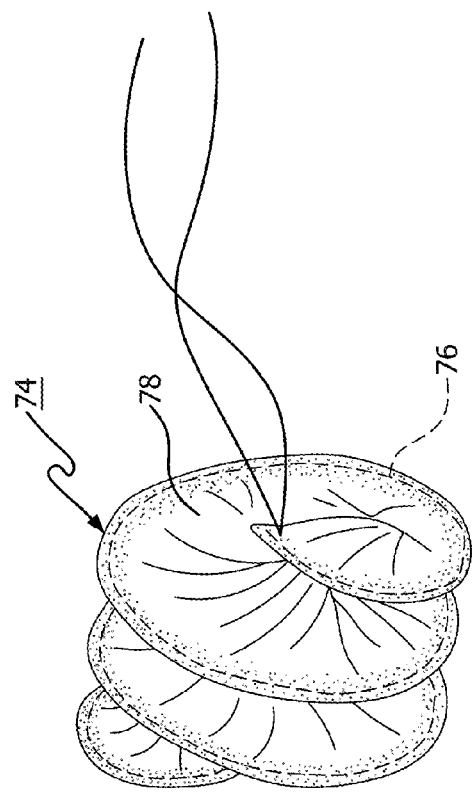
FIG. 34 is a three-quarter perspective view of a catheter-delivered septal defect repair device incorporating an embodiment of the present invention.

Another contemplated use of the inventive material is in devices used to repair defects in vessels or organs. For example, FIGS. 34 and 35 show a closure device 74, such as an occlusion device for repairing an opening in the septum of the heart. The closure device comprises an expanding frame 76, such as one created from nitinol or steel, and a covering 78 which may be constructed from or may include the biocompatible material of the present invention. As is shown in FIG. 35, the device 74 is delivered to a heart 80 using a catheter 82 and is deployed to occlude an opening 84 between heart chambers 86, 88. The use of the inventive surface for this purpose is believed to be beneficial to mitigate negative foreign body response of the device in situ. It should be appreciated by one of skill in the art that there are a wide variety of other occluders, implantable plugs, or embolization devices that may benefit by inclusion of a biocompatible surface of the present invention.

Another use of the biocompatible surface of the present invention is as a sheet 90, such as that shown in FIG. 40. The sheet 90 may be constructed entirely from the inventive material, or it may comprise a composite material with the inventive material provided on one or both surfaces of the sheet 90 (and/or a middle layer of the sheet). Sheets of this form may be used for many different purposes, including to repair holes or rips in vessels or organs, to reinforce weakened vessels or organs, to fashion anatomical structures in situ such as valves, or for any other use currently known or later proposed for such sheet material. Further, sheet material may also be fashioned into other shapes, such as being rolled or otherwise formed into a tube, and/or combined with other materials to form other devices, such as stent-grafts, occluders, heart valves, etc.

Figure 37:
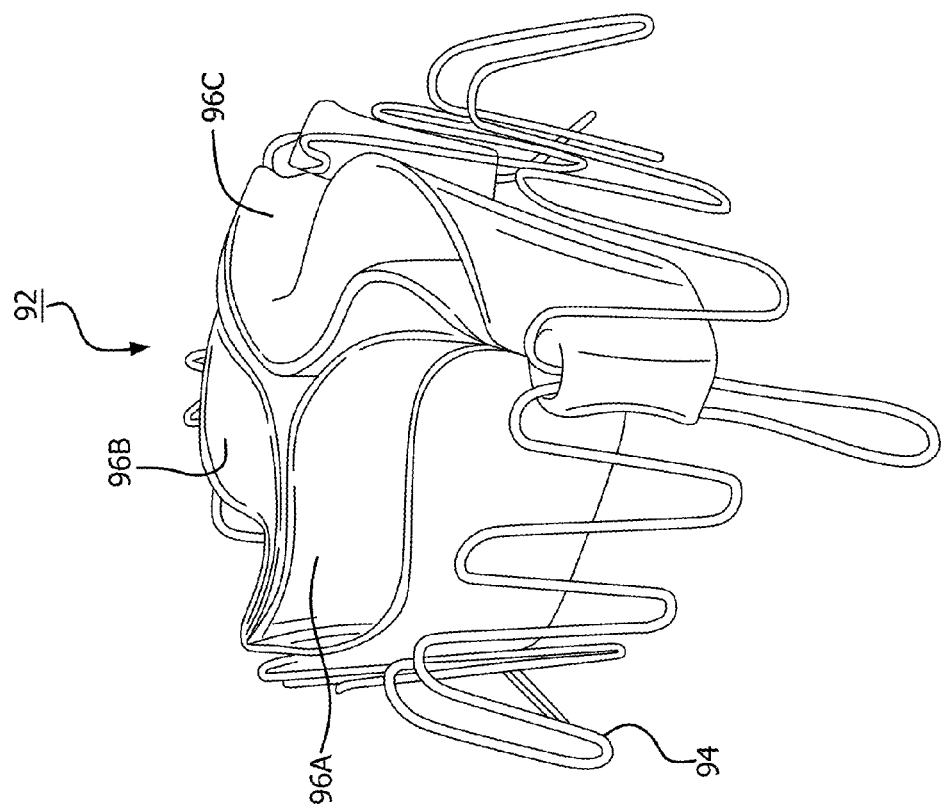
FIG. 37 is a three-quarter perspective view of a endoluminally-deployed heart valve prosthesis incorporating an embodiment of the present invention as valve leaflets.
Figure 36:
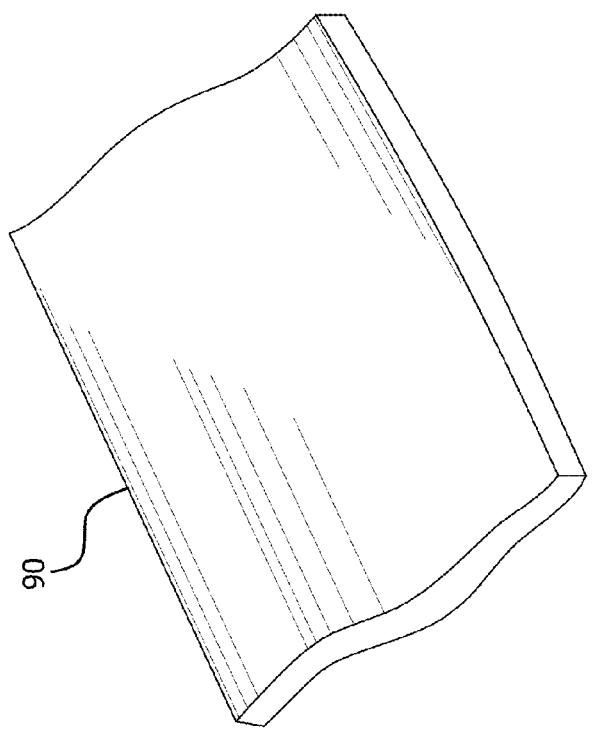
FIG. 36 is a three-quarter perspective view of a sheet device incorporating an embodiment of the present invention.

As has been noted, the biocompatible material of the present invention may be formed into leaflets for various valve devices, such as the heart valve prosthesis 92 shown in FIG. 37. The heart valve 92 shown is designed to be delivered via catheter and deployed remotely within the heart. As such, the valve comprises an expandable frame 94 and one or more valve leaflets 96A, 96B, 96C formed from or including the biocompatible material of the present invention. Valves incorporating inventive material may also comprise valves that can be implanted through surgical procedures, and valves that may be use elsewhere in the body, such as in the venous system.

FIG. 38 shows a schematic representation of extracorporeal blood tubing 98 that incorporates the biocompatible surface of the present invention as the flow surface of the tubing. Tubing of this nature may be used for dialysis, for blood or serum delivery, in a heart-lung machine, or in any other application that handles blood extracorporeally. The tubing may be constructed entirely from the inventive material or the inventive material may be combined with other materials, such as employing the blood contact material as a liner for conventional blood tubing materials such as PTFE, nylon, polyurethanes, or silicone.

The biocompatible material of the present invention may also be incorporated into devices that are introduced only temporarily within a patient's body, such as catheters, balloons, blood filter devices, introducer sheaths, guidewires, etc. Two examples of such uses are shown in FIGS. 39 and 40. FIG. 39 illustrates an endoluminal balloon 100 that incorporates the inventive material as a balloon cover 102 on a catheter balloon. The cover 102 in this instance employs the inventive material as its exterior (blood-facing) surface. A separated fluid-tight balloon 104 or other inflatable/expandable element is provided within the cover 102 to provide the required functionality.

FIG. 40 shows another form of an endoluminal balloon 106 that incorporates the biocompatible material of the present invention as an outer surface 108 of the catheter balloon. In this form, the inventive material is combined integrally with the pressure-containing elements of the balloon.

As the above examples demonstrate, the biocompatible material of the present invention may be employed in a wide variety of devices. These examples are intended to be just a sampling of the possible ways that the present invention may be used and are not intended to limit how the invention may benefit future medical device advancements. It should be understood to those skilled in the art that although the biomaterials of the present invention are particularly well-suited for blood contact applications, they may also may find utility in implantable or non-implantable medical applications that do not involve direct blood contact.

As can be seen, many of the uses of the biocompatible material of the present invention involve shaping the material into a variety of three-dimensional constructs. Described below in reference to FIGS. 41 through 51 are a number of examples of how different inventive tubular devices may be formed from the inventive material. These examples are intended to be illustrative of the many ways the biocompatible surface of the present invention may be used and not limiting of other possible uses.

Figure 41:
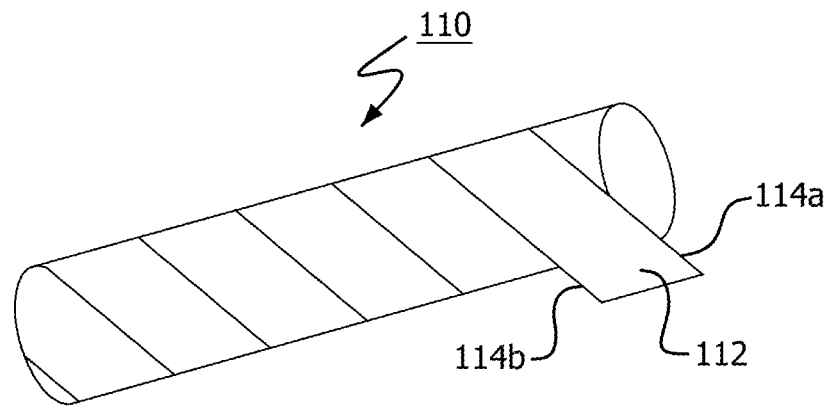
FIG. 41 is a schematic representation of the construction of a tube from a helically wrapped film that embodies the present invention.
Figure 42:
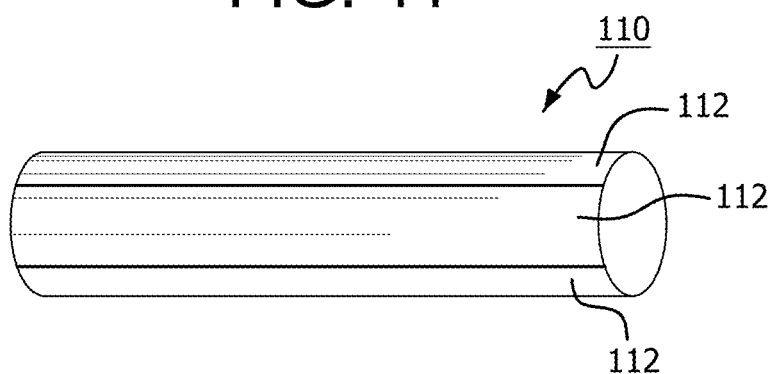
FIG. 42 is a schematic representation of a method to construct a tube from a longitudinally applied film that embodies the present invention.
Figure 43:
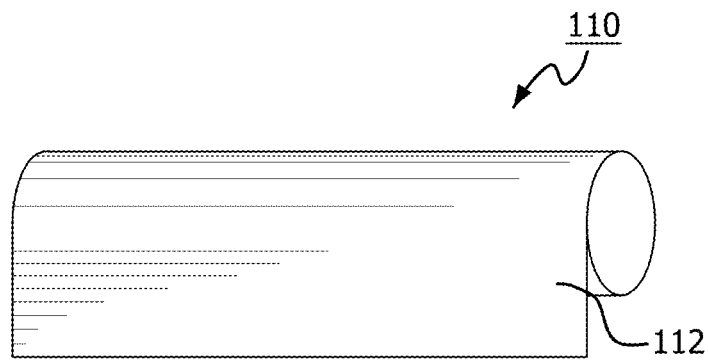
FIG. 43 is a schematic representation of a method to construct a tube from a circumferentially applied film ("cigarette wrap") that embodies the present invention.

FIGS. 41, 42, and 43 show three basic methods for taking a sheet, film, or tape (all being referred to generally as a "film") of inventive material and forming it into a tube. FIG. 41 demonstrates that a tube 110 may be formed by wrapping a narrow film 112 of inventive material helically around a mandrel to lay-up the tube. The film includes edges 114a, 114b.

Alternatively, FIG. 42 demonstrates that a tube 110 may be formed by applying one or more strips of film material 112 longitudinally along the eventual axis of the tube 110.

Further, FIG. 43 demonstrates that a tube 110 may be formed by circumferentially wrapping the film 112 (that is, in a manner commonly referred to as a "cigarette wrap").

With respect to each of the above-described tubular constructs of FIGS. 41 through 43, it should be appreciated that wrapping can comprise a single layer of material or many layers applied over one another. Such wrapping may be accomplished by overlapping edges of the film material on each wrap or the material may be aligned so that edges abut one another or, in the case of the application of multiple layers, a space may be left between the film edges in any given layer. The layers of the tube may be bonded together by applying heat and/or pressure to the wrapped tube, and/or by including sewing, tacking, adhesive or other bonding agent to the wrapped tube to assist in holding it together. In each of these instances, the film tube thus formed includes at least one seam embedded in the thickness of the film tube element. It should be appreciated that each of the methods may be employed individually or they may be combined with each other and/or used in conjunction with other tubular devices (such as using them in conjunction with a separate wrapped or seamless tube). Further, as is described in more detail below, the inventive material may be combined with other materials in the tube to deliver additional benefits.

Figure 44:
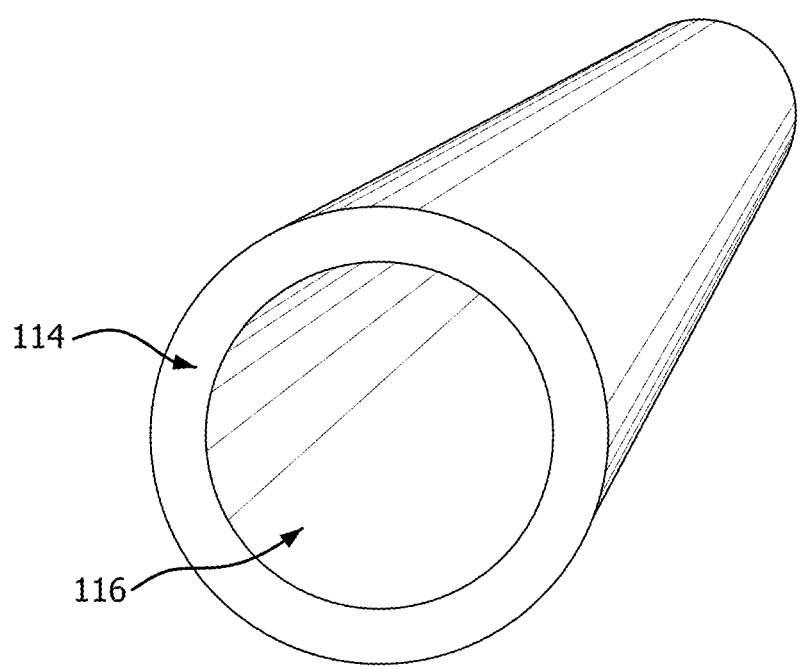
FIG. 44 is a schematic representation of a three-quarter perspective view of an embodiment of the present invention consisting of one or more layers of film of the present invention.

FIG. 44 is a schematic representation of a tube 114 suitable for carrying blood that is constructed from multiple layers of the inventive film. Applying a film with a thickness of approximately 0.0005 mm, the tube can have a thickness of 0.0005 mm (with a single layer of film) up to 5 mm or more (with many layers of film applied over one another). The inner lumen 116 of the tube presents a biocompatible surface of the present invention with a microstructure having an internodal distance of less than 5 micron. The layers of film may be adhered together using only heat and pressure, with no separate adhesive.

Figure 45:
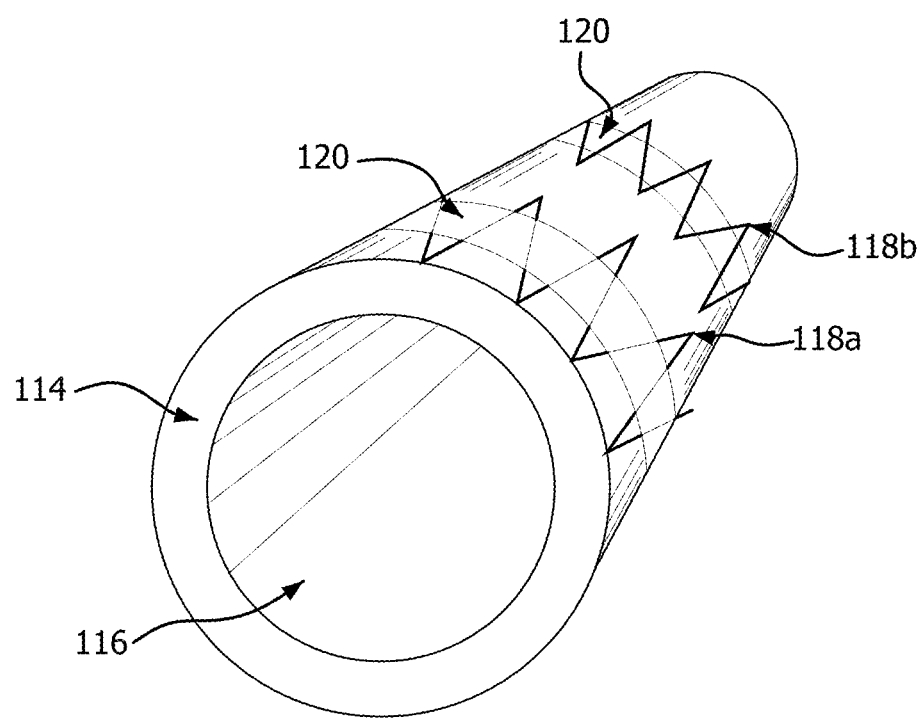
FIG. 45 is a schematic representation of a three-quarter perspective view of an embodiment of the present invention comprising a tube of FIG. 44 and a stent structure attached to the tube.

Shown in FIG. 45 is the tube 114 illustrated in FIG. 44 with the addition of one or more stents 118a, 118b or other expansion elements or reinforcement elements attached to the tube 114. The stents 118 may be attached through any suitable means, including by adhesive, sutures, tape, thermal or laser bonding, sandwiching within another tubular structure, etc. In the illustrated example, the stents 118 are attached using a film/adhesive composite tape 120.

Figure 46:
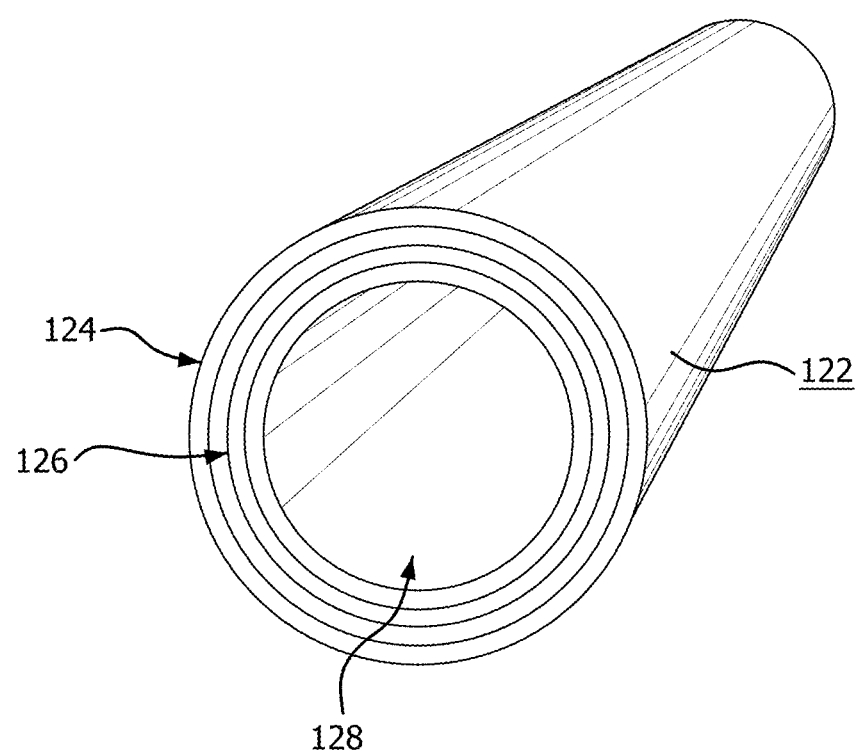
FIG. 46 is a schematic representation of a three-quarter perspective view of an embodiment of the present invention comprising a multi-layered tube, the layers of the tube bonded together with a continuous or discontinuous adhesive.

FIG. 46 is a schematic representation of another example of a tube 122 made from the biocompatible material of the present invention. In this construct, multiple layers of film 124 of the present invention are applied over one another with continuous or discontinuous layers 126 of adhesive employed between some or all of the film layers to assist in holding the layers together. Suitable adhesives for this use may include FEP, EFEP, THV, fluoroelastomers (such as TFE/PAVE copolymers), nylon, polyester, polyurethane, etc. The tube 122 includes an inner lumen 128 with a blood contact surface in accordance with the present invention.

Figure 47:
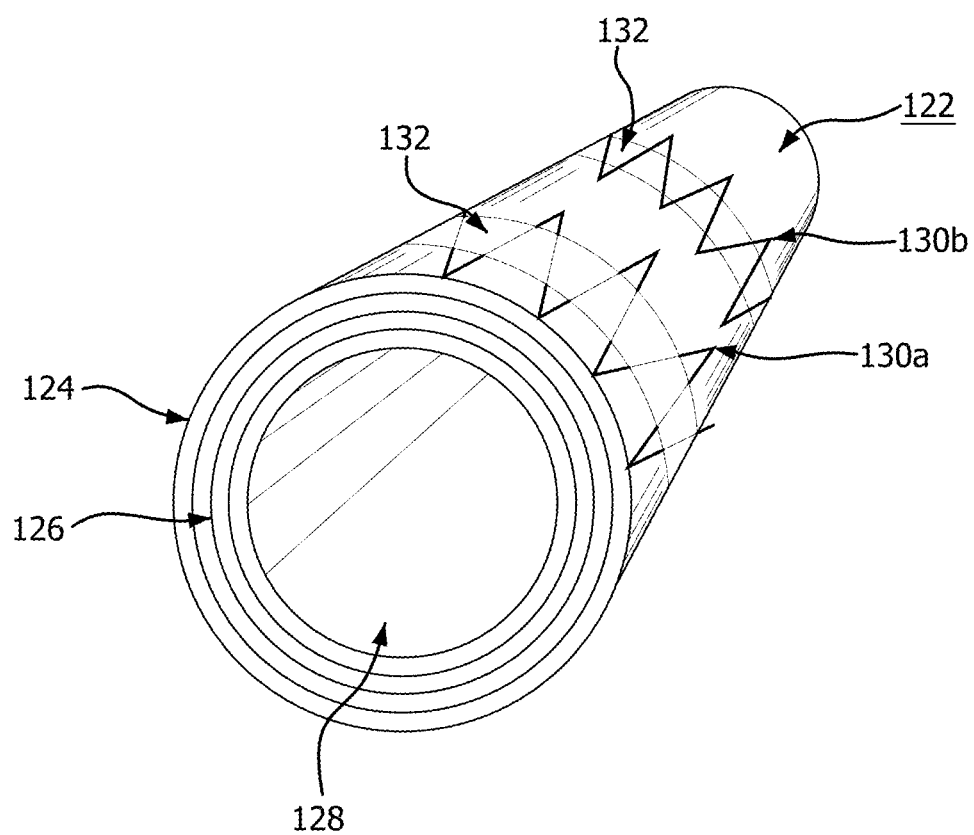
FIG. 47 is a schematic representation of a three-quarter perspective view of the device of FIG. 46 that further includes a stent structure attached to the tube.

Shown in FIG. 47 is the tube 122 illustrated in FIG. 46 with the addition of one or more stents 130a, 130b or other expansion elements or reinforcement elements attached to the tube 122. Again, the stents 130 may be attached to the tube through any suitable means. In the illustrated example, the stents 130 are attached using a film/adhesive composite tape 132.

Figure 48:
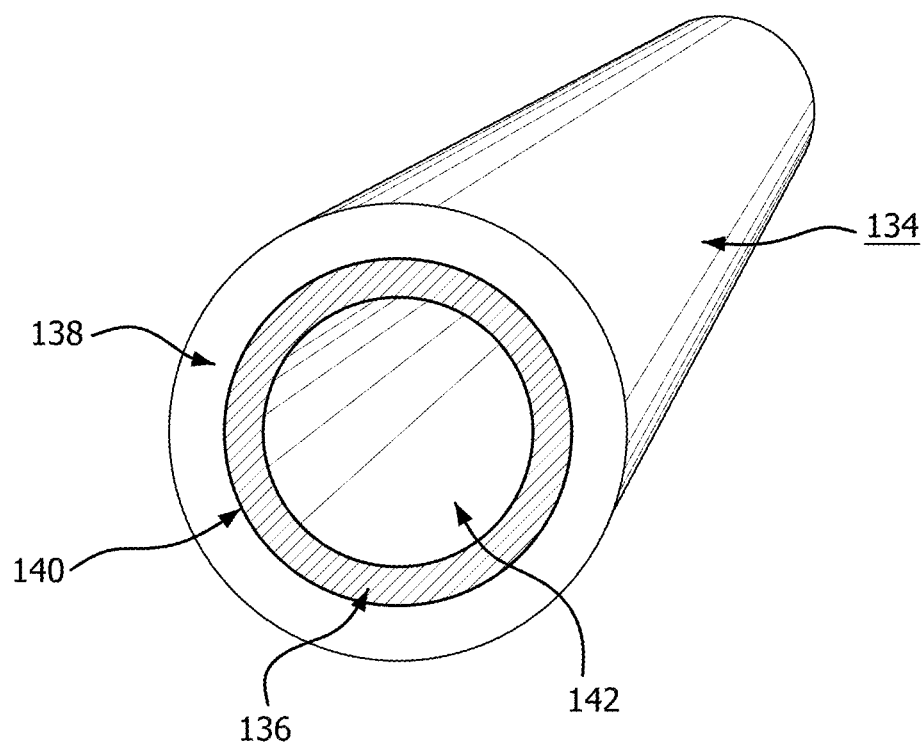
FIG. 48 is a schematic representation of a three-quarter perspective view of an embodiment of the present invention comprising a multi-layered tube, with an inner tube component comprising the inventive biocompatible surface and an outer tube component comprising a different material or microstructure.

FIG. 48 is a schematic representation of another example of a tube 134 made with the inventive material. In this example, the tube 134 comprises an inner tube component 136 comprising a biocompatible surface of the present invention and an outer tube component 138 comprising, for example, a different material or microstructure, such as a conventional seamless blood conduit tube with a microstructure of greater than 6 micron internodal distance (e.g., a conventional expanded PTFE vascular graft tube). The inner tube component 136 and outer tube component 138 may be held together through heat and pressure and/or by the use of an adhesive layer 140, as previously described. The tube 134 includes an inner lumen 142 with a biocompatible surface in accordance with the present invention.

Figure 49:
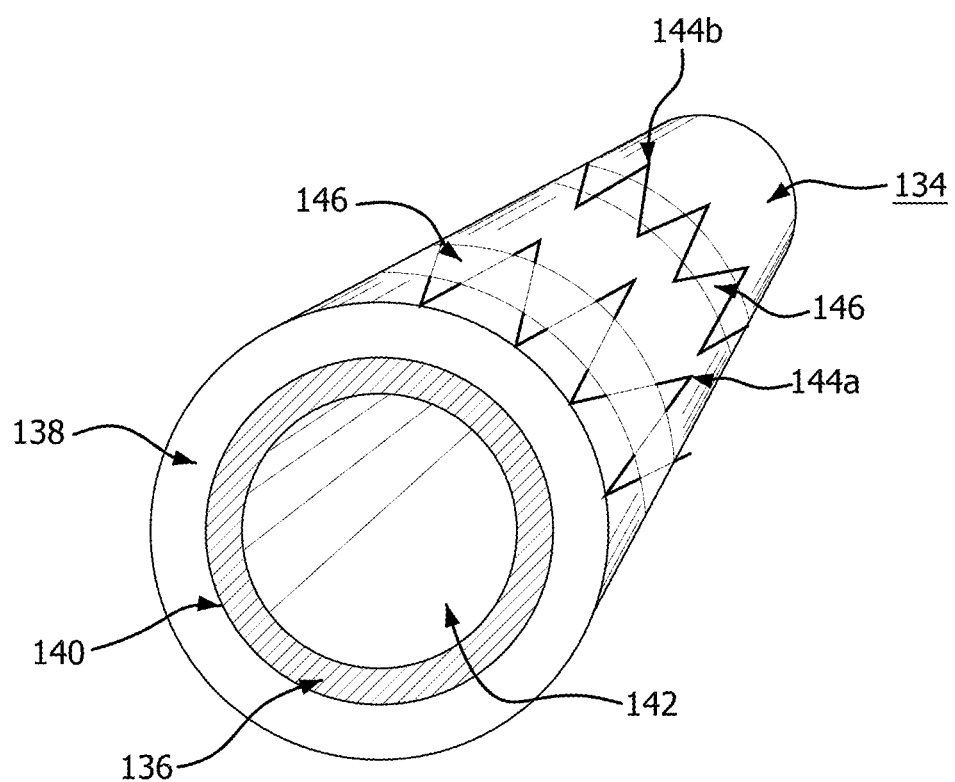
FIG. 49 is a schematic representation of a three-quarter perspective view of the device of FIG. 48 that further includes a stent structure attached to the tube.

Shown in FIG. 49 is the tube 134 illustrated in FIG. 48 with the addition of one or more stents 144*a*, 144*b* or other expansion elements or reinforcement elements attached to the tube 134. Again, the stents 144 may be attached to the tube through any suitable means. In the illustrated example, the stents 144 are attached using a film/adhesive composite tape 146.

Figure 50:
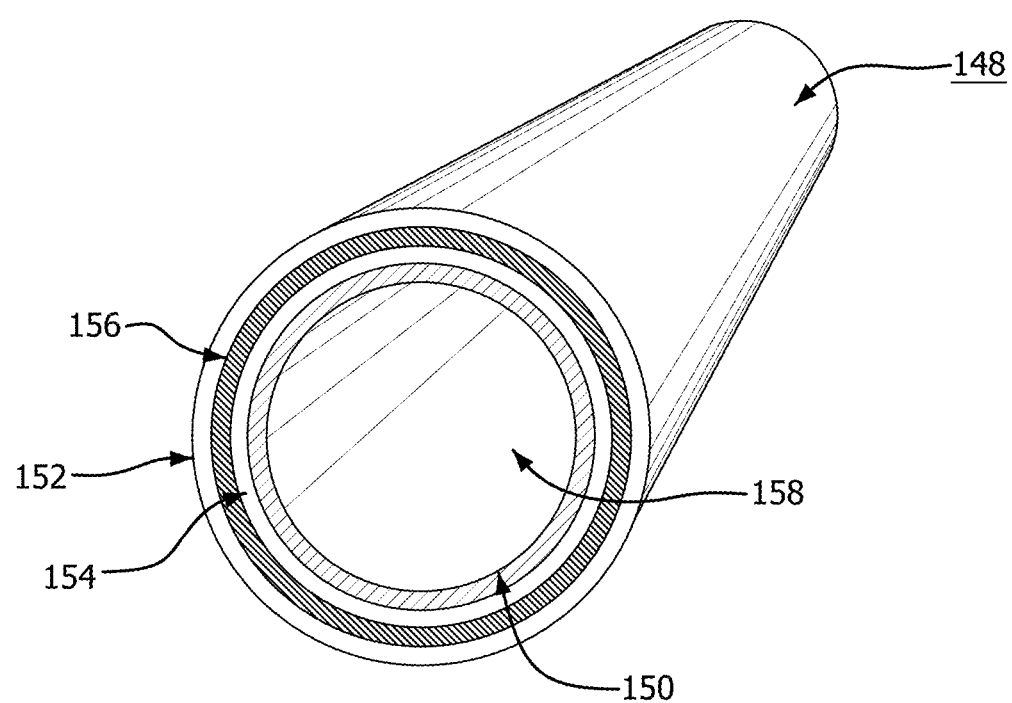
FIG. 50 is a schematic representation of a three-quarter perspective view of an embodiment of the present invention comprising a multi-layered tube, with an inner tube component comprising the inventive biocompatible surface and an outer tube component comprising a different material or microstructure, and multiple additional layers between the inner tube component and the outer tube component.

FIG. 50 is a schematic representation a further example of a tube 148 made with the inventive material. In this example, the tube 148 comprises an inner tube component 150 comprising a surface of the present invention and an outer tube component 152 comprising, for example, a different material or microstructure, such as a conventional seamless blood conduit tube with a microstructure of greater than 6 micron internodal distance (e.g., a conventional expanded PTFE vascular graft tube). One or more additional layers of materials may be sandwiched between the inner and outer components, such as a continuous or discontinuous adhesive layer 154, and other material layers 156, such as non-porous materials to resist fluid leakage through the tube, drug delivery materials, elastomers, elastomeric materials, structural and/or support elements, densified expanded fluoropolymers, coatings of impermeable or partially impermeable materials, coatings of adhesives, drugs and other bio-active substances, etc. The tube 148 includes an inner lumen 158 with a surface in accordance with the present invention.

Figure 51:
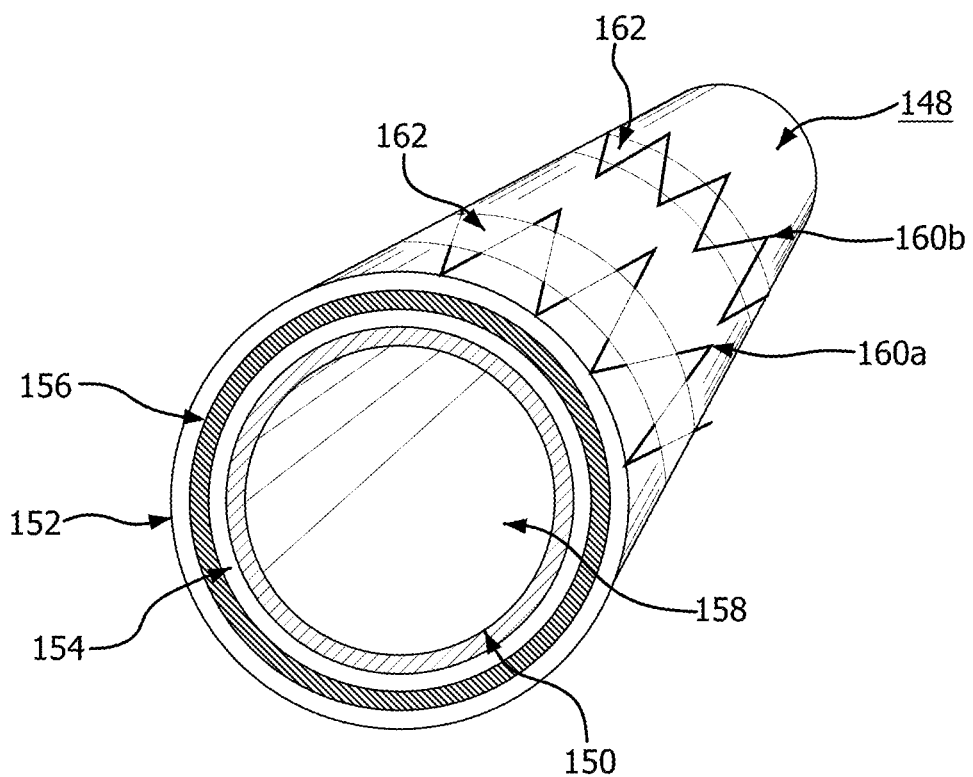
FIG. 51 is a schematic representation of a three-quarter perspective view of the device of FIG. 50 that further includes a stent structure attached to the tube.

Shown in FIG. 51 is the tube 148 illustrated in FIG. 50 with the addition of one or more stents 160*a*, 160*b* or other expansion elements or reinforcement elements attached to the tube 148. Again, the stents 160 may be attached to the tube through any suitable means, and may be attached to the inside, outside, and/or within the tube. In the illustrated example, the stents 160 are attached using a film/adhesive composite tape 162.

As has been noted, it is believed desirable to provide a balanced microstructure in the film and surfaces of the present invention. The balance of the strength of a film is indicated by how closely the ratio of the matrix tensile strengths of the film in two orthogonal directions approaches unity. Balanced films typically exhibit ratios of about 4 to 1 or less, and more preferably 2 to 1 or less, and even more preferably 1.5 to 1 or less, or most preferably a ratio of approximately 1 to 1.

Test Methods and Examples

The present invention can be better understood by the following test methods and examples of the invention. It should be understood that the following examples are for illustrative purposes only and are not intended to limit the scope of the present invention.

Films of fluoropolymers, especially those of copolymers of tetrafluoroethylene (TFE) and those of expanded polytetrafluoroethylene, have a number of benefits that result from their balanced microstructure, including providing a more uniform structure and balanced strength. Even more desirable for some applications are balanced microstructure films that possess very high strength, this is particularly valuable for applications with low profile requirements such as stent-grafts and the like that are endovascularly delivered. Higher strength also affords the use of thinner films, which aids in the highly desirable capability of reducing device profile. Furthermore, strong films better resist rupture in situations in which a device is subjected to high pressures, pulses of pressure, abrasion, and the like.

For some uses, it is also desirable to provide the biocompatible surface with one or more coatings that may assist in its function. For instance, when the surface serves as a vascular prosthesis it may be desirable to include coatings such as heparin, paclitaxol, sirolimus, dexamethasone, rapamycin, or other therapeutic or bioactive agents. Particularly desirable is a heparin coating that is covalently bonded or otherwise attached to the blood contact surface, such as described in U.S. Pat. No. 6,461,665 to Sholander, and U.S. Pat. No. 6,559,132 to Holmer, both assigned to Carmeda AB., Sweden. Other therapeutic agents for a wide variety of applications that can be used with the present invention may include, but are not limited to, antithrombotic agents, anticoagulants, antiplatelet agents, thrombolytics, antiproliferatives, antiinflammatories, hyperplasia and restenosis inhibitors, smooth muscle cell inhibitors, antibiotics, antimicrobials, analgesics, anesthetics, growth factors, growth factor inhibitors, cell adhesion inhibitors, cell adhesion promoters and drugs that may enhance neointimal formation such as the growth of endothelial cells.

Testing Methods Utilized in the Examples:

Film Permeability

Permeability is characterized by Gurley seconds or Frazier number. Increased permeability is manifested by lower Gurley seconds (i.e., less time for a given volume of air to pass through the film at a given pressure) or higher Frazier numbers (i.e., the flow rate of air through the film for a given pressure drop and sample area).

Gurley Measurements

The Gurley air flow test measures the time in seconds for 100 cm$^3$ of air to flow through a 6.45 cm$^2$ sample at 12.7 cm of water pressure. The samples are measured in a Gurley Densometer Model 4340 Automatic Densometer, or comparable apparatus. Articles possessing Gurley values less than about 2 seconds are submitted for Frazier number testing, since this test provides more reliable values for the characterization of highly permeable articles. The average of at least three measurements is used.

Frazier Measurements

The Frazier permeability reading is the rate of flow of air in cubic feet per square foot of sample area per minute at a differential pressure drop across the test sample of 12.7 mm water column. Air permeability is measured by clamping a test sample into a circular gasketed flanged fixture which provides a circular opening of 17.2 cm diameter. The upstream side of the sample fixture is connected to a flow meter in line with a source of dry compressed air. The downstream side of the sample fixture is open to the atmosphere. The flow rate through the sample is measured and recorded as the Frazier number. The average of at least three measurements is used. Frazier number data can be converted to Gurley numbers by use of the following equation: Gurley=3.126/Frazier, in which Gurley number is expressed in units of seconds.

Burst Strength Measurements

The burst strength test measures the pressure of water required to mechanically rupture a tube. 8 mm film tube samples are prepared by lining them with an 8.0 mm OD (outer diameter) by 0.8 mm thick latex tube. 5 mm film tube samples are prepared by lining them with a 4.8 mm OD by 0.4 mm latex tube. The lined samples are cut to approximately 140 cm. A small metal hose is inserted into one end of the lined sample and held in place with a clamp to create a water-tight seal. A similar clamp is placed on the other end of the sample. Room temperature water is pumped into the sample at a rate of 69 kPa/s through the metal hose which is connected to an automated sensor that records the maximum pressure achieved before mechanical rupture of the tube sample. The values presented for burst strength are the average of three measurements.

Bubble Point Measurements

Pore size is characterized by the bubble point (BP) value. Higher bubble point values (the pressure required to pass a bubble of air through a wetted sample of film) indicate smaller pore sizes. The bubble point and mean flow pore size are measured according to the general teachings of ASTM F31 6-03 using a Capillary Flow Porometer (Model CFP 1500 AEXC from Porous Materials Inc., Ithaca, N.Y.), or comparable procedure and/or apparatus. The sample film is placed into the sample chamber and wet with SilWick Silicone Fluid (available from Porous Materials Inc.) having a surface tension of approximately 20 dynes/cm. The bottom clamp of the sample chamber has a 2.5 cm diameter, 3.2 mm thick/40 micron porous metal disk insert (Mott Metallurgical, Farmington, Conn.), or comparable apparatus, and the top clamp of the sample chamber has a 3.175 mm diameter hole. Using Capwin software, or comparable software, the following parameters are set as specified in the table immediately below. The values presented for bubble point and mean flow pore size are the average of two measurements.

| Parameter | Set Point |
|---|---|
| maxflow (cc/m) | 200000 |
| bublflow (cc/m) | 100 |
| F/PT (old bubltime) | 50 |
| minbppres (PSI) | 0 |
| zerotime (s) | 1 |
| v2incr (cts) | 10 |
| preginc (cts) | 1 |
| pulse delay (s) | 2 |
| maxpre (PSI) | 500 |
| pulse width (s) | 0.2 |
| mineqtime (s) | 30 |
| presslew (cts) | 10 |
| flowslew (cts) | 50 |
| eqiter | 3 |
| aveiter | 20 |
| maxpdif (PSI) | 0.1 |
| maxfdif (cc/m) | 50 |
| sartp (PSI) | 1 |
| sartf (cc/m) | 500 |

Thickness Measurements

Film thickness is measured by placing the film between the two plates of a Kafer FZ1000/30 thickness snap gauge (Kafer Messuhrenfabrik GmbH, Villingen-Schwenningen, Germany) or any other suitable gauge or other acceptable measurement technique. The average of at least three measurements is used.

Tensile Break Load Measurements and Matrix Tensile Strength (MTS) Calculations

Tensile break load for films and tubes is measured using an INSTRON 5564 tensile test machine equipped with flat-faced grips and a 0.45 kN load cell, or any comparable tensile testing apparatus. The gauge length is 5.1 cm and the cross-head speed is 51 cm/min. Sample length is 12.7 to 15.2 cm. Film sample width is 2.5 cm. Films weighing less than 1 g/m$^2$ are tested using 4 plies per sample to increase measurement resolution. Each sample is weighed using a Mettler Toledo Scale Model AG204, or comparable apparatus, then the thickness of the samples is taken using the Kafer FZ1000/30 thickness snap gauge, or comparable apparatus. The samples are then tested individually on the tensile tester. The average of at least three maximum load (i.e., the peak force) measurements is used. The longitudinal and transverse matrix tensile strength (MTS) are calculated using the following equation:

$$MTS = (\text{maximum load/cross-section area}) \times (\text{bulk density of PTFE})/\text{density of the porous film}),$$

wherein the bulk density of PTFE and FEP is taken to be 2.2 g/cc.

Scanning Electron Microscope (SEM) Micrographs

Samples are prepared for the SEM by mounting them on a 12.7 mm diameter aluminum mount with the use of conductive carbon adhesive. The mounted samples are taut when mounted in order to minimize slack in the microstructure. The sample surfaces are grounded to the mounts with copper tape and receive a iridium sputter coating in an Emitech K575X system, or comparable apparatus. SEM images are collected with a Leo Supra 35 VP, or comparable apparatus, using an electron beam energy of 2.0 kV. When at a magnification of 10,000×, the final aperture and working distance are selected to limit the depth of field to less than 5 μm. The axial direction of a tube sample (or longitudinal direction of a film sample) corresponds with either the vertical or horizontal direction of the image. The images are saved in TIF format with a resolution of at least 1 pixel/10 nm, a minimal size of 512×512 pixels, and an overlaid calibrated scale bar. Imaged microstructures used for internodal distance, nodal width, fibril width and fibril orientation measurements should be representative of the microstructure found throughout the majority of the film surface or device surface from which the sample is taken.

Inter Nodal Distance (IND)

Internodal distance is measured using PC-based Image-Pro® Plus version 6.3 software by MediaCybernetics Inc., Bethesda, Md., or comparable apparatus. The TIF file of an SEM image obtained at 10,000× magnification is imported and calibrated according to the overlaid scale bar in the image. The straight-line distances between the adjacent boundaries of pairs of adjacent nodes are measured. Measurements are performed on the very surface (top-most portions of the structure if discernable) of the microstructure. Portions of the microstructure not appearing on the very surface are excluded from measurements. Lines of measurement that intersect the boundary of any other interposed node are rejected. The internodal distance values presented are the average of the 30 or more (e.g., 32) longest lines of measurement from each image.

Fibril Width

Fibril width is measured using PC-based Image-Pro® Plus version 6.3 software by MediaCybernetics Inc., or comparable apparatus. The TIF file of an SEM image obtained at 10,000× magnification is imported and calibrated according to the overlaid scale bar in the image. Measurements are performed on the very surface (top-most portions of the structure if discernable) of the microstructure. Fibrils in the microstructure not appearing on the very surface are excluded from measurements. The straight-line distance of fibril widths, which are orthogonal to the fibril orientation, are measured. Lines of measurement are taken at the widest point of each fibril. Fibril width values presented are the average of at least 30 widest lines of measurement from each image.

Ratio of Inter Nodal Distances in X and Y Directions

As has been noted, the degree of balance of the microstructure of the blood contact surface of the present invention can be determined by comparing the internodal distance of the microstructure in perpendicular directions. This can be accomplished by determining the internodal distance as described above along a first axis of the microstructure and then determining the internodal distance of the microstructure along an axis perpendicular to the first axis. Dividing the two perpendicular internodal distances provides the ratio. It should be understood that if the ratio of IND is <1, then the ratio be may inverted to a ratio of Y:X.

Width of Nodes

As has been described, the width of nodes of the microstructure of the biocompatible surface of the present invention can be determined by employing a representative 10,000× enlarged SEM micrograph of biomaterial with approximately a 2000V EHT. From this micrograph, a representative sampling of at least 30 thickest nodes is selected. Measuring the approximately thickest portions of each of the thickest nodes, nodal width is determined. Values presented are the mean of the 32 widest nodes from each image. Alternatively, nodal width measurements may also be made by employing the crosshair selection method previously described with respect to determining IND.

Fibril Orientation

Fibril orientation was measured using PC-based Image-Pro® Plus version 6.3 software by MediaCybernetics Inc., or comparable apparatus. The calibrated image from fibril width measurements is used. The axial direction of the tube (or "longitudinal direction" of a film (that is, the direction in which the polymer was expanded)) is marked with a straight dashed line. Angles of measurement are taken for the same fibrils and at the same locations as fibril width measurements. Straight solid lines are drawn along the fibrils, parallel to their orientation. An angle of measurement is taken at the acute angle between the straight solid line and straight dashed line. Fibril orientation values presented are the average of the 32 angles of measurement from each image.

EXAMPLES

Example 1

Fine powder of high molecular weight PTFE polymer, one example of which is described in U.S. Pat. No. 4,576,869 to Malhotra, is blended with Isopar K (Exxon Mobil Corp., Fairfax, Va.) in the proportion of 0.160 g/g of fine powder. The lubricated powder is compressed in a cylinder to form a pellet and placed into an oven set at 70° C. for approximately 12 hours. Compressed and heated pellets are ram extruded to produce tapes approximately 15.2 cm wide by 0.73 mm thick. Two separate rolls of tape are produced and layered together between calendering rolls to a thickness of 0.51 mm. The tape is then transversely stretched to 56 cm (i.e., at a ratio of 3.7:1) and restrained. The tape is simultaneously longitudinally expanded and dried at 250° C. between banks of rollers. The speed ratio between the second bank of rolls and the first bank of rolls, and hence the expansion ratio, is 4:1. The longitudinally expanded tape is then expanded transversely at a temperature of approximately 350° C. to a ratio of 27:1 and then constrained and heated in an oven set at 380° C. for approximately 25 seconds. The process produces a thin film with a highly fibrillated tight microstructure. The properties for this example film appear in the column headed "Inventive Film, $1^{st}$ Embodiment" of the Table of FIG. 11.

An 8.2 mm round stainless steel mandrel is helically wrapped with sacrificial 0.03 mm thick polyimide slit to a width of 6.4 mm using a pitch of 6.0 mm/rev. The above described film is slit to a width of 6.4 mm and two cross-plied helical wraps are applied over the polyimide at individual pitches of 2.8 and 2.5 mm/rev. The sample is constrained and heated in a 32 mm inner diameter quartz/carbon induction heater oven set to 440° C. for approximately 50 seconds. After cooling to room temperature, the sample is removed from the mandrel and the sacrificial polyimide is removed from the inner diameter of the ePTFE graft. The properties for this film tube example appear in the column headed "4 Layers of $1^{st}$ Embodiment of Inventive Film, Cross-Plied" of the Table of FIG. 12.

Example 2

Fine powder of PTFE polymer, as described and taught in U.S. Pat. No. 6,541,589 to Baillie, is blended with Isopar K (Exxon Mobil Corp., Fairfax, Va.) in the proportion of 0.209 g/g of fine powder. The lubricated powder is compressed into a cylinder to form a pellet and placed into an oven set at 49° C. for approximately 12 hours. Compressed and heated pellets are ram extruded to produce tapes approximately 15.2 cm wide by 0.73 mm thick. Two separate rolls of tape are produced and layered together between calendering rolls to a thickness of 0.40 mm. The tape is then transversely stretched to 32 cm (i.e., at a ratio of 4.7:1), then dried at a temperature of 230° C. The dry tape is longitudinally expanded between banks of rolls over a heated plate set to a temperature of 345° C. The speed ratio between the second bank of rolls and the first bank of rolls is 22:1. The longitudinally expanded tape is then expanded transversely at a temperature of approximately 350° C. to a ratio of 41:1 and then restrained and heated in an oven set at 380° C. for approximately 45 seconds. The process produces an extremely strong and thin balanced film with a highly fibrillated tight microstructure similar to those taught in U.S. Pat. No. 7,306,729 to Bacino et al. The properties for this example film appear in the in the column headed "Inventive Film, $2^{nd}$ Embodiment" of the Table of FIG. 11.

A sacrificial 0.10 mm (wall) thick ePTFE tube is stretched over an 8.0 mm round stainless steel mandrel and then helically wrapped with sacrificial 0.03 mm thick polyimide slit to a width of 12.7 mm using a pitch of approximately 12.0 mm/rev. The above described film is slit to a width of 14.0 cm and 60 circumferential wraps are applied over the polyimide. The sample is constrained and heated in a Greive NT-1000 oven set to 370° C. for approximately 10 minutes. After cooling to room temperature, the mandrel and sacrificial materials are removed from the inner diameter of the ePTFE graft. The properties for this film tube example appear in the column headed "60 Layers of $2^{nd}$ Embodiment of Inventive Film, Circumferential Wrapped" of the Table of FIG. 12.

Example 3

Fine powder of high molecular weight PTFE polymer, one example of which is described in U.S. Pat. No. 4,576,869 to Malhotra, is blended with Isopar K (Exxon Mobil Corp., Fairfax, Va.) in the proportion of 0.160 g/g of fine powder. The lubricated powder is compressed in a cylinder to form a pellet and placed into an oven set at 70° C. for approximately 12 hours. Compressed and heated pellets are ram extruded to produce tapes approximately 15.2 cm wide by 0.73 mm thick. Two separate rolls of tape are produced and layered together between calendering rolls to a thickness of 0.51 mm. The tape is then transversely stretched to 56 cm (i.e., at a ratio of 3.7:1) and restrained. The tape is simultaneously longitudinally expanded and dried at 250° C. between banks of rollers. The speed ratio between the second bank of rolls and the first bank of rolls, and hence the expansion ratio, is 4:1. The longitudinally expanded tape is then expanded transversely at a temperature of approximately 350° C. to a ratio of 27:1 and then constrained and heated in an oven set at 380° C. for approximately 25 seconds. The process produces a thin film with a highly expanded tight microstructure.

A 5 mm round stainless steel mandrel is helically wrapped with sacrificial 0.03 mm thick polyimide slit to a width of 6.4 mm using a pitch of approximately 6.4 mm/rev. The above described film is slit to a width of 6.4 mm and two cross-plied helical wraps are applied over the polyimide at individual pitches of 5.6 and 5.5 mm/rev. The sample is constrained in a 32 mm inner diameter SS induction heater oven set to 380° C. for approximately 40 seconds followed by a forced air heated oven set to 575° C. for approximately 20 seconds. After cooling to room temperature, the mandrel and the sacrificial polyimide are removed from the inner diameter of the ePTFE graft.

Using the general process described in U.S. Pat. No. 6,042,605 to Martin et al., the above described graft is converted into a 5 mm diameter by 5 cm long self-expanding stent graft with a helically wound 0.15 mm diameter nitinol wire and a 0.02 mm thick FEP/ePTFE graft attach film. On one end of the stent-graft, the graft is contoured to match the wound pattern of the nitinol wire.

The non-contoured end of the resultant stent-grafts are then perforated with holes through the wall of graft material. A 25 W $CO_2$ laser with rotary controls is used to create the perforations. The stent grafts are mounted on a stainless steel mandrel which has been lightly grit blasted to assist in laser energy diffusion. Perforations are thought to provide transmural passageways for cells and therefore facilitate rapid in-growth through the holes in the graft, since none is expected to be able to penetrate through the microstructure. The through-holes are approximately 100 μm in diameter and arranged in a triangular pattern within the stent frame apices. The pattern is limited in size to ensure that the laser beam will not damage the nitinol stent. By virtue of its design, the stent frame contains apices of various sizes. As well, the contoured end requires less perforation patterns than the straight end. Approximately 33 holes are lased in the larger apices; approx 18 holes are lased in the smaller apices. After lasing, the devices are cleaned and inspected.

Using the general processes described in U.S. Pat. No. 6,461,665 to Sholander, and U.S. Pat. No. 6,559,132 to Holmer, the above described stent graft receives a covalently bonded heparin coating. It is then loaded onto a GORE VIABAHN® Endoprosthesis (W.L. Gore & Associates, Inc., Flagstaff, Ariz.) commercial delivery system using the conventional processes.

The above described heparin-coated stent graft is endovascularly implanted into the right carotid artery of a canine subject. The only medication the subject received post-implantation is 81 mg of aspirin and 50 mg of dipyridamole per day. After 60 days, the animal is euthanized and the device is retrieved. Surface SEM and histology on plastic-embedded specimens reveals no cellular penetration of the luminal graft material along the entire length of the device. Representative histology slides of this procedure are included as FIGS. 26 and 27 herein.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A blood contact surface comprising
   a polytetrafluoroethylene microstructure of nodes and fibrils in both an x direction and in a substantially perpendicular y direction;
   wherein the nodes and fibrils have a mean distance between adjacent nodes of 5 micron or less; and
   wherein the mean width of the 32 largest nodes in a representative 10,000× SEM micrograph is less than about 1.5 micron.

2. The blood contact surface of claim 1 wherein the nodes and fibrils have a ratio of mean distances between adjacent nodes in the x and y directions of about 2:1 to 1.1.

3. The blood contact surface of claim 2 wherein the ratio of mean distances between adjacent nodes in the x and y directions is about 1:1.

4. The blood contact surface of claim 1 wherein the expanded polytetrafluoroethylene comprises a multi-axially expanded polytetrafluoroethylene.

5. The blood contact surface of claim 4 wherein the expanded polytetrafluoroethylene comprises a bi-axially expanded polytetrafluoroethylene.

6. The blood contact surface of claim 1 wherein the expanded polytetrafluoroethylene comprises fibrils extended outwardly from the nodes in substantially perpendicular directions.

7. The blood contact surface of claim 1 wherein the mean width of the nodes comprises less than about 1.25 micron.

8. The blood contact surface of claim 1 wherein the mean width of the nodes is less than about 1 micron.

9. The blood contact surface of claim 1 wherein the ratio of mean distances between adjacent nodes in the x and y directions is less than 1.5 to 1.

10. The blood contact surface of claim 1 wherein the microstructure substantially prevents cellular in-growth.

11. The blood contact surface of claim 1 wherein the blood contact surface is incorporated in an implantable medical device.

12. The blood contact surface of claim 1 wherein the blood contact surface is incorporated in a non-implantable medical device.

13. The blood contact surface of claim 1 wherein the mean distance between adjacent nodes is less than about 4 micron.

14. The blood contact surface of claim 13 wherein the mean distance between adjacent nodes is less than about 3 micron.

15. The blood contact surface of claim 11 wherein the implantable medical device includes a stent.

16. The blood contact surface of claim 1 wherein endothelial cells attach intimately to the node and fibril microstructure.

* * * * *

UNITED STATES PATENT AND TRADEMARK OFFICE
CERTIFICATE OF CORRECTION

PATENT NO. : 9,775,933 B2
APPLICATION NO. : 13/773937
DATED : October 3, 2017
INVENTOR(S) : Keith A. Knisley et al.

Page 1 of 1

It is certified that error appears in the above-identified patent and that said Letters Patent is hereby corrected as shown below:

In the Claims

In Column 26, Line 3, Claim 2, replace "about 2:1 to 1.1." with --about 2:1 to 1:1.--

Signed and Sealed this
Twenty-eighth Day of May, 2019

Andrei Iancu
*Director of the United States Patent and Trademark Office*